(12) United States Patent
Anssari Moin et al.

(10) Patent No.: US 11,568,533 B2
(45) Date of Patent: Jan. 31, 2023

(54) AUTOMATED CLASSIFICATION AND TAXONOMY OF 3D TEETH DATA USING DEEP LEARNING METHODS

(71) Applicant: Promaton Holding B.V., Amsterdam (NL)

(72) Inventors: David Anssari Moin, Amsterdam (NL); Frank Theodorus Catharina Claessen, Amsterdam (NL); Bas Alexander Verheij, Amsterdam (NL)

(73) Assignee: PROMATON HOLDING B.V., Amsterdam (NL)

( * ) Notice: Subject to any disclaimer, the term of this patent is extended or adjusted under 35 U.S.C. 154(b) by 0 days.

(21) Appl. No.: 16/652,886

(22) PCT Filed: Oct. 2, 2018

(86) PCT No.: PCT/EP2018/076871
§ 371 (c)(1),
(2) Date: Apr. 1, 2020

(87) PCT Pub. No.: WO2019/068741
PCT Pub. Date: Apr. 11, 2019

(65) Prior Publication Data
US 2020/0320685 A1  Oct. 8, 2020

(30) Foreign Application Priority Data
Oct. 2, 2017 (EP) ...................................... 17194460

(51) Int. Cl.
*G06T 7/11* (2017.01)
*G06T 7/00* (2017.01)
(Continued)

(52) U.S. Cl.
CPC .............. *G06T 7/0012* (2013.01); *A61B 6/14* (2013.01); *A61B 6/466* (2013.01); *G06N 3/08* (2013.01);
(Continued)

(58) Field of Classification Search
CPC  G06N 3/00; G06N 20/00; G06N 3/08; G06N 3/0427; G06N 3/0454; G06T 15/00;
(Continued)

(56) References Cited

U.S. PATENT DOCUMENTS 6,721,387 B1  4/2004  Naidu et al.
8,135,569 B2  3/2012  Matov et al.
(Continued)

FOREIGN PATENT DOCUMENTS

CN  101977564 A  2/2011
CN  106618760 A  5/2017
(Continued)

OTHER PUBLICATIONS

Szegedy et al "Going deeper with convolutions" (Year: 2014).*
(Continued)

*Primary Examiner* — Tsung Yin Tsai
(74) *Attorney, Agent, or Firm* — Steven M. Koehler; Westman, Champlin & Koehler, P.A.

(57) ABSTRACT

A computer-implemented method for automated classification of 3D image data of teeth includes a computer receiving one or more of 3D image data sets where a set defines an image volume of voxels representing 3D tooth structures within the image volume associated with a 3D coordinate system. The computer pre-processes each of the data sets and provides each of the pre-processed data sets to the input of a trained deep neural network. The neural network classifies each of the voxels within a 3D image data set on the basis of a plurality of candidate tooth labels of the
(Continued)

dentition. Classifying a 3D image data set includes generating for at least part of the voxels of the data set a candidate tooth label activation value associated with a candidate tooth label defining the likelihood that the labelled data point represents a tooth type as indicated by the candidate tooth label.

12 Claims, 24 Drawing Sheets

(51) Int. Cl.
    *A61B 6/14*            (2006.01)
    *A61B 6/00*            (2006.01)
    *G06N 3/08*           (2006.01)
    *G06T 11/00*          (2006.01)

(52) U.S. Cl.
    CPC .............. *G06T 7/11* (2017.01); *G06T 11/005* (2013.01); *G06T 11/008* (2013.01); *G06T 2200/04* (2013.01); *G06T 2207/10072* (2013.01); *G06T 2207/20081* (2013.01); *G06T 2207/20084* (2013.01); *G06T 2207/30036* (2013.01)

(58) Field of Classification Search
    CPC ....... G06T 17/00; G06T 19/00; G06T 7/0012; G06T 7/11; G06T 11/005; G06T 11/008; G06T 2200/04; G06T 2207/10072; G06T 2207/20081; G06T 2207/20084; G06T 2207/30036; G06V 40/00; A61B 6/14; A61B 6/466; G06K 2209/055; G06K 9/34; G06K 9/4628; G06K 9/00214; G06K 9/627

See application file for complete search history.

(56) References Cited

U.S. PATENT DOCUMENTS

| | | | |
|---|---|---|---|
| 8,439,672 B2 | 5/2013 | Matov et al. | |
| 8,639,477 B2 | 1/2014 | Chelnokov et al. | |
| 9,107,722 B2 | 8/2015 | Matov et al. | |
| 9,135,498 B2 | 9/2015 | Andreiko et al. | |
| 9,904,999 B2 | 2/2018 | Andreiko et al. | |
| 10,032,271 B2 | 7/2018 | Somasundaram et al. | |
| 10,235,606 B2 | 3/2019 | Miao et al. | |
| 10,456,229 B2 | 10/2019 | Fisker et al. | |
| 10,610,185 B2 | 4/2020 | Taguchi et al. | |
| 10,685,259 B2 | 6/2020 | Salah et al. | |
| 10,932,890 B1 | 3/2021 | Sant et al. | |
| 10,997,727 B2* | 5/2021 | Xue ..................... G06V 10/751 | |
| 11,007,036 B2 | 5/2021 | Pokotilov et al. | |
| 11,107,218 B2 | 8/2021 | Salah et al. | |
| 2008/0253635 A1 | 10/2008 | Spies et al. | |
| 2009/0191503 A1 | 7/2009 | Matov et al. | |
| 2010/0069741 A1 | 3/2010 | Kuhn et al. | |
| 2011/0038516 A1 | 2/2011 | Koehler et al. | |
| 2011/0081071 A1 | 4/2011 | Benson et al. | |
| 2011/0255765 A1 | 10/2011 | Carlson et al. | |
| 2012/0063655 A1 | 3/2012 | Dean et al. | |
| 2013/0022251 A1 | 1/2013 | Chen et al. | |
| 2013/0039556 A1 | 2/2013 | Kachelriess et al. | |
| 2013/0230818 A1 | 9/2013 | Matov et al. | |
| 2014/0169648 A1 | 6/2014 | Andreiko et al. | |
| 2014/0227655 A1 | 8/2014 | Andreiko et al. | |
| 2015/0029178 A1 | 1/2015 | Claus et al. | |
| 2016/0008095 A1 | 1/2016 | Matov et al. | |
| 2016/0034788 A1 | 2/2016 | Lin et al. | |
| 2016/0042509 A1 | 2/2016 | Andreiko et al. | |
| 2016/0078647 A1 | 3/2016 | Schildkraut et al. | |
| 2016/0117850 A1 | 4/2016 | Jin et al. | |
| 2016/0324499 A1 | 11/2016 | Sen Sharma et al. | |
| 2016/0371862 A1 | 12/2016 | Silver et al. | |
| 2017/0024634 A1 | 1/2017 | Miao et al. | |
| 2017/0046616 A1 | 2/2017 | Socher et al. | |
| 2017/0100212 A1 | 4/2017 | Sherwood et al. | |
| 2017/0150937 A1 | 6/2017 | Stille et al. | |
| 2017/0169562 A1 | 6/2017 | Somasundaram et al. | |
| 2017/0265977 A1 | 9/2017 | Fisker et al. | |
| 2017/0270687 A1 | 9/2017 | Manhart | |
| 2018/0028294 A1* | 2/2018 | Azernikov ........... G06K 9/6274 | |
| 2018/0110590 A1 | 4/2018 | Maraj et al. | |
| 2018/0182098 A1 | 6/2018 | Andreiko et al. | |
| 2018/0300877 A1 | 10/2018 | Somasundaram et al. | |
| 2019/0026599 A1 | 1/2019 | Salah et al. | |
| 2019/0147666 A1 | 5/2019 | Keustermans et al. | |
| 2019/0164288 A1 | 5/2019 | Wang et al. | |
| 2019/0172200 A1 | 6/2019 | Andreiko et al. | |
| 2019/0180443 A1* | 6/2019 | Xue .................... G06K 9/6274 | |
| 2019/0282333 A1 | 9/2019 | Matov et al. | |
| 2019/0328489 A1* | 10/2019 | Capron-Richard .. A61B 6/5247 | |
| 2020/0015948 A1 | 1/2020 | Fisker et al. | |
| 2020/0022790 A1 | 1/2020 | Fisker | |
| 2020/0085535 A1 | 3/2020 | Pokotilov et al. | |
| 2020/0179089 A1 | 6/2020 | Serval et al. | |
| 2020/0320685 A1* | 10/2020 | Anssari Moin ........ G06V 10/26 | |
| 2021/0045843 A1 | 2/2021 | Pokotilov et al. | |
| 2021/0082184 A1 | 3/2021 | Claessen et al. | |
| 2021/0110584 A1 | 4/2021 | Claessen et al. | |
| 2021/0150702 A1 | 5/2021 | Claessen et al. | |
| 2021/0174543 A1 | 6/2021 | Claessen et al. | |
| 2021/0217233 A1 | 7/2021 | Feng et al. | |
| 2021/0264611 A1 | 8/2021 | Xue et al. | |
| 2021/0322136 A1 | 10/2021 | Anssari Moin et al. | |

FOREIGN PATENT DOCUMENTS

| | | | |
|---|---|---|---|
| CN | 108205806 A | 6/2018 | |
| CN | 108305684 A | 7/2018 | |
| EP | 2742857 A1 | 6/2014 | |
| EP | 3121789 A1 | 1/2017 | |
| EP | 3462373 A1 | 4/2019 | |
| EP | 3591616 A1 | 1/2020 | |
| EP | 3671531 A1 | 6/2020 | |
| EP | 3767521 A1 | 1/2021 | |
| JP | 2010-220742 A | 10/2010 | |
| JP | 2013-537445 A | 10/2013 | |
| JP | 2017-102622 A | 6/2017 | |
| JP | 2017-520292 A | 7/2017 | |
| JP | 2017-157138 A | 9/2017 | |
| WO | 2015169910 A1 | 11/2015 | |
| WO | 2017099990 A1 | 6/2017 | |
| WO | WO-2017099990 A1 * | 6/2017 | ........... A61B 5/0088 |
| WO | 2019002631 A1 | 1/2019 | |
| WO | 2019068741 A2 | 4/2019 | |
| WO | 2020007941 A1 | 1/2020 | |
| WO | 2020127398 A1 | 6/2020 | |
| WO | 2021009258 A1 | 1/2021 | |

OTHER PUBLICATIONS

Mikia et al "Classification of teeth in cone-beam CT using deep convolutional neural network" (Year: 2016).*
Gutierrez-Becker et al. "Learning Optimization Updates for Multimodal Registration", Medical Image Computing and Computer-Assisted Intervention—MICCAI 2016, 2016, pp. 19-27.
Hosntalab et al. "A Hybrid Segmentation Framework for Computer-Assisted Dental Procedures", IEICE Transactions on Information and Systems, Oct. 2009, pp. 2137-2151, vol. E92D, No. 10.
Studholme et al. "Automated Three-Dimensional Registration of Magnetic Resonance and Positron Emission Tomography Brain Images by Multiresolution Optimization of Voxel Similarity Measures", Medical Physics, 1997, pp. 25-35, vol. 24. No. 1.
Çiçek et al. "3D U-Net: Learning Dense Volumetric Segmentation from Sparse Annotation", Medical Image Computing and Computer-Assisted Intervention—MICCAI 2016, Part II, Oct. 2, 2016, pp. 424-432.
Gjesteby et al. "Deep Learning Methods for CT Image-Domain Metal Artifact Reduction", SPIE, Developments in X-Ray Tomography XI, Sep. 25, 2017, 6 pages, vol. 10391.

(56) References Cited

OTHER PUBLICATIONS

Gkantidis et al. "Evaluation of 3-Dimensional Superimposition Techniques on Various Skeletal Structures of the Head Using Surface Models", PLOS One, Feb. 23, 2015, 20 pages, vol. 10, No. 2.
Hall, P. and Owen, M. "Simple Canonical Views", Proceedings of the British Machine Vision Conference (BMVC), Sep. 2005, 10 pages.
Han et al. "Deep Residual Learning for Compressed Sensing CT Reconstruction via Persistent Homology Analysis", Cornell University Library, Nov. 19, 2016, pp. 1-10.
Hongming Li, Y. "Non-Rigid Image Registration Using Fully Convolutional Networks With Deep Self-Supervision", Sep. 3, 2017, 8 pages.
Isola et al. "Image-to-Image Translation with Conditional Adversarial Networks", 2017 IEEE Conference on Computer Vision and Pattern Recognition (CVPR), Honolulu, HI, 2017, pp. 5967-5976.
Joda, T. and Gallucci, G. "Systematic Literature Review of Digital Three-Dimensional Superimposition Techniques to Create Virtual Dental Patients", The International Journal of Oral & Maxillofacial Implants, 2015, pp. 330-337, vol. 30, No. 2.
Jung et al. "Combining Volumetric Dental CT and Optical Scan Data for Teeth Modeling", Computer-Aided Design, Oct. 2015, pp. 24-37, vol. 67-68.
Li et al. "PointCNN: Convolution On X-Transformed Points", Neural Information Processing Systems (NIPS), Nov. 5, 2018, 11 pages.
Liao et al. "Automatic Tooth Segmentation of Dental Mesh Based on Harmonic Fields", Biomedical Research International, 2015, 10 pages, vol. 2015.
Litjens et al. "A Survey on Deep Learning in Medical Image Analysis", Medical Image Analysis, Dec. 2017, pp. 60-88, vol. 42.
Meyer et al. "Normalized Metal Artifact Reduction (NMAR) in Computed Tomography", Medical Physics, Oct. 2010, pp. 5482-5493, vol. 37, No. 10.
Pavaloiu et al. "Automatic Segmentation for 3D Dental Reconstruction", IEEE 6th ICCCNT, Jul. 13-15, 2015, 6 pages.
Pavaloiu et al. "Neural Network Based Edge Detection for CBCT Segmentation", 5th IEEE EHB, Nov. 19-21, 2015.
Qi et al. "PointNet: Deep Learning on Point Sets for 3D Classification and Segmentation", Computer Vision and Pattern Recognition (CVPR), 2017, 19 pages.
Ruellas et al. "3D Mandibular Superimposition: Comparison of Regions of Reference for Voxel-Based Registration" PLOS One, Jun. 23, 2016, 13 pages.
Schulze et al. "Artefacts in CBCT: A Review", Dentomaxillofacial Radiology, Jul. 1, 2011, pp. 265-273, vol. 40, No. 5.
Simonovsky et al. "A Deep Metric for Multimodal Registration" International Conference on Medical Image Computing and Computer-Assisted Intervention (MICCAI), 2016, pp. 10-18, vol. 9902.
Tonioni et al. "Learning to Detect Good 3D Keypoints", International Journal of Computer Vision, 2018, pp. 1-20, vol. 126.
Wang et al. "Dynamic Graph CNN for Learning on Point Clouds", ACM Trans. Graph, Jan. 2019, vol. 1, No. 1, 13 pages.
Wu et al. "Tooth Segmentation on Dental Meshes Using Morphologic Skeleton", Computers & Graphics, Feb. 2014, pp. 199-211, vol. 38.
Wu et al. "Model-Based Teeth Reconstruction", ACM Transactions on Graphics (TOG), ACM, US, Nov. 11, 2016, pp. 1-13, vol. 35, No. 6.
Yau et al. "Tooth Model Reconstruction Based Upon Data Fusion for Orthodontic Treatment Simulation", Computers in Biology and Medicine, May 1, 2014, pp. 8-16, vol. 48.
Yu, Y. "Machine Learning for Dental Image Analysis", Nov. 2016, 61 pages, https://arxiv.org/ftp/arxiv/papers/1611/1611.09958.pdf, retrieved Nov. 30, 2017.
Zhang, Y. and Yu, H. "Convolutional Neural Network Based Metal Artifact Reduction in X-Ray Computed Tomography", IEEE Transactions on Medical Imaging, Jun. 2018, pp. 1370-1381, vol. 37, No. 6.
Zhang, C. and Xing, Y. "CT Artifact Reduction via U-Net CNN", SPIE, Medical Imaging 2018: Image Processing, Mar. 2, 2018, 6 pages, vol. 10574.
Anjay Sekuboyina et al. "A Localisation-Segmentation Approach for Multi-label Annotation of Lumbar Vertebrae using Deep Nets", arxiv.org, Cornell University Library, 201 Olin Library Cornell University Ithaca, NY 14853, Mar. 13, 2017 (Mar. 13, 2017), abstract.
Auro Tripathy, "Five Insights from GoogLeNet You Could Use In Your Own Deep Learning Nets", Sep. 20, 2016 (Sep. 20, 2016), pp. 1-21, https://www.slideshare.net/aurot/googlenet-insights?from_action=save, retrieved Dec. 18, 2018.
Bustos B. et al., "An experimental comparison of feature-based 3D retrieval methods", 3D Data Processing, Visualization and Transmission, 2004. 3DPVT 2004. Proceedings. 2nd International Symposium on Thessaloniki, Greece Sep. 6-9, 2004, Piscataway, NJ, USA, IEEE, Sep. 6, 2004, pp. 215-222.
Byung Bok Ahn, "The Compact 3D Convolutional Neural Network for Medical Images", Jul. 2, 2017, pp. 1-9, http://cs231n.standord.edu/reports/2017/pdfs/23/pdf, retrieved Dec. 18, 2018, abstract.
Christian Szegedy et al., "Going deeper with convolutions", 2015 IEEE Conference on Computer Vision and Pattern Recognition (CVPR), Jun. 2015, pp. 1-9.
Duda R. O. et al., "Pattern Classification, Introduction", 2001, Pattern Classification, New York, John Wiley & Sons, US, pp. 1-13.
Duy Nguyen The et al., "Automatic Detection and Classification of Teeth in CT Data", 2012, ECCV 2016 Conference; [Lecture Notes in Computer Science; Lect. Notes Computer], Springer International Publishing, Cham, pp. 609-616.
Kaiming He et al., "Deep Residual Learning for Image Recognition", 2016 IEEE Conference on Computer Vision and Pattern Recognition (CVPR), Jun. 2016, pp. 770-778.
Klinder T. et al., "Automated model-based vertebra detection, identification, and segmentation in CT images", Medical Image Analysis, Oxford University Press, Oxford, GB, vol. 13, No. 3, Jun. 2009, pp. 471-482.
Mark Everingham et al., "The Pascal Visual Object Classes (VOC) Challenge", International Journal of Computer Vision., vol. 88, No. 2, Sep. 9, 2009, pp. 303-338.
Miki Yuma et al: "Classification of teeth in cone-beam CT using deep convolutional neural network", Computers in Biology and Medicine, New York, NY, US, vol. 80, Nov. 12, 2016, pp. 24-29.
Miki Yuma et al., "Tooth labeling in cone-beam CT using deep convulutional neural network for forensic identification", Progress in Biomedical Optics and Imaging, SPIE—International Society for Optical Engineering, Bellingham, WA, US, vol. 10134, Mar. 3, 2017, pp. 101343E-101343E.
Mohamed Chaouch et al., "A Novel Method for Alignment of 3D Models", Nov. 12, 2008, pp. 1-27, https://hal.inria.fr/hal-00804653/document, retrieved Mar. 29, 2018.
Ryu J. H. et al., "Analysis of skin movement with respect to flexional bone motion using MR images of a hand", Journal of Biomechanics, Pergamon Press, New York, NY, US, vol. 39, No. 5, 2006, pp. 844-852.
Tobias Fechter et al., "A 3D fully convolutional neural network and a random walker to segment the esophagus in CT", Apr. 21, 2017, https://arxiv.org/pdf/1704.06544.pdf, retrieved Dec. 18, 2018, abstract.
International Search Report dated Mar. 22, 2019, for corresponding International Patent Application No. PCT/EP2018/076871, filed Oct. 2, 2018.
Written Opinion of the International Searching Authority dated Mar. 22, 2019, for corresponding International Patent Application No. PCT/EP2018/076871, filed Oct. 2, 2018.
Chen et al. "Deep RBFNet: Point Cloud Feature Learning Using Radial Basis Functions", Cornell University Library, Dec. 11, 2018, 11 pages.
Chen et al. "Fast Resampling of 3D Point Clouds via Graphs", IEEE Transactions on Signal Processing, Feb. 1, 2018, pp. 666-681, vol. 66, No. 3.
Eun, H. and Kim, C. "Oriented Tooth Localization for Periapical Dental X-ray Images via Convolutional Neural Network", Asia-Pacific Signal and Information Processing Association Annual Summit and Conference (APSIPA), Dec. 3, 2016, pp. 1-7.

(56) References Cited

OTHER PUBLICATIONS

Fang et al. "3D Deep Shape Descriptor", 2015 IEEE Conference on Computer Vision and Pattern Recognition (CVPR), 2015, pp. 2319-2328.

Ghafoorian et al. "EL-GAN: Embedding Loss Driven Generative Adversarial Networks for Lane Detection", Computer Vision—ECCV 2018 Workshops, Jan. 23, 2019, pp. 256-272, vol. 11129.

Ghazvinian Zanjani et al. "Deep Learning Approach to Semantic Segmentation in 3D Point Cloud Intra-oral Scans of Teeth", Proceedings of the 2nd International Conference on Medical Imaging with Deep Learning, 2019, 22 pages, retrieved online from https://openreview.net/forum?id=ByxLSoblgV.

Somes et al. "Efficient 3D Object Recognition Using Foveated Point Clouds", Computers & Graphics, May 1, 2013, pp. 496-508, vol. 37.

Gorler, O. and Akkoyun, S. "Artificial Neural Networks Can be Used as Alternative Method to Estimate Loss Tooth Root Sizes for Prediction of Dental Implants", Cumhuriyet University Faculty of Science Science Journal (CSJ), Apr. 2017, pp. 385-395, vol. 38, No. 2.

Guo et al. "3D Mesh Labeling Via Deep Convolutional Neural Networks", ACM Transactions on Graphics, Dec. 2015, pp. 1-12, vol. 35, No. 1, Article 3.

Hermosilla et al. "Monte Carlo Convolution for Learning on Non-Uniformly Shaped Point Clouds", ACM Transactions on Graphics, Nov. 2018, 12 pages, vol. 37, No. 6, Article 235.

Hou et al. "3D-SIS: 3D Semantic Instance Segmentation of RGB-D Scans", Computer Vision and Pattern Recognition (CPR), Apr. 29, 2019, 14 pages.

Huang et al. "Edge-Aware Point Set Resampling", ACM Transactions on Graphics, 2013, pp. 1-12, vol. 32, No. 1, Article 9.

Johari et al. "Detection of Vertical Root Fractures in Intact and Endodontically Treated Premolar Teeth by Designing a Probabilistic Neural Network: An ex vivo Study", Dentomaxillofacial Radiology, Feb. 2017, vol. 46, No. 2, pp. 1-9.

Ku et al. "Joint 3D Proposal Generation and Object Detection from View Aggregation", IEEE/RSJ International Conference on Intelligent Robots and Systems (IROS), Jul. 12, 2018, pp. 1-8.

Le T. and Duan Y. "PointGrid: A Deep Network for 3D Shape Understanding", Proceedings of the IEEE Conference on Computer Vision and Pattern Recognition, Jun. 18-23, 2018, pp. 9204-9214.

Li et al. "SO-Net: Self-Organizing Network for Point Cloud Analysis", Eye In-Painting with Exemplar Generative Adversarial Networks, Jun. 2018, pp. 9397-9406.

Liu, C. and Furukawa, Y. "MASC: Multi-scale Affinity with Sparse Convolution for 3D Instance Segmentation", Computer Vision and Pattern Recognition (CPR), Feb. 12, 2019, 4 pages.

Qi et al. "Frustum PointNets for 3D Object Detection from RGB-D Data", Computer Vision and Pattern Recognition (CPR), Apr. 13, 2018, 15 pages.

Qi et al. "PointNet++: Deep Hierarchical Feature Learning on Point Sets in a Metric Space", Conference on Neural Information Processing Systems (NIPS), Jun. 2017, 14 pages.

Ravanbakhsh et al. "Deep Learning With Sets and Point Clouds", Feb. 24, 2017, 12 pages, retrieved online from https://arxiv.org/abs/1611.04500.

Silva et al. "Automatic Segmenting Teeth in X-Ray Images: Trends, A Novel Data Set, Benchmarking and Future Perspectives", Feb. 9, 2018, 33 pages, retrieved online from https://arxiv.org/pdf/1802.03086.pdf.

Skrodzki et al. "Directional Density Measure to Intrinsically Estimate and Counteract Non-Uniformity in Point Clouds", Computer Aided Geometric Design, Aug. 2018, pp. 73-89, vol. 64.

Shaoqing et al. "Mask R-CNN", Proceedings of the IEEE International Conference on Computer Vision, 2017, pp. 2961-2969.

Tian, S. "Automatic Classification and Segmentation of Teeth on 3D Dental Model Using Hierarchical Deep Learning Networks" IEEE Journals & Magazine, Jun. 21, 2019, pp. 84817-84828.

Wang et al. "SGPN: Similarity Group Proposal Network for 3D Point Cloud Instance Segmentation", CVF Conference on Computer Vision and Pattern Recognition, Nov. 23, 2017, 13 pages.

Wu et al. "3D ShapeNets: A Deep Representation for Volumetric Shapes", 2015 IEEE Conference on Computer Vision and Pattern Recognition (CVPR), 2015, pp. 1912-1920.

Xu et al. "SpiderCNN: Deep Learning on Point Sets with Parameterized Convolutional Filters", Computer Vision—EECV, 2018, 16 pages.

Yi et al. "GSPN: Generative Shape Proposal Network for 3D Instance Segmentation in Point Cloud", Proceedings of the IEEE/CVF Conference on Computer Vision and Pattern Recognition (CVPR), 2019, 13 pages.

Zhou et al. "A Method for Tooth Model Reconstruction Based on Integration of Multimodal Images", Journal of Healthcare Engineering, Jun. 20, 2018, vol. 8, pp. 1-8.

Office Action in corresponding Japanese Patent Application No. 2020-519080 dated Aug. 22, 2022.

* cited by examiner

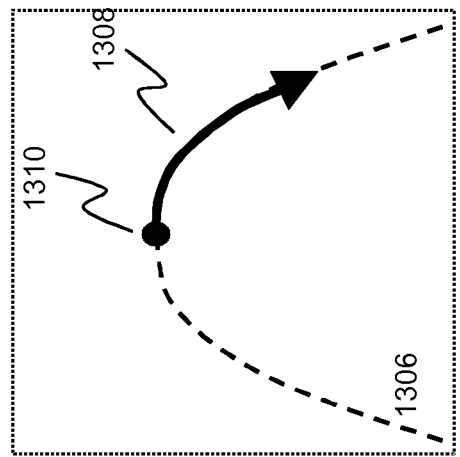
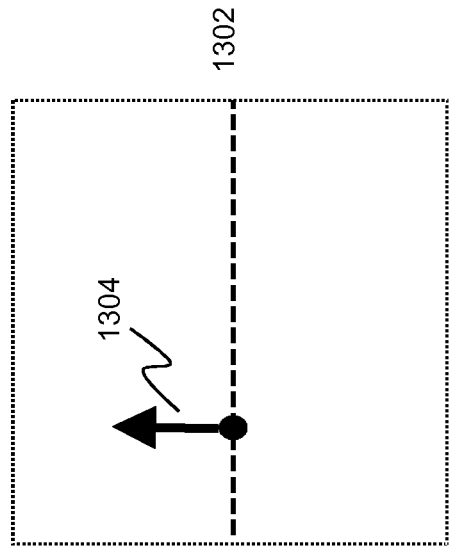
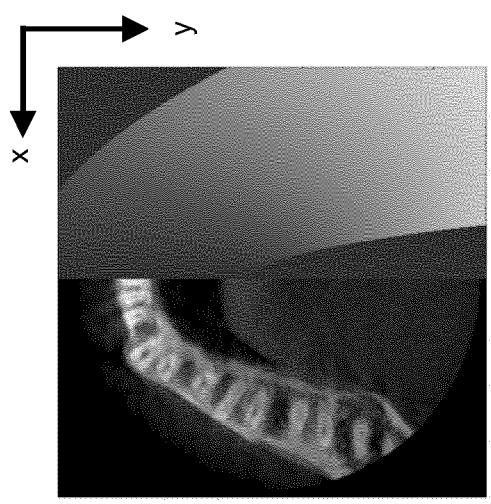
FIG. 13A
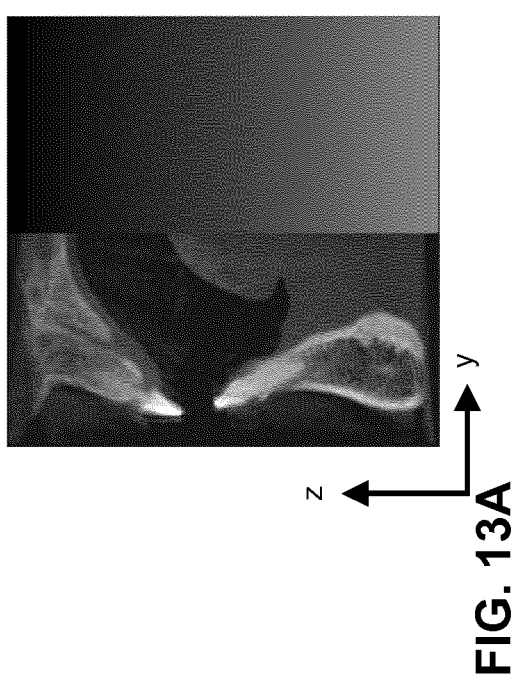
FIG. 13B

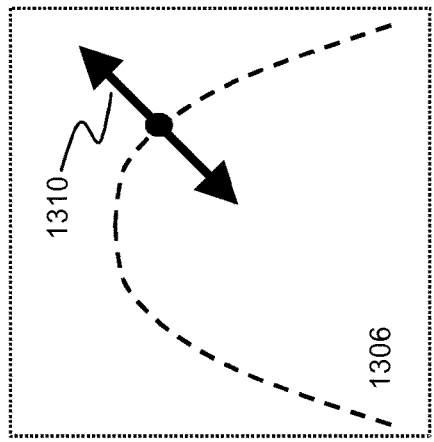
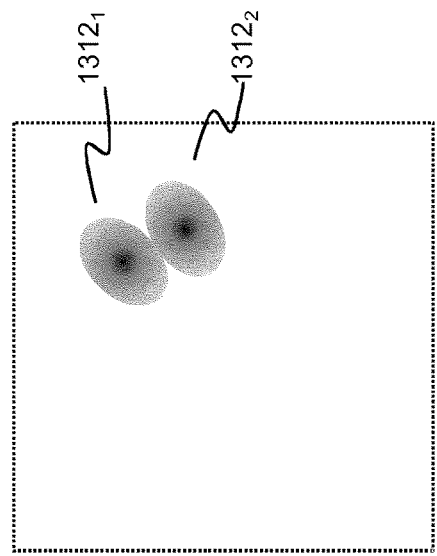
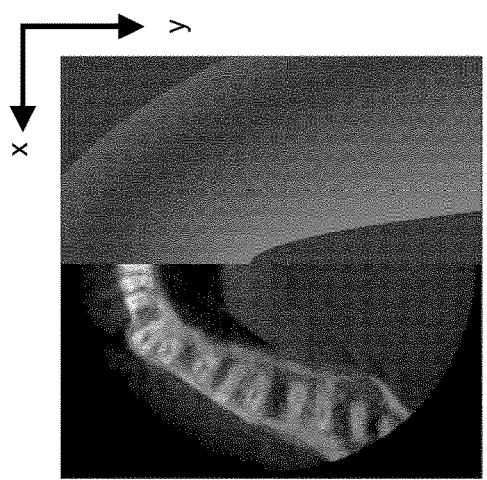
FIG. 13C
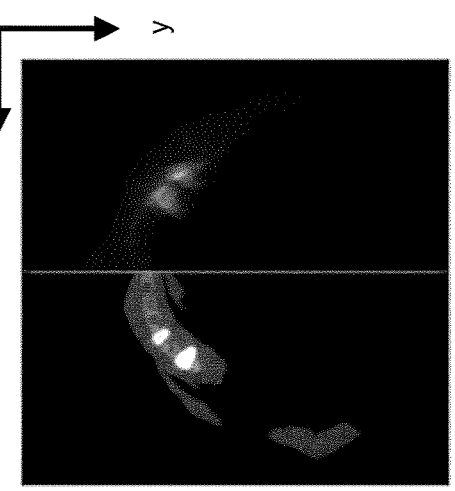
FIG. 13D

*(Two digit numbers are FDI two digit notation)*

AUTOMATED CLASSIFICATION AND TAXONOMY OF 3D TEETH DATA USING DEEP LEARNING METHODS

CROSS-REFERENCE TO RELATED APPLICATION

The present application is a national stage of and claims priority of International patent application Serial No. PCT/EP2018/076871, filed Oct. 2, 2018, and published in English as WO2019068741A2.

FIELD OF THE INVENTION

The invention relates to automated localization, classification and taxonomy of 3D teeth data using deep learning methods, and, in particular, though not exclusively, to systems and methods for automated localization, classification and taxonomy of 3D teeth data using deep learning methods, a method for training such deep learning neural network, and a computer program product for using such method.

BACKGROUND OF THE INVENTION

Reliable identification of tooth types and teeth arrangements play a very important role in a wide range of applications including (but not limited) to dental care and dental reporting, orthodontics, orthognathic surgery, forensics and biometrics. Therefore, various computer-assisted techniques have been developed to automate or at least partly automate the process of classifying and numbering teeth in accordance with a known dental notation scheme. Additionally, any reduction in time that is needed for reliably classifying and taxonomizing teeth would be beneficial in such fields of application.

For the purpose of this disclosure, 'tooth' refers to a whole tooth including crown and root, 'teeth' refers to any set of teeth consisting of two or more teeth, whereas a set of teeth originating from a single person will be referred to as originating from a 'dentition'. A dentition may not necessarily contain the total set of teeth of an individual. Further, 'classification' refers to identifying to which of a set of categories an observation or sample belongs. In the case of tooth-taxonomy, classification refers to the process of identifying to which category (or label) a single tooth belongs. 'Taxonomy' refers to the process of deriving a tooth class for all individual teeth from a single dentition and 3D teeth data refers to any digital representation of any (set of) teeth, e.g. a 3D voxel representation of a filled volume, densities in a volume, a 3D surface mesh, etc. Further, 3D teeth data representing a dentition may either include a full set of teeth or a part of a full set. Unless stated differently, in this application the term 'segmentation' refers to semantic segmentation, which refers to dense predictions for every voxel so that each voxel of the input space is labelled with a certain object class. In contrast to bounding box segmentation, which relates to finding region boundaries, semantic segmentation yields semantically interpretable 3D masks within the input data space.

For example, US2017/0169562 describes a system for automatic tooth type recognition on the basis of intra-oral optical 3D scans. Such an intra-oral optical scanner is capable of generating a 3D scan of the exposed parts of the teeth, i.e. the crown of the teeth. The shape of each crown is derived from the 3D scan and represented in form of a 3D mesh, including faces and vertices. These 3D meshes are subsequently used to determine aggregated features for each tooth. The thus obtained aggregated features and the associated tooth type are then used as training data for training classifiers making use of traditional machine learning methodologies such as support vector machines or decision trees.

Although this system is capable of processing high-resolution intra-oral 3D scans as input data, it is not capable of processing volumetric dento-maxillofacial images which are generated using Cone Beam Computed tomography (CBCT). CBCT is a medical imaging technique using X-ray computed tomography wherein the X-ray radiation is shaped into a divergent cone of low-dosage. CBCT imaging is the most used 3D imaging technique in the dental field and generates 3D image data of dento-maxillofacial structures, which may include (parts of) jaw bones, complete or partial tooth structures including the crown and the roots and (parts of) the inferior alveolar nerve. Image analysis of CBCT image data however poses a substantial problem as in CBCT scans the radio density, measured in Hounsfield Units (HUs), is not consistent because different areas in the scan appear with different greyscale values depending on their relative positions in the organ being scanned. HUs measured from the same anatomical area with both CBCT and medical-grade CT scanners are not identical and are thus unreliable for determination of site-specific, radiographically-identified bone density.

Moreover, CBCT systems for scanning dento-maxillofacial structures do not employ a standardized system for scaling the grey levels that represent the reconstructed density values. These values are as such arbitrary and do not allow for e.g. assessment of bone quality. In the absence of such a standardization, it is difficult to interpret the grey levels or impossible to compare the values resulting from different machines. Moreover, the teeth roots and jaw bone structures have similar densities such that it is difficult for a computer to e.g. distinguish between voxels belonging to teeth and voxels belonging to a jaw. Additionally, CBCT systems are very sensitive to so-called beam hardening, which produces dark streaks between two high attenuation objects (such as metal or bone), with surrounding bright streaks. The above-mentioned problems make full automatic segmentation of dento-maxillofacial structures and classification of segmented tooth structures, and more general, automated taxonomy of 3D teeth data derived from 3D CBCT image data particularly challenging.

This problem is for example discussed and illustrated in the article by Miki et al, "Classification of teeth in cone-beam CT using deep convolutional neural network", Computers in Biology and Medicine 80 (2017) pp. 24-29. In this article, a 2D deep convolutional neural network system is described that was trained to classify 2D CBCT bounding box segmentations of teeth into seven different tooth types. As described in this article, due to the problems related to the analysis of CBCT image data both manual pre-processing of the training data and the test data was needed, including manual selection of regions of interest (bounding boxes) enclosing a tooth from an axial 2D slice and omission of ROIs including metal artefacts.

In their article, Miki et al suggested that the accuracy could be improved using 3D CNN layers instead of 2D CNN layers. Taking the same neural network architectural principles however, converting these to a 3D variant would lead to compromises regarding the granularity of data, in particular the maximum resolution (e.g. mm represented per datapoint, being a 2D pixel or a 3D voxel) in applicable orthogonal directions. Considering computational requirements, in particular memory bandwidth required for processing, such 3D bounding box voxels will have a considerably lower resolution than would be possible for 2D bounding boxes of a 2D axial slice. Thus, the benefit of having information available for the entire 3D volume containing a tooth will in practice be downplayed by a removal of information due to a down-sampling of the image that is necessary to process the voxels based on a reasonable computational load. Especially in troublesome regions of 3D CBCT data, such as e.g. transitions between individual teeth or between bone and teeth, this will negatively affect a sufficiently accurate classification result per tooth.

Where the previously discussed article by Miki et al considers automatic classification based on manual bounding box segmentation, automatic bounding box segmentation (hence tooth localization and the possibility of full automatic classification) is addressed in a later published article by the same authors, Miki et al, "*Tooth labelling in cone-beam CT using deep convolutional neural network for forensic identification*", Progress in Biomedical Optics and Imaging 10134 (2017) pp. 101343E-1-10134E-6. In this article, again in the 2D domain of axial slices of CBCT scans, a convolutional neural network is trained and utilized to produce a heatmap indicating the per pixel likelihood of belonging to a tooth region. This heatmap is filtered and 2D bounding boxes containing teeth are selected through a non-maximum suppression method. Positive and negative example bounding boxes are employed for training a convolutional neural network as referenced in their first discussed article, and a trained network was evaluated. Again, when trying to adapt this methodology to function on 3D image data the same considerations as above need to be taken into account. Conversion of the same neural network architectural principles to a 3D CNN for generating a 3D heat map will result in a significantly long processing time. Additionally, also in this case, the necessity of down-sampling in order to cope with bandwidth limitations will have a negative impact on the segmentation and classification performance.

Thus, trying to extrapolate the 2D case described by Miki et al to a 3D case would lead in almost all cases to bounding boxes (voxels) with a lower accuracy than would be possible from the original input data set resolution, thereby significantly reducing the accurately predicting the confidence of a pixel being part of a tooth region (e.g. a pixel that is part of a slice containing jaw bone but incidentally 'looking like' a tooth may be incorrectly attributed with a high confidence of tooth). The low resolution will have especially consequences for the accuracy of the classification results. The network receives little to no information considering neighboring tooth-, tissue-, bone-structures, etc. Such information would be highly valuable not only for determining the seven classes of tooth as researched by Miki et al, but would also yield higher classification accuracy potential considering all 32 individual tooth types as may be present in a healthy dentition of an adult.

Additionally, where a tooth is only partially present in a received 3D image, as often occurs in the case of CBCT scans of a quadrant where parts of a tooth are beyond the field of view of a scanning device, the fact that the networks have trained on images containing complete teeth will again be detrimental to both identification of a tooth region, and to the classification of a tooth.

The above-mentioned problems make the realization of a system that is capable of fully automated localization, classification and taxonomy of 3D teeth data within certain computation constraints very challenging, especially if the automated taxonomy of the 3D teeth data is based on volumetric 3D CBCT data.

Hence, there is a need in the art for computer systems that are adapted to accurately localize, classify and taxonomize sets of 3D tooth data, in particular 3D tooth data derived from heterogeneous volumetric 3D CBCT image data, into individual tooth types. In particular, there is a need in the art for computer systems that are adapted to accurately and timely localize, classify and taxonomize 3D teeth data into teeth types into a data structure which links sets of data representing teeth in 3D to objects corresponding to the 32 possible teeth of an adult.

SUMMARY OF THE INVENTION

As will be appreciated by one skilled in the art, aspects of the present invention may be embodied as a system, method or computer program product. Accordingly, aspects of the present invention may take the form of an entirely hardware embodiment, an entirely software embodiment (including firmware, resident software, micro-code, etc.) or an embodiment combining software and hardware aspects that may all generally be referred to herein as a "circuit," "module" or "system". Functions described in this disclosure may be implemented as an algorithm executed by a microprocessor of a computer. Furthermore, aspects of the present invention may take the form of a computer program product embodied in one or more computer readable medium(s) having computer readable program code embodied, e.g., stored, thereon.

Any combination of one or more computer readable medium(s) may be utilized. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus, or device.

A computer readable signal medium may include a propagated data signal with computer readable program code embodied therein, for example, in baseband or as part of a carrier wave. Such a propagated signal may take any of a variety of forms, including, but not limited to, electromagnetic, optical, or any suitable combination thereof. A computer readable signal medium may be any computer readable medium that is not a computer readable storage medium and that can communicate, propagate, or transport a program for use by or in connection with an instruction execution system, apparatus, or device.

Program code embodied on a computer readable medium may be transmitted using any appropriate medium, including but not limited to wireless, wireline, optical fiber, cable, RF, etc., or any suitable combination of the foregoing. Computer program code for carrying out operations for aspects of the present invention may be written in any combination of one or more programming languages, including a functional or an object oriented programming language such as Java™, Scala, C++, Python or the like and conventional procedural programming languages, such as the "C" programming language or similar programming languages. The program code may execute entirely on the user's computer, partly on the user's computer, as a stand-alone software package, partly on the user's computer and partly on a remote computer, or entirely on the remote computer, server or virtualized server. In the latter scenario, the remote computer may be connected to the user's computer through any type of network, including a local area network (LAN) or a wide area network (WAN), or the connection may be made to an external computer (for example, through the Internet using an Internet Service Provider).

Aspects of the present invention are described below with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer program instructions. These computer program instructions may be provided to a processor, in particular a microprocessor or central processing unit (CPU), or graphics processing unit (GPU), of a general purpose computer, special purpose computer, or other programmable data processing apparatus to produce a machine, such that the instructions, which execute via the processor of the computer, other programmable data processing apparatus, or other devices create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

The flowchart and block diagrams in the figures illustrate the architecture, functionality, and operation of possible implementations of systems, methods and computer program products according to various embodiments of the present invention. In this regard, each block in the flowchart or block diagrams may represent a module, segment, or portion of code, which comprises one or more executable instructions for implementing the specified logical function(s). It should also be noted that, in some alternative implementations, the functions noted in the blocks may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustrations, and combinations of blocks in the block diagrams and/or flowchart illustrations, can be implemented by special purpose hardware-based systems that perform the specified functions or acts, or combinations of special purpose hardware and computer instructions.

In first aspect, the invention may relate to a computer-implemented method for processing 3D data representing a dento-maxillofacial structure. The method may comprise: a computer receiving 3D data, preferably 3D cone beam CT, CBCT, data, the 3D data including a voxel representation of the dento-maxillofacial structure, the dento-maxillofacial structure comprising a dentition, a voxel at least being associated with a radiation intensity value, the voxels of the voxel representation defining an image volume; the computer providing the voxel representation to the input of a first 3D deep neural network, the 3D deep neural network being trained to classify voxels of the voxel representation into one or more tooth classes, preferably into at least 32 tooth classes of a dentition; the first deep neural network comprising a plurality of first 3D convolutional layers defining a first convolution path and a plurality of second 3D convolutional layers defining a second convolutional path parallel to the first convolutional path, the first convolutional path configured to receive at its input a first block of voxels of the voxel representation and the second convolutional path being configured to receive at its input a second block of voxels of the voxel representation, the first and second block of voxels having the same or substantially the same center point in the image volume and the second block of voxels representing a volume in real-world dimensions that is larger than the volume in real-world dimensions of the first block of voxels, the second convolutional path determining contextual information for voxels of the first block of voxels; the output of the first and second convolutional path being connected to at least one fully connected layer for classifying voxels of the first block of voxels into one or more tooth classes; and, the computer receiving classified voxels of the voxel representation of the dento-maxillofacial structure from the output of the first 3D deep neural network.

By employing such a 3D neural network architecture, individual tooth classification can be both trained upon and inferred using as much information relevant to the problem as possible, at appropriate scales, giving modern hardware limitations. Not only is it highly performant considering both localization of tooth structure (yielding a semantic segmentation at the native resolution of the received 3D data) and classification of such structure (uniquely classifying each tooth as may be uniquely present in a healthy dentition of an adult), it is also performant considering duration required due to its ability to process a multitude of output voxels in parallel. Due to the nature in which samples are be offered to the 3D deep neural network, classification can also be performed on teeth only partially present in a scan.

In an embodiment, the volume of the second block of voxels may be larger than the volume of the first block of voxels, the second block of voxels representing a down-sampled version of the first block of voxels, preferably the down-sampling factor being selected between 20 and 2, more preferably between 10 and 3.

In an embodiment, the method may further comprise: the computer determining one or more voxel representations of single tooth of the dento-maxillofacial structure on the basis of the classified voxels; the computer providing each of the one or more voxel representations of single tooth to the input of a second 3D deep neural network, the second 3D deep neural network being trained to classify a voxel representation of a single tooth into one of a plurality of tooth classes of a dentition, each tooth class being associated with a candidate tooth class label, the second trained 3D neural network generating for each of the candidate tooth class labels an activation value, an activation value associated with a candidate tooth class label defining the likelihood that a voxel representation of a single tooth represents a tooth class as indicated by the candidate tooth class label.

In an embodiment, the method may further comprise: determining a taxonomy of the dentition including: defining candidate dentition states, each candidate state being formed by assigning a candidate tooth class label to each of a plurality of voxel representations of single tooth based on the activation values; and, evaluating the candidate dentition states on the basis of one or more conditions, at least one of the one or more conditions requiring that different candidate tooth class labels assigned different voxel representations of single tooth.

In an embodiment, the method may further comprise: the computer using a pre-processing algorithm to determine 3D positional feature information of the dento-maxillofacial structure, the 3D positional feature information defining for each voxel in the voxel representation information about the position of the voxel relative to the position of a dental reference object, e.g. a jaw, a dental arch and/or one or more teeth, in the image volume, and; the computer adding the 3D positional feature information to the 3D data before providing the 3D data to the input of the first deep neural network, the added 3D positional feature information providing an additional data channel to the 3D data.

In an embodiment, the method may further comprise: the computer post-processing the voxels classified by the first 3D deep neural network on the basis of a third trained neural network, the third deep neural network being trained to receive voxels that are classified by the first deep neural network at its input and to correct voxels that are incorrectly classified by the first deep neural network, preferably the third neural network being trained based on voxels that are classified during the training of the first deep neural network as input and based on the one or more 3D data sets of parts of the dento-maxillofacial structures of the 3D image data of the training set as a target.

In a further aspect, the invention relates to a method for training a deep neural network system to process 3D image data of a dento-maxillofacial structure. The method may include a computer receiving training data, the training data including: 3D input data, preferably 3D cone beam CT (CBCT) image data, the 3D input data defining one or more voxel representations of one or more dento-maxillofacial structures respectively, a voxel being associated with a radiation intensity value, the voxels of a voxel representation defining an image volume; and, the training data further including: 3D data sets of parts of the dento-maxillofacial structures represented by the 3D input data of the training data; the computer using a pre-processing algorithm to determine 3D positional feature information of the dento-maxillofacial structure, the 3D positional feature information defining for each voxel in the voxel representation information about the position of the voxel relative to the position of a dental reference object, e.g. a jaw, a dental arch and/or one or more teeth, in the image volume; and, using the training data and the one or more 3D positional features to train the first deep neural network to classify voxels into one or more tooth classes, preferably into at least 32 tooth classes of a dentition.

In an embodiment, the method may further comprise: using voxels that are classified during the training of the first deep neural network and the one or more 3D data sets of parts of the dento-maxillofacial structures of the 3D image data of the training set to train a second neural network to post-process voxels classified by the first deep neural network, wherein the post-processing by the third neural network includes correcting voxels that are incorrectly classified by the first deep neural network.

In an embodiment, the method may comprise: using the 3D data sets, being voxel representations of single teeth to be used as targets for training at least the first deep neural network, to select a subset of voxels from at least the 3D image data being used as training input to the first deep neural network, the subset being used as input for training of a third deep neural network; and, using the tooth class label as associated with the 3D data set serving as target for training at least the first deep neural network as the target tooth class label for training the third deep neural network.

In an aspect, the method may relate to a computer system, preferably a server system, adapted to automatically classify 3D image data of teeth comprising: a computer readable storage medium having computer readable program code embodied therewith, the program code including a classification algorithm and a deep neural network, the computer readable program code; and a processor, preferably a microprocessor, coupled to the computer readable storage medium, wherein responsive to executing the first computer readable program code, the processor is configured to perform executable operations comprising: receiving 3D image data, preferably 3D cone beam CT (CBCT) image data, the 3D image data defining an image volume of voxels, a voxel being associated with a radiation intensity value or density value, the voxels defining a 3D representation of the dento-maxillofacial structure within the image volume, the dento-maxillofacial structure including a dentition; a trained deep neural network receiving the 3D image data at its input and classifying at least part of the voxels in the image volume into one or more tooth classes, preferably into at least 32 tooth classes of a dentition.

In an aspect, the invention may relate to a computer, preferably a server system, adapted to automatically taxonomize 3D image data of teeth comprising: a computer readable storage medium having computer readable program code embodied therewith, the program code including a taxonomy algorithm and a trained deep neural network, the computer readable program code; and a processor, preferably a microprocessor, coupled to the computer readable storage medium, wherein responsive to executing the first computer readable program code, the processor is configured to perform executable operations comprising: receiving 3D image data, preferably 3D cone beam CT (CBCT) image data, the 3D image data defining an image volume of voxels, a voxel being associated with a radiation intensity value or density value, the voxels defining a 3D representation of the dento-maxillofacial structure within the image volume, the dento-maxillofacial structure including a dentition; a trained deep neural network receiving the 3D image data at its input and classifying at least part of the voxels in the image volume into at least one or more tooth classes, preferably into at least 32 tooth classes of a dentition; and, determining a taxonomy of the dentition including defining candidate dentition states, each candidate state being formed by assigning a candidate label to each of the plurality of 3D image data sets on the basis of the activation values; and, evaluating the candidate states on the basis of one or more conditions, at least one of the one or more conditions requiring that different candidate tooth labels assigned different 3D image data sets.

In an aspect, the invention may relate to a computer system, preferably a server system, adapted to automatically taxonomize 3D image data of teeth comprising:
a computer readable storage medium having computer readable program code embodied therewith, the program code including a taxonomy algorithm and a trained deep neural networks, the computer readable program code; and a processor, preferably a microprocessor, coupled to the computer readable storage medium, wherein responsive to executing the first computer readable program code, the processor is configured to perform executable operations comprising: receiving 3D image data, preferably 3D cone beam CT (CBCT) image data, the 3D image data defining an image volume of voxels, a voxel being associated with a radiation intensity value or density value, the voxels defining a 3D representation of the dento-maxillofacial structure within the image volume, the dento-maxillofacial structure including a dentition; a first trained deep neural network receiving the 3D image data at its input and classifying at least part of the voxels in the image volume into at least one or more tooth classes, preferably into at least 32 tooth classes of a dentition;
a second trained deep neural network receiving the results of the first trained deep neural network and classifying subsets per individual tooth of the received voxel representations into individual labels for tooth classes; and, determining a taxonomy of the dentition including defining candidate dentition states, each candidate state being formed by assigning a candidate label to each of the plurality of 3D image data sets on the basis of the activation values; and, evaluating the candidate states on the basis of one or more conditions, at least one of the one or more conditions requiring that different candidate tooth class labels assigned different 3D image data sets.

In an aspect, the invention relates to a client apparatus, preferably a mobile client apparatus, adapted to communicate with a server system, the server system being adapted to automatically taxonomize 3D image data of teeth according to claims 10-12, the client apparatus comprising: a computer readable storage medium having computer readable program code embodied therewith, and a processor, preferably a microprocessor, coupled to the computer readable storage medium and coupled to a display apparatus, wherein responsive to executing the first computer readable program code, the processor is configured to perform executable operations comprising: transmitting 3D image data, preferably 3D cone beam CT (CBCT) image data, the 3D image data defining an image volume of voxels, a voxel being associated with a radiation intensity value or density value, the voxels defining a 3D representation of the dento-maxillofacial structure within the image volume, the dento-maxillofacial structure including a dentition; requesting the server system to segment, classify and taxonomize the 3D image data of teeth; receiving a plurality 3D image data sets, each 3D image data set defining an image volume of voxels, the voxels defining a 3D tooth model within the image volume; the plurality 3D image data sets forming the dentition; receiving one or more tooth class labels associated with the one or more 3D image data sets; and, rendering the one or more 3D image data sets and the one or more associated tooth class labels on a display.

In an aspect, the invention relates to a computer-implemented method for automated classification of 3D image data of teeth comprising: a computer receiving one or more of 3D image data sets, a 3D image data set defining an image volume of voxels, the voxels defining a 3D tooth model within the image volume, the image volume being associated with a 3D coordinate system; the computer pre-processing each of the 3D image data sets, the pre-processing including positioning and orienting each of the 3D tooth models in the image volume on the basis of the morphology of teeth, preferably the 3D shape of a teeth and/or a slice of the 3D shape; and, the computer providing each of the pre-processed 3D image data sets to the input of a trained deep neural network and the trained deep neural network classifying each of the pre-processed 3D image data sets on the basis of a plurality of candidate tooth labels of the dentition, wherein classifying a 3D image data set includes generating for each of the candidate tooth labels an activation value, an activation value associated with a candidate tooth label defining the likelihood that the 3D image data set represents a tooth type as indicated by the candidate tooth label.

In an embodiment, the pre-processing further includes: determining a longitudinal axis portion of a 3D tooth model and using the longitudinal axis portion, preferably a point on the axis portion, to position the 3D tooth model in the image volume; and, optionally, determining a center of gravity and/or a high-volume part of the 3D tooth model or a slice thereof and using the center of gravity and/or a high-volume part of the slice thereof for orienting the 3D tooth model in the image volume.

Hence, the invention may include a computer including a 3D deep neural network classifying at least one 3D image data set representing an individual 3D tooth model by assigning at least one tooth labels from a plurality of candidate tooth labels to the 3D image data set. Before being fed to the input of the 3D image data set, the 3D image data set is pre-processed by the computer in order to provide the 3D tooth model a standardized orientation in the image volume. This way, a random orientation in the image volume of the 3D tooth model is set into a uniform normalized orientation, e.g. oriented in the middle of the image volume, a longitudinal axis of the 3D tooth model parallel to the z-axis and the crown of the 3D tooth model pointing in the negative z direction and a radial axis through a center of gravity of the 3D tooth model pointing in the positive x-direction. The pre-processing on the basis of the morphology of the tooth broaches the problem that 3D deep neural networks are sensitive to rotational variations of a 3D tooth model.

In an embodiment, the computer may receive a plurality of 3D image data sets which are part of a dentition. In that case, the method may further comprise: determining a taxonomy of the dentition including: defining candidate dentition states, each candidate dentition state being formed by assigning a candidate tooth label to each of the plurality of 3D image data sets on the basis of the activation values; and, evaluating the candidate dentition states on the basis of one or more conditions, at least one of the one or more conditions requiring that different candidate tooth labels are assigned to different 3D image data sets, preferably the order in which candidate dentition states are evaluated is based on the height of the activation values associated with a candidate dentition state.

In a further aspect, the invention may relate to a computer-implemented method for automated taxonomy of 3D image data of teeth comprising: a computer receiving a plurality of 3D image data sets, a 3D image data set defining an image volume of voxels, the voxels defining a 3D tooth model within the image volume, the image volume being associated with a 3D coordinate system, the plurality of 3D image data sets being part of a dentition; the computer providing each of the 3D image data sets to the input of a trained deep neural network and the trained deep neural network classifying each of the 3D image data sets on the basis of a plurality of candidate tooth labels of the dentition, wherein classifying a 3D image data set includes generating for each of the candidate tooth labels an activation value, an activation value being associated with a candidate label defining the likelihood that the 3D image data set represents a tooth type as indicated by the candidate tooth label; and, the computer determining a taxonomy of the dentition including: defining candidate dentition states, each candidate state being formed by assigning a candidate tooth label to each of the plurality of 3D image data sets on the basis of the activation values; and, evaluating the candidate dentition states on the basis of one or more conditions, at least one of the one or more conditions requiring that different candidate tooth labels assigned different 3D image data sets.

Hence, the invention may further provide a very accurate method of providing a fully automated taxonomy of 3D image data sets forming a dentition using a trained 3D deep neural network and a post-processing method. During the post-processing, the classification results of the plurality of 3D image data sets that form a dentition, i.e. the candidate tooth labels and associated activation values for each 3D image set may be evaluated on the basis of one or more conditions in order to provide an accurate taxonomy of the dentition.

In an embodiment, determining a taxonomy of the dentition further may include: defining candidate dentition states, each candidate dentition state being formed by assigning a candidate tooth label to each of the plurality of 3D image data sets on the basis of the activation values; and, evaluating the candidate dentition states on the basis of one or more conditions, at least one of the one or more conditions requiring that different candidate tooth labels are assigned to different 3D image data sets.

In yet a further aspect, the invention relate to a computer-implemented method for automated segmentation and classification of 3D image data of teeth comprising: a computer receiving 3D image data, preferably 3D cone beam CT (CBCT) image data, the 3D image data defining an image volume of voxels, a voxel being associated with a radiation intensity value or density value, the voxels defining a 3D representation of the dento-maxillofacial structure within the image volume, the dento-maxillofacial structure including a dentition; a first trained deep neural network receiving the 3D image data at its input and classifying at least part of the voxels in the image volume into at least one of jaw, teeth and/or nerve voxels; segmenting the classified teeth voxels into a plurality 3D image data sets, each 3D image data set defining an image volume of voxels, the voxels defining a 3D tooth model within the image volume; the computer providing each of the 3D image data sets to the input of a second trained deep neural network and the second trained deep neural network classifying each of 3D image data sets on the basis of a plurality of candidate tooth labels of the dentition, wherein classifying a 3D image data set includes: generating for each of the candidate tooth labels an activation value, an activation value associated with a candidate label defining the likelihood that the 3D image data set represents a tooth type as indicated by the candidate tooth label.

The invention may also provide a method of fully automated segmentation and classification of 3D image data, e.g. a (CB)CT 3D image data set, that includes a dento-maxillofacial structure including a dentition, wherein 3D image data sets, each 3D image data set forming a 3D tooth model, are generated using a first trained deep neural network and wherein the 3D image data sets are classified by assigning tooth labels to each of the 3D image data sets.

In an embodiment, the segmenting may include: a pre-processing algorithm using the voxels to determine one or more 3D positional features of the dento-maxillofacial structure, the one or more 3D positional features being configured for input to the first deep neural network, a 3D positional feature defining position information of voxels in the image volume, the first deep neural network receiving the 3D image data and the one or more determined positional features at its input and using the one or more positional features to classify at least part of the voxels in the image volume into at least one of jaw, teeth and/or nerve voxels.

In embodiment, the position information may define a distance, preferably a perpendicular distance, between voxels in the image volume and a first dental reference plane in the image volume; a distance between voxels in the image volume and a first dental reference object in the image volume; and/or, positions of accumulated intensity values in a second reference plane of the image volume, wherein an accumulated intensity value at a point in the second reference plane includes accumulated intensity values of voxels on or in the proximity of the normal running through the point in the reference plane.

In an embodiment, the method may comprise: determining a taxonomy of the dentition including: defining candidate dentition states, each candidate state being formed by assigning a candidate tooth label to each of the plurality of 3D image data sets on the basis of the activation values; and, evaluating the candidate dentition states on the basis of one or more conditions, at least one of the one or more conditions requiring that different candidate tooth labels assigned different 3D image data sets.

In a further aspect, the invention may relate to computer system, preferably a server system, adapted to automatically classify 3D image data of teeth comprising: a computer readable storage medium having computer readable program code embodied therewith, the program code including a pre-processing algorithm and a trained deep neural network, the computer readable program code; and a processor, preferably a microprocessor, coupled to the computer readable storage medium, wherein responsive to executing the first computer readable program code, the processor is configured to perform executable operations comprising: receiving one or more of 3D image data sets, a 3D image data set defining an image volume of voxels, the voxels defining a 3D tooth model within the image volume, the image volume being associated with a 3D coordinate system; pre-processing each of the 3D image data sets, the pre-processing including: positioning and orienting each of the 3D tooth models in the image volume on the basis of the morphology of teeth, preferably the 3D shape of a tooth and/or a slice of the 3D shape; providing each of the pre-processed 3D image data sets to the input of a trained deep neural network and the trained deep neural network classifying each of the pre-processed 3D image data sets on the basis of a plurality of candidate tooth labels of the dentition, wherein classifying a 3D image data set includes generating for each of the candidate tooth labels an activation value, an activation value associated with a candidate tooth label defining the likelihood that the 3D image data set represents a tooth type as indicated by the candidate tooth label.

In yet a further aspect, the invention may relate to a computer system, preferably a server system, adapted to automatically taxonomize 3D image data of teeth comprising: a computer readable storage medium having computer readable program code embodied therewith, the program code including a taxonomy algorithm and a trained deep neural network, the computer readable program code; and a processor, preferably a microprocessor, coupled to the computer readable storage medium, wherein responsive to executing the first computer readable program code, the processor is configured to perform executable operations comprising: receiving a plurality of 3D image data sets, a 3D image data set defining an image volume of voxels, the voxels defining a 3D tooth model within the image volume, the image volume being associated with a 3D coordinate system, the plurality of 3D image data sets forming a dentition; providing each of 3D image data sets to the input of a trained deep neural network and the trained deep neural network classifying each of the 3D image data sets on the basis of a plurality of candidate tooth labels of the dentition, wherein classifying a 3D image data set includes generating for each of the candidate tooth labels an activation value, an activation value associated with a candidate label defining the likelihood that the 3D image data set represents a tooth type as indicated by the candidate tooth type label; and, determining a taxonomy of the dentition including defining candidate dentition states, each candidate state being formed by assigning a candidate label to each of the plurality of 3D image data sets on the basis of the activation values; and, evaluating the candidate states on the basis of one or more conditions, at least one of the one or more conditions requiring that different candidate tooth labels assigned different 3D image data sets.

In an aspect, the invention may relate to a computer system, preferably a server system, adapted to automatically segment and classify 3D image data of teeth comprising: a computer readable storage medium having computer readable program code embodied therewith, the program code including a segmentation algorithm and a first and second deep neural network, the computer readable program code; and a processor, preferably a microprocessor, coupled to the computer readable storage medium, wherein responsive to executing the first computer readable program code, the processor is configured to perform executable operations comprising: receiving 3D image data, preferably 3D cone beam CT (CBCT) image data, the 3D image data defining an image volume of voxels, a voxel being associated with a radiation intensity value or density value, the voxels defining a 3D representation of the dento-maxillofacial structure within the image volume, the dento-maxillofacial structure including a dentition; a first trained deep neural network receiving the 3D image data at its input and classifying at least part of the voxels in the image volume into at least one of jaw, teeth and/or nerve voxels; segmenting the classified teeth voxels into a plurality 3D image data sets, each 3D image data set defining an image volume of voxels, the voxels defining a 3D tooth model within the image volume; providing each of the 3D image data sets to the input of a second trained deep neural network and the second trained deep neural network classifying each of the pre-processed 3D image data sets on the basis of a plurality of candidate tooth labels of the dentition, wherein classifying a 3D image data set includes generating for each of the candidate tooth labels an activation value, an activation value associated with a candidate label defining the likelihood that the 3D image data set represents a tooth type as indicated by the candidate tooth type label.

In a further aspect, the invention may relate to a client apparatus, preferably a mobile client apparatus, adapted to communicate with a server system, the server system being adapted to automatically taxonomize 3D image data of teeth as described above, the client apparatus comprising: a computer readable storage medium having computer readable program code embodied therewith, and a processor, preferably a microprocessor, coupled to the computer readable storage medium and coupled to a display apparatus, wherein responsive to executing the first computer readable program code, the processor is configured to perform executable operations comprising: transmitting one or more of first 3D image data sets to the server system, a 3D image data set defining an image volume of voxels, the voxels defining a 3D tooth model within the image volume, the image volume being associated with a 3D coordinate system; requesting the server system to taxonomize the 3D image data of teeth; receiving one or more of second 3D image data sets from the server system, the one or more of second 3D image data sets being generated by the server system on the basis of the one or more first 3D image data sets, the generating including processing each of the 3D image data sets, the processing including positioning and orienting each of the 3D tooth models in the image volume on the basis of the morphology of teeth, preferably the 3D shape of a teeth and/or a slice of the 3D shape; receiving one or more tooth labels associated with the one or more second 3D image data sets respectively; and, rendering the one or more second 3D image data sets and the one or more associated tooth labels on a display.

In an aspect, the invention may relate to a client apparatus, preferably a mobile client apparatus, adapted to communicate with a server system, the server system being adapted to automatically segment and classify 3D image data of teeth according to claim 13, the client apparatus comprising: a computer readable storage medium having computer readable program code embodied therewith, and a processor, preferably a microprocessor, coupled to the computer readable storage medium and coupled to a display apparatus, wherein responsive to executing the first computer readable program code, the processor is configured to perform executable operations comprising: 3D image data, preferably 3D cone beam CT (CBCT) image data, the 3D image data defining an image volume of voxels, a voxel being associated with a radiation intensity value or density value, the voxels defining a 3D representation of the dento-maxillofacial structure within the image volume, the dento-maxillofacial structure including a dentition; requesting the server system to segment and classify the 3D image data; receiving a plurality 3D image data sets, each 3D image data set defining an image volume of voxels, the voxels defining a 3D tooth model within the image volume; the plurality 3D image data sets forming the dentition; receiving one or more tooth labels associated with the one or more 3D image data sets; and, rendering the one or more 3D image data sets and the one or more associated tooth labels on a display.

The invention may also relate of a computer program product comprising software code portions configured for, when run in the memory of a computer, executing any of the method as described above.

The invention will be further illustrated with reference to the attached drawings, which schematically will show embodiments according to the invention. It will be understood that the invention is not in any way restricted to these specific embodiments.

BRIEF DESCRIPTION OF THE DRAWINGS

FIG. 13A-13D depict examples of dento-maxillofacial features according to various embodiments of the invention;

DETAILED DESCRIPTION

Figure 1:
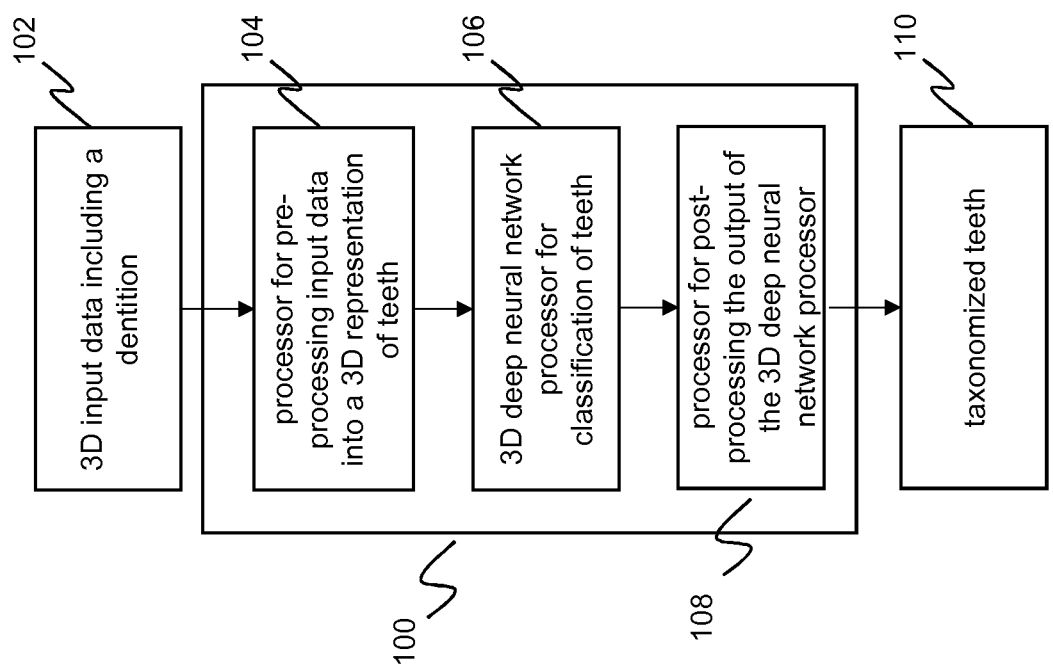
FIG. 1 depicts a high-level schematic of computer system that is configured to automatically taxonomize teeth from a dentition according to an embodiment of the invention.

In this disclosure embodiments are described of computer systems and computer-implemented methods that use deep neural networks for classifying 3D image data representing teeth. The 3D image data may comprise voxels forming a dento-maxillofacial structure comprising a dentition. For example, the 3D image data may include 3D (CB)CT image data (as generated by a (CB)CT scanner). Alternatively, the 3D image data may comprise a surface mesh of teeth (as e.g. generated by an optical 3D scanner). A computer system may comprise at least one deep neural network which is trained to classify a 3D image data set defining an image volume of voxels, wherein the voxels represent 3D tooth structures within the image volume and wherein the image volume is associated with a 3D coordinate system. The computer system may be configured to execute a training process which iteratively trains (optimizes) one or more deep neural networks on the basis of one or more training sets which may include 3D representations of tooth structures. The format of a 3D representation of an individual tooth may be optimized for input to a 3D deep neural network. The optimization may include pre-processing 3D image data, wherein the pre-processing may include determining 3D positional features. A 3D positional feature may be determined by aggregating information for the original received 3D image data as may be beneficial for accurate classification, and adding such feature to the 3D image data as a separate channel.

Once trained, the first deep neural network may receive 3D image data of a dentition and classify the voxels of the 3D image data. The output of the neural network may include different collections of voxel data, wherein each collection may represent a distinct part (e.g. individual teeth, individual nerves, sections of jaw bone) of the 3D image data. The classified voxels for individual teeth may be post-processed to reconstruct an accurate 3D representation of each classified volume.

The classified voxels or the reconstructed volume per individual tooth may additionally be post-processed to normalize orientation, dimensioning and position within a specific 3D bounding box if applicable. This reconstructed (normalized) voxel set containing the shape of an individual tooth, optionally together with its associated subset of the original received 3D image data (if applicable normalized in the same manner), may be presented to the input of a second 3D deep neural network which is trained for determining activation values associated with a set of candidate tooth labels. The second 3D deep neural network may receive 3D image data representing (part of) one individual tooth at its input, and generate at its output a single set of activations for each candidate tooth labels.

This way, two sets of classification results per individual tooth object may be identified, a first set of classification results classifying voxels into in different voxel classes (e.g. individual tooth classes, or 32 possible tooth types) generated by the first 3D deep neural network and a second set of classification results classifying a voxel representation of an individual tooth into different tooth classes (e.g. again 32 possible tooth types, or a different classification such as incisor, canine, molar, etc.) generated by the second 3D deep neural network. The plurality of tooth objects forming (part of) a dentition may finally be post-processed in order to determine the most accurate taxonomy possible, making use of the predictions resulting from the first and, optionally, second neural network, which are both adapted to classify 3D data of individual teeth.

The computer system comprising at least one trained neural network for automatically classifying a 3D image data set forming a dentition, the training of the network, the pre-processing of the 3D image data before it is fed to the neural network as well as the post-processing of results as determined by the first neural network are described hereunder in more detail.

FIG. 1 depicts a high-level schematic of a computer system that is configured to automatically taxonomize teeth in 3D image data according to an embodiment of the invention. The computer system 100 may comprise a processor for pre-processing input data 102, 3D image data associated with a dentition, into a 3D representation of teeth. The processor may derive the 3D representation 104 of the teeth from 3D image data of real-world dento-maxillofacial structures (that includes teeth and may include spatial information), wherein the 3D image data may be generated using known techniques such as a CBCT scanner or optical scans of full teeth shapes. The 3D representation of the teeth may have a 3D data format that is most beneficial as input data for 3D deep neural network processor 106, which is trained for classification of teeth. The 3D data format may be selected such that the accuracy of a set of classified teeth 110 (the output of the computer system 100) is optimized. The conversion of the input data into a 3D representation may be referred to as pre-processing the input data. The computer system may also include a processor 108 for post-processing the output of the 3D neural network processor. The post-processor may include an algorithm to correct voxels that are incorrectly classified by the first deep neural network. The post-processor may additionally include an algorithm for an additional classification of a 3D image data set representing a single tooth. The post-processor may additionally make use of a rule-based system which makes use of knowledge considering dentitions on top of the output of a deep neural network. The computer systems and its processor will be described hereunder in more detail with reference to the figures.

Figure 2:
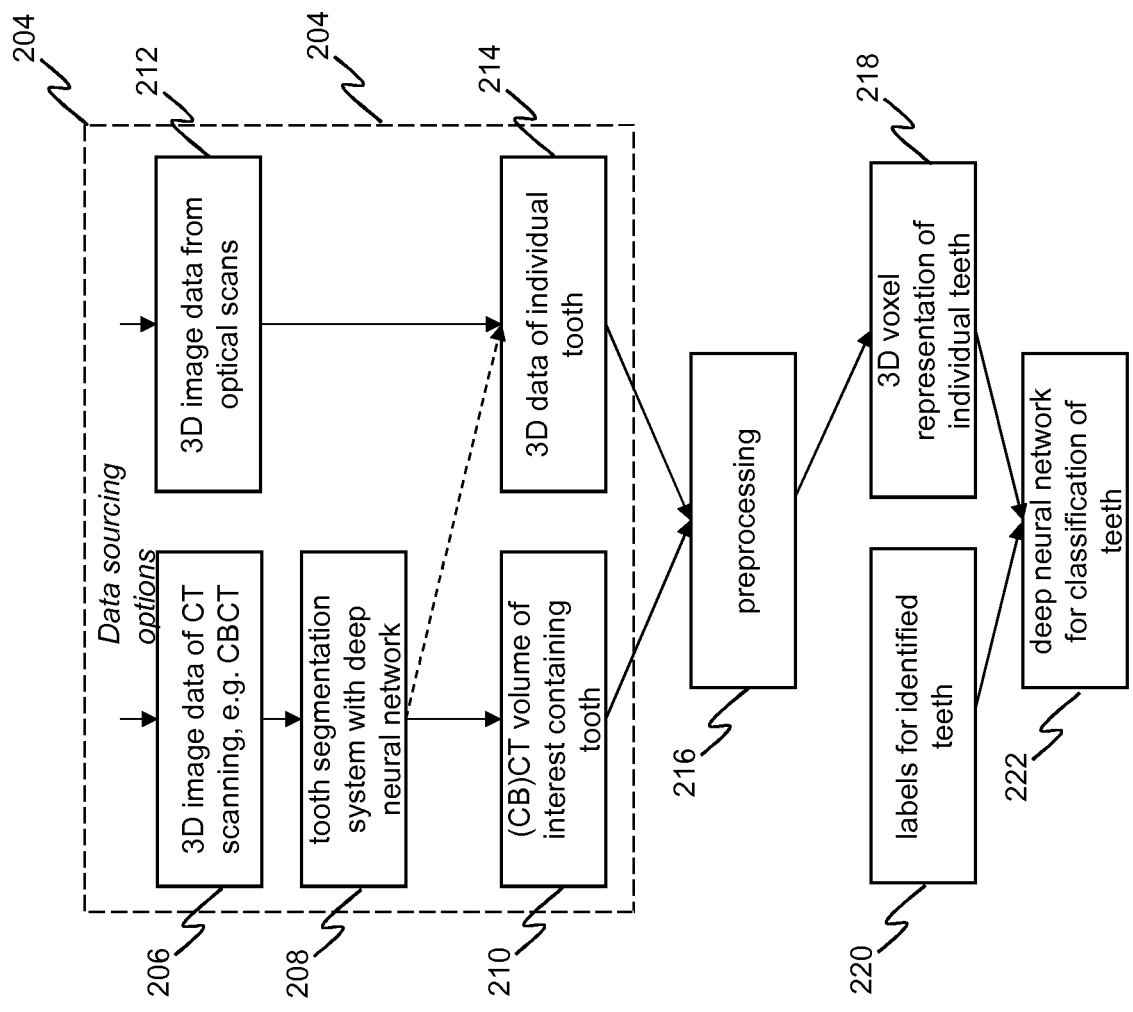
FIG. 2 depicts a flow diagram of training a deep neural network for classifying individual teeth according to an embodiment of the invention.

FIG. 2 depicts a flow diagram of training a deep neural network for classifying individual teeth according to an embodiment of the invention. In order to train the 3D deep neural network to classify a 3D representation of an individual tooth, differing sources of data may be used.

As shown in this figure, various sources 206, 212 of 3D image data 214 may be selected to train the 3D deep neural network. These data sources may require pre-processing 216. One source of 3D data may include CT 3D image data 206, in particular (CB)CT 3D image data representing a dento-maxillofacial structure include a dentition. Often, the 3D image data represents a voxel representation of a dento-maxillofacial structure including part of the jaw bone and the teeth. In that case, the system may further comprise a computer system for automatic segmenting individual teeth 208 in the 3D CT image data. Such a system may produce volume of interests (VOI) 210, wherein each VOI may comprise a volume of voxels selected from the voxels forming the complete (CB)CT scan. The selected volume of voxels may include voxels representing a tooth, including the crown and the roots. The computer system for automatic segmenting may include a 3D deep neural network processor that is trained to segment teeth in 3D image data representing a dento-maxillofacial structure. The details of the computer system for automatic segmenting a voxel representation of a dento-maxillofacial structure are described hereunder in more detail with reference to FIG. 7-17.

A further source of 3D image data of an individual tooth may be 3D image data of a complete tooth, i.e. both crown and roots, generated by an optical scanner 212. Such a scanner may generate a 3D representation of the teeth in the form of a 3D surface mesh 214. Optionally, system 208 may be configured to produce a surface mesh based on a segmented tooth.

The deep neural network that will be trained to classify individual teeth into their correctly labelled classes may require a 3D data set representing an individual tooth to be converted into a 3D data format that is optimized for a 3D deep neural network. Such optimized 3D data set increases classification accuracy as the 3D deep neural network is sensitive to intra-class variations between samples, especially variations in orientation of the 3D teeth model. To that end, a pre-processing step 216 may be used to transform the different 3D image data into a uniform 3D voxel representation 218 of individual teeth.

For each voxel representation of an individual tooth 218, a correct label 220, i.e. a label representing the tooth number (correct class or index number) of the voxel representation of the tooth, is needed to train the 3D deep learning network 222 to correctly identify the desired labels. This way the 3D deep neural network is trained to automatically classify voxel representations of the teeth. Due to the symmetric nature of a dentition, samples may be mirrored to expand the number of samples to be provided for training. Similarly, samples may be augmented by adding slightly modified versions that in 3D space have been arbitrarily rotated or stretched up to feasible limits.

Figure 3:
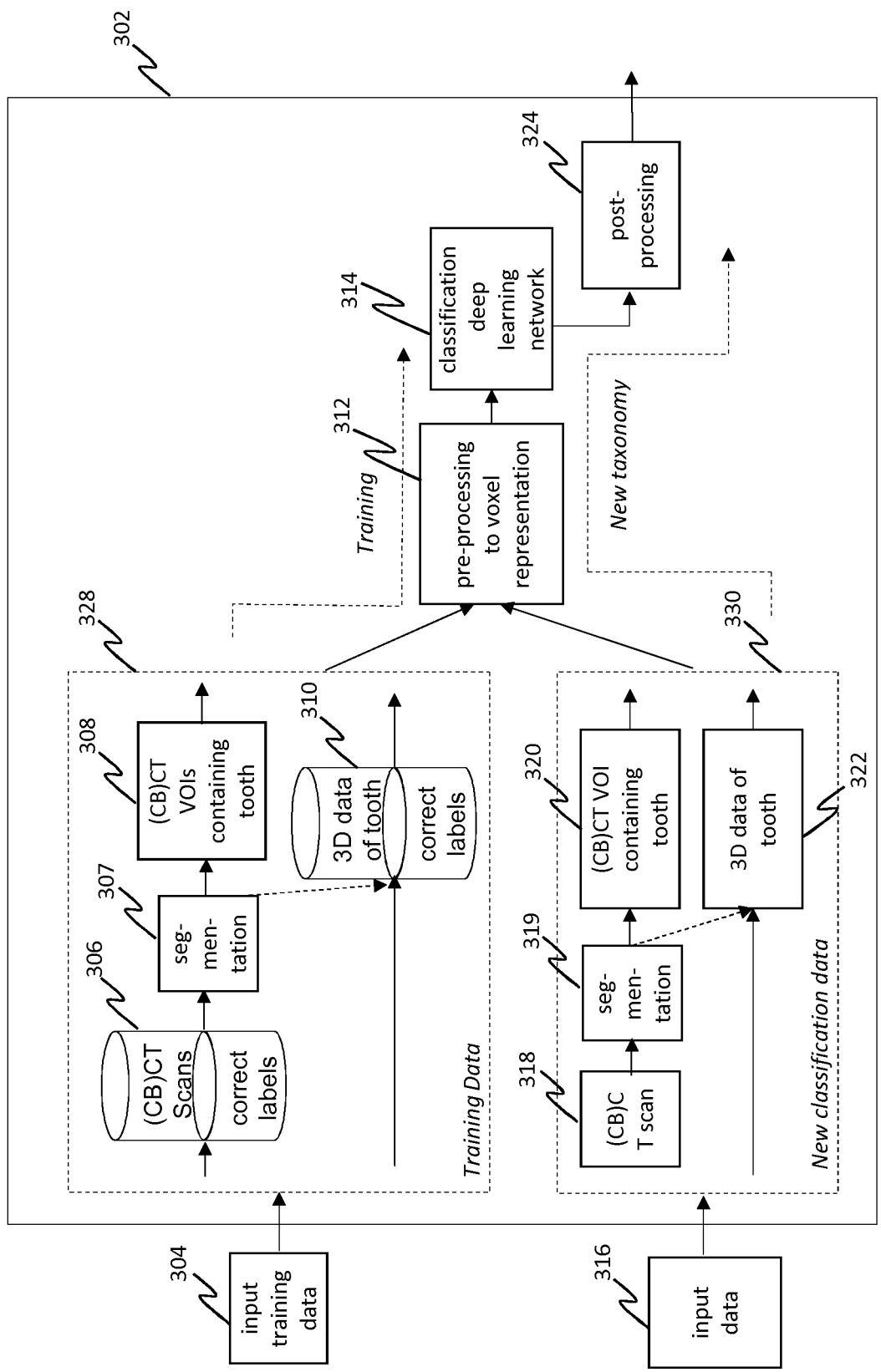
FIG. 3 depicts a computer system for taxonomizing a set of teeth from a dentition according to an embodiment of the invention.

FIG. 3. depicts a computer system for automated taxonomy of 3D teeth models according to an embodiment of the invention. The computer system may include two different modules, a first training module 328 for executing a process to train the 3D deep neural network 314 and a second classification module for executing a classification process based on new input data. As shown in FIG. 3, the training module may comprise one or more repositories or databases 306, 310 of data sources intended for training. Such repository may be sourced via an input 304 that is configured to receive input data, e.g. 3D image data including dentitions, which may be stored in various formats together with the respective desired labels. At least a first repository or database 306 may be used to store (CB)CT 3D image data of dentitions and associated labels. This database may be used by a computer system 307 to segment and extract volumes of interest 308 representing a volume of voxels comprising voxels of an individual tooth that can be used for training. In an embodiment, the computer system 307 may be configured to segment volumes of interest per individual tooth class, i.e. yielding both a volume of interest and a target label. Similarly, a second repository or database 310 may be used for storing other formats of 3D data, e.g. 3D surface meshes generated by optical scanning, and labels of individual teeth that may be employed during training of the network.

The 3D training data may be pre-processed 312 into a 3D voxel representation that is optimized for the deep neural network 314. The training process may end at this stage as the 3D deep neural network processor 314 may only require training on samples of individual teeth. In an embodiment, 3D tooth data such as a 3D surface mesh may also be determined on the basis of the segmented 3D image data that originate from (CB)CT scans.

When using the classification module 330 for classifying a new dentition 316, again multiple data formats may be employed when translating the physical dentition into a 3D representation that is optimized for the deep neural network 314. The system may make use of (CB)CT 3D image data of the dentition 318 and use a computer system 319 that is configured to segment and extract volumes of interest comprising voxels of individual teeth 320. Alternatively, another representation such as a surface meshes per tooth 322 resulting from optical scans may be used. Note again that (CB)CT data may be used to extract other 3D representations then volumes of interest.

Pre-processing 312 to the format as required for the deep neural network 314 may be put into place. The outputs of the deep neural network may be fed into a post-processing step 324 designed to make use of knowledge considering dentitions to ensure the accuracy of the taxonomy across the set of labels applied to the teeth of the dentition. In an embodiment, correct labels may be fed back into the training data with the purpose of increasing future accuracy after additional training of the deep neural network. Presentation of the results to an end-user may be facilitated by a rendering engine which is adapted to render a 3D and/or a 2D representation of the automatically classified and taxonomized 3D teeth data. Examples of rendered classified and taxonomized 3D teeth data are described with reference to FIGS. 20A and 20B.

Figure 4A:
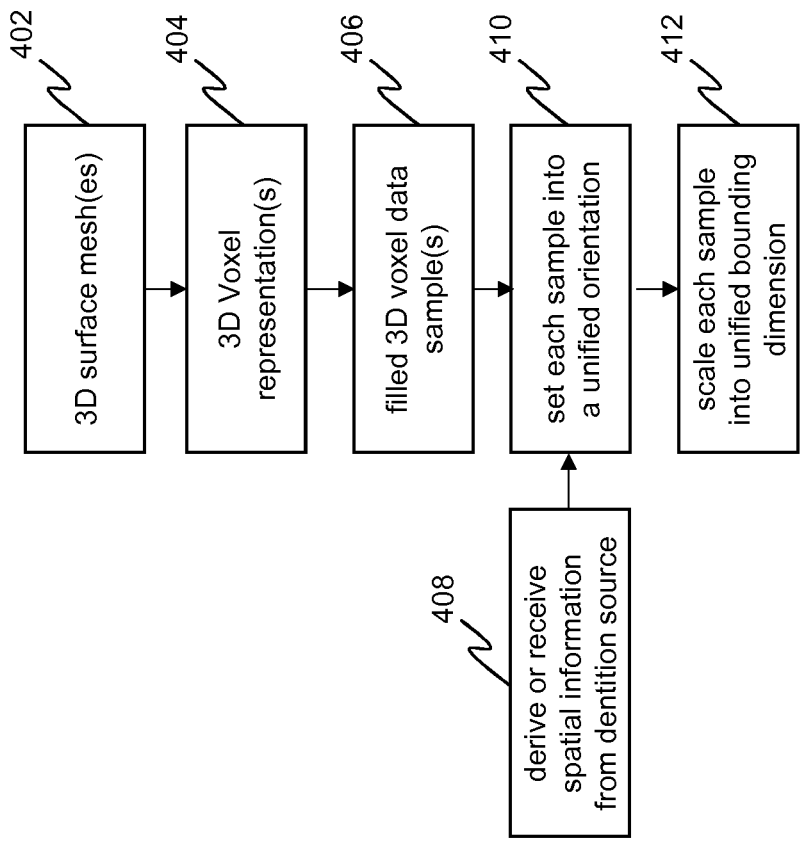
FIGS. 4A and 4B depict schematics illustrating normalization of individual tooth data according to various embodiments of the invention.
Figure 4B:
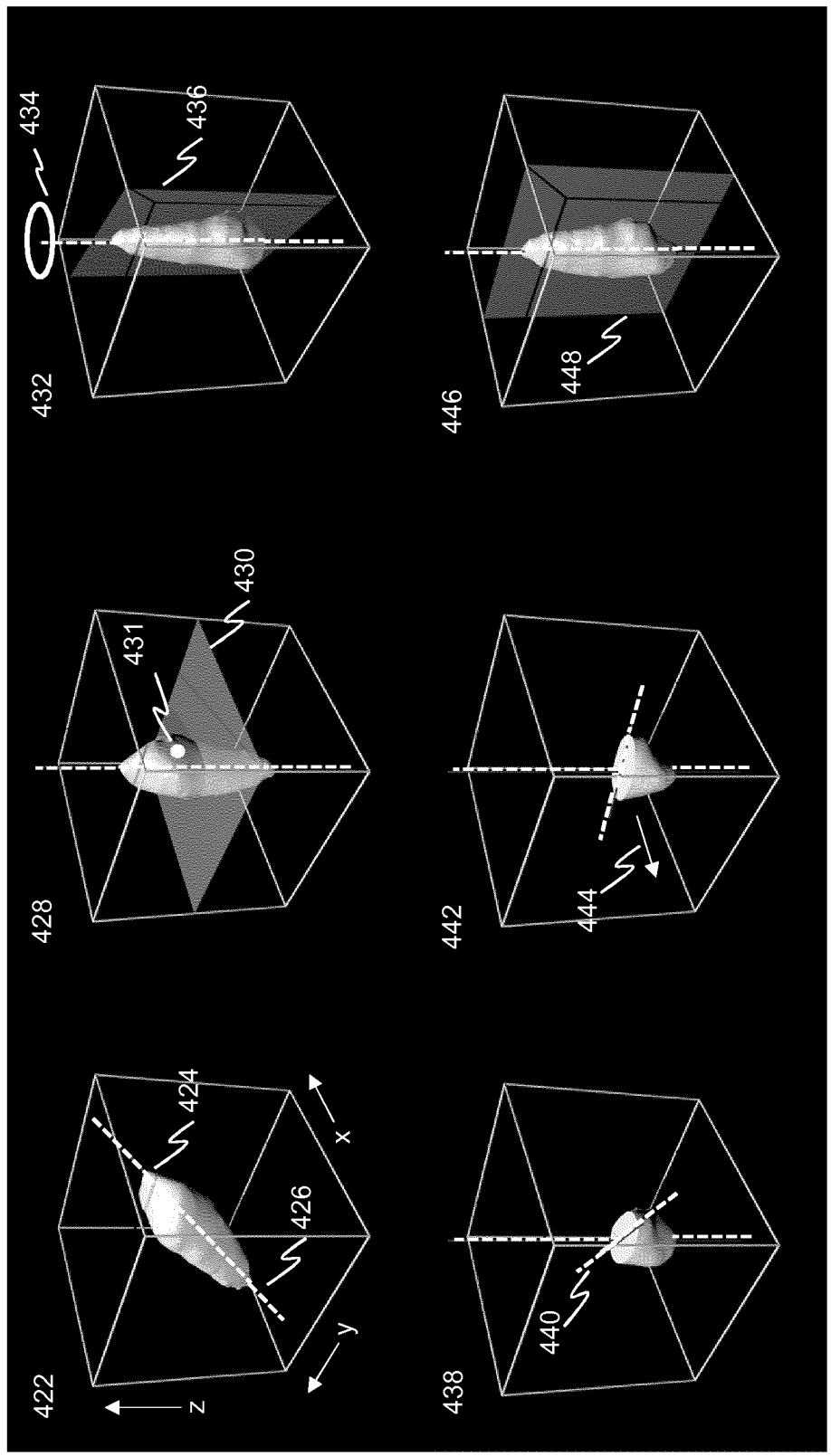

FIGS. 4A and 4B depict schematics illustrating normalization of individual tooth data according to various embodiments of the invention. In particular, FIG. 4A depicts a flow-diagram of processing 3D meshes representing the surface of a single tooth as can be derived from a dentition or from other sources. The goal of the pre-processing step is to create a 3D voxel representation of the data that is optimized for interpretation by the 3D deep neural network processor. As shown in FIG. 4A, the process may include a step of interpolating the 3D surface meshes 402 (as segmented from a dentition or from another source) into a 3D voxel representation 404. In such a step, the 3D surface meshes may be represented as a 3D volume of voxels that have a predetermined initial voxel value, e.g. a "zero" or "background" value where no tooth surface is present, and a "one" or "tooth present" value for those voxels that coincide or almost coincide with the 3D surface defined by the meshes. The thus formed 3D voxel representation thus includes a volume, e.g. a volume, e.g. a rectangular box, of voxels wherein the 3D surface of a tooth is represented by voxels within the volume that have a second voxel value and the rest of the voxels have a first voxel value. In an embodiment, the method may also include the step of setting voxels enclosed by the surface mesh to the second voxel value, so that the 3D voxel representation represents a solid object in a 3D space.

In an embodiment, a voxel representation (as might be determined by segmenting an individual tooth from e.g. a (CB)CT scan of a dentition) may also processed based on process steps 404 and further.

The (rectangular) volume of voxels may be associated with a coordinate system, e.g. a 3D Cartesian coordinate system so that the 3D voxel representation of a tooth may be associated with an orientation and dimension. The orientation and/or dimensions of the teeth models however may not be standardized. The 3D deep neural network is sensitive to the orientation of the tooth and may have difficulties classifying a tooth model that has a random orientation and non-standardized dimensions in the 3D image volume.

In order to address this problem, during the pre-processing the orientation and dimensions of the separate teeth models (the 3D voxel representations) may be normalized. What this means is that each of the 3D voxel data samples (a 3D voxel data sample representing a tooth as generated in steps 404 and/or 406), may be transformed such that the dimensions and orientation of the samples are uniform (step 410). The pre-processor may accomplish such normalized orientation and/or dimensions using spatial information from the dentition source.

The spatial information may be determined by the pre-processor by examining the dimensions and orientation of each sample in the dentition source (step 408). For example, when tooth samples of a dentition originate from a single 3D (CB)CT data stack defining a 3D image volume, the dimensions and orientation of each tooth sample can be determined by the system. Alternatively, spatial information may be provided with the individual 3D voxel representations.

The pre-processor may examine the orientation and dimensions derived from the original 3D (CB)CT data stack and if these values do not match with the desired input format for the deep learning network, a transformation may be applied. Such transformation may include a 3D rotation in order to re-orient the orientation of a sample in the 3D space (step 410) and/or a 3D scaling in order to re-scale the dimensions of a sample in the 3D space (step 412).

FIG. 4B depicts a method of normalizing the orientation and/or dimensions of tooth data according to an embodiment of the invention. In the case the original 3D image data of the teeth of a dentition do not have intra-sample consistency of dimensions and/or orientation; and/or, if the dimensions and/or orientation are unknown, various methods may be used to achieve a normalized 3D voxel representation for all samples that form the dentition.

This normalization process may use one or more transformations which rely on the morphology of a tooth: e.g. on the basis of the tooth structure a longitudinal axis may be determined, and due to the non-symmetrical shape of a tooth, Further, a position of a centre of gravity of the tooth structure may be determined, which—due to the non-symmetrical shape of the tooth—may be positioned at a distance from the longitudinal axis. Based on such information, a normalized orientation of a tooth in a 3D image space may be determined in which upside, downside, backside and front side of a tooth can be uniformly defined. Such determination of e.g. a longitudinal axes may be performed by means of principle component analysis, or by other means as described below.

As shown in FIG. 4B, the orientation and dimensions of a 3D tooth sample in a 3D image space may be based on a predetermined coordinate system. The x, y and z axis may be chosen as indicated however other choices are also possible. When assuming a completely arbitrary orientation of a 3D tooth sample 422, the rotations along two axes (x and y in this example) may be set by determining two points 424 and 426 within the sample that have the greatest distance between each other. The line between these two points may define (part of) a longitudinal axis of the tooth structure. The sample may be translated so that a predetermined point on the longitudinal axis part, e.g. the middle point, between the two points 424 and 426 may coincide with the center of the image space. Further, the sample may be rotated along the center point in such a way the longitudinal axis part is parallel with the z-axis, resulting in a reorientation of the sample (as shown in 428). Hence, this transformation defines a longitudinal axis on the basis of the shape of the tooth, uses a point (e.g. the middle) on the longitudes axis to position the tooth in the 3D image volume (e.g. in the center of the volume) and aligns the longitudinal axis to an axis e.g. the z-axis, of the coordinate system of the 3D image volume.

Further, a center of gravity 431 of the dental structure may be determined. Further, a plane 430—in this case an x-y plane, normal to the longitudinal axis of the tooth structure and positioned at the center of the longitudinal axis—may be used to determine whether most of the sample volume and/or the center of gravity is above or below the plane. A rotation may be used to ensure that most of the volume is on a selected side of the x-y plane 430, in the case of this example the sample is rotated such that the larger volume is downwards towards the negative z direction, resulting in a transformation as shown in 432. Hence, this transformation uses the volume of the tooth below and above a plane normal to the longitudinal axis of the tooth structure and/or the position of the center of gravity positioned relative to such plane in order to determine an upside and a downside of the tooth structure and to align the tooth structure to the axis accordingly. For any identical sample received in an arbitrary orientation, there would be only one aspect of the orientation that might differ after these transformation step(s), which is the rotation along the z-axis as indicated by 434.

Different ways exist for setting this rotation. In an embodiment, a plane may be used which is rotated along the center-point and the z-axis. The system may find the rotation of the plane at which the volume on one side of this plane is maximized. The determined rotation may then be used to rotate the sample such that the maximum volume is oriented in a selected direction along a selected axis. For example, as shown in 446, the amount of volume towards the positive x-direction is maximized, effectively setting the plane found for 436 parallel to a predetermined one, for example the z-y plane as shown in 448.

In a further embodiment, instead of volumes the center of gravity may be used to set the rotation. For example, the system may construct a radial axis part that runs through the center of gravity and a point on the longitudinal axis. Thereafter, a rotation along the longitudinal axis may be selected by the system such that the radial axis part is oriented in a predetermined direction, e.g. the positive x-direction.

In yet another embodiment, the 3D tooth structure may be sliced at a pre-determined point of the longitudinal axis of the tooth structure. For example, in 438 the tooth structure may be sliced at a point on the longitudinal axis which is at a predetermined distance from the bottom side of the tooth structure. This way a 2D slice of data may be determined. In this 2D slice the two points with the greatest distance from each other may be determined. The line between these points may be referred to as the lateral axis of the tooth structure. The sample may then be rotated in such a way that the lateral axis 440 is parallel to a pre-determined axis (e.g. the y-axis). This may leave two possible rotations along the longitudinal axis 434 (since there are two possibilities of line 440 being parallel to the y-axis).

Selection between these two rotations may be determined on the basis the two areas defined by the slice and the lateral axis. Thereafter, the structure may be rotated along the longitudinal axis such that the larger area is oriented towards a pre-determined direction, for example as shown in 442, towards the side of the negative x axis 444.

When considering different methods of unifying the orientation between samples, it may be beneficial for training accuracy to train separate 3D neural networks for classification of individual teeth for these different methods.

Finally, the 3D deep learning network is expecting each sample to have the same voxel amounts and resolution in each dimension. For this purpose, the pre-processing may include a step 412 of determining a volume in which each potential sample would fit and locating each sample centered into this space. It is submitted that, depending on the format of the data source, one or multiple of the steps in FIG. 4 may be omitted. As an example, when working with volumes of interest (VOIs) from a (CB)CT 3D data stack, steps 402 to 406 may be omitted.

Figure 5:
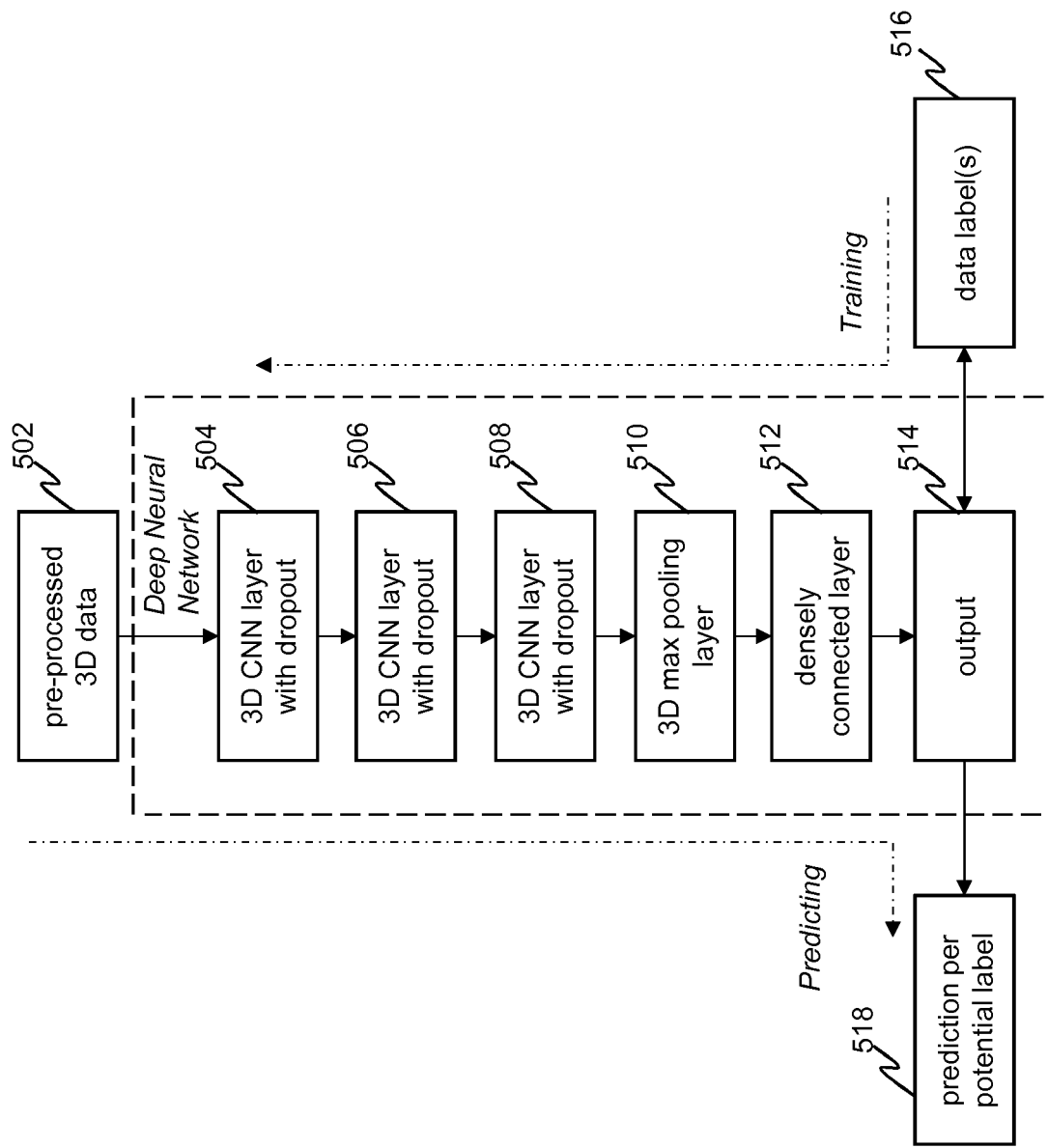
FIG. 5 depicts an example of a deep neural network architecture for classifying dentition 3D data.

FIG. 5 depicts an example of a 3D deep neural network architecture for classification of individual teeth for use in the methods and systems for automated taxonomy of 3D image data as described in this application. The network may be implemented using 3D convolutional layers (3D CNNs). The convolutions may use an activation function as known in the field. A plurality of 3D convolutional layers, 504-508, may be used wherein minor variations in the number of layers and their defining parameters, e.g. differing activation functions, kernel amounts, use of subsampling and sizes, and additional functional layers such as dropout layers and batch normalization may be used in the implementation without losing the essence of the design of the deep neural network.

In order to reduce the dimensionality of the internal representation of the data within the deep neural network, a 3D max pooling layer 510 may be employed. At this point in the network, the internal representation may be passed to a densely-connected layer 512 aimed at being an intermediate for translating the representation in the 3D space to activations of potential labels, in particular tooth-type labels. The final or output layer 514 may have the same dimensionality as the desired number of encoded labels and may be used to determine an activation value (analogous to a prediction) per potential label 518.

The network may be trained based on pre-processed 3D image data 502 (e.g. 3D voxel representations of individual teeth as described with reference to FIG. 4). In an embodiment, the 3D image data may comprise a plurality of image channels, e.g. a fourth dimension comprising additional information. Single channel 3D image data may comprise one datapoint per x, y, and z location of a voxel (e.g. density values in case of a (CB)CT scans or a binary value ("zero"/"ones") in case of binary voxel representation as described with reference to the process of FIG. 4A). In contrast, multi-channel 3D image data may include two or more different data points per voxel (comparable to e.g. colour images, which usually comprise three channels of information, one for red, one for green and one for blue). Hence, in an embodiment, a 3D deep neural network may be trained to process multi-channel 3D image data.

In an embodiment, such multi-channel 3D image data may for example comprise a first channel comprising the original 3D (CB)CT image data of an individual tooth, and a second channel containing the processed version of the same tooth as may be yielded from a method described with respect to FIG. 4A). Offering both these sets may yield information considering both the exact segmented shape (in 3D, binarily represented), as well as information from the original image (density values) as may be relevant for the classification problem. Offering both increases the potential of accurate classification.

For each sample (being a 3D representation of a single tooth) a matching representation of the correct label 516 may be used to determine a loss between desired and actual output 514. This loss may be used during training as a measure to adjust parameters within the layers of the deep neural network. Optimizer functions may be used during training to aid in the efficiency of the training effort. The network may be trained for any number of iterations until the internal parameters lead to a desired accuracy of results. When appropriately trained, an unlabeled sample may be presented as input and the deep neural network may be used to derive a prediction for each potential label.

Hence, as the deep neural network is trained to classify a 3D data sample of a tooth into one of a plurality of tooth types, e.g. 32 tooth types in case of a dentition of an adult, the output of the neural network will be activation values and associated potential tooth type labels. The potential tooth type label with the highest activation value may indicate to the system that it is most likely that the 3D data sample of a tooth represents a tooth of the type as indicated by the label. The potential tooth type label with the lowest or a relatively low activation value may indicate to the system that it is least likely that the 3D data set of a tooth represents a tooth of the type as indicated by such a label.

Figure 6:
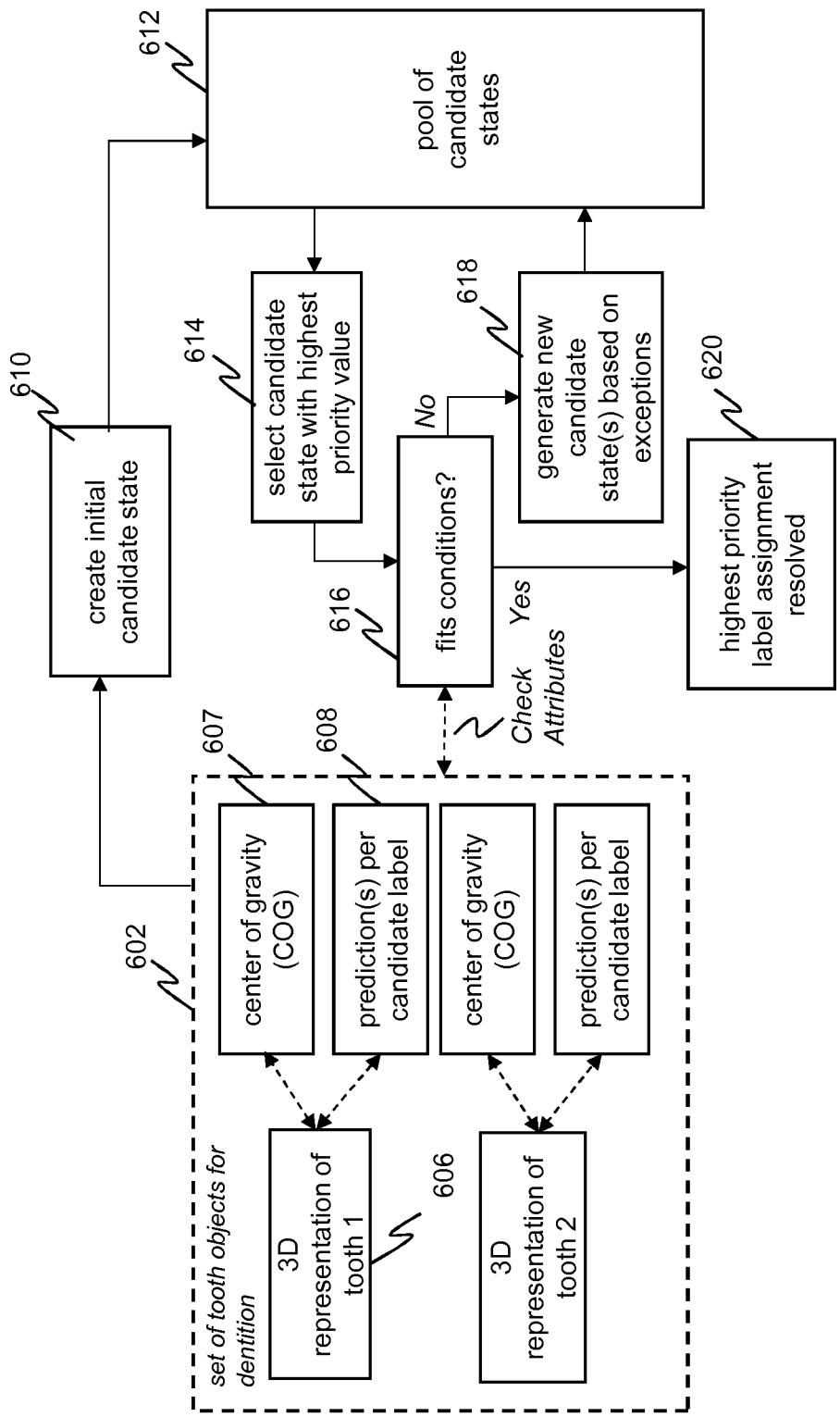
FIG. 6 depicts a flow diagram of post-processing according to an embodiment of the invention.

FIG. 6 depicts a flow-diagram of post-processing according to an embodiment of the invention. In order to make use of information available when considering a set of individual tooth objects origination for a single dentition 602 this post-processing may be utilized to determine the most feasible assignment of labels per tooth. Each 3D data set representing a tooth 606 may be processed by the deep neural network to obtain a most likely prediction value per possible candidate label 608. There may be multiple predictions per tooth object (or individual tooth 3D data set) following e.g. classification of tooth objects by multiple methods. Additionally, in some embodiments, a center of gravity (COG) 607 represented in a 3D coordinate system of 3D image data of a total dentition (e.g. 3D (CB)CT image data of a dento-maxillofacial structure that is offered to the input of a segmentation system as described with reference to FIG. 3) may be attributed to each 3D data set representing a tooth.

Candidate dentition states (or in short candidate states) may be generated wherein each 3D data set of a tooth is assigned to a candidate tooth label. An initial candidate state may be created 610 by assigning a candidate tooth label to a 3D data set of a tooth that has the highest activation value for this candidate tooth label. A candidate (dentition) state in this context may refer to a single assignment of a tooth label for each tooth object (represented e.g. by a 3D image data set) forming the dentition. This initial state may not be the desired end state as it may not satisfy the conditions needed to be met for a resolved final dentition state. The size of a state, e.g. the number of teeth present in a dentition may vary from dentition to dentition.

A priority value may be assigned to each candidate state, which may be used for determining an order in which candidate states may be evaluated. The priority values may be set by making use of desired goals to optimize a resolved optimal solution. In an embodiment, a priority value of a candidate state may be determined on the basis of the activation values, e.g. the sum of the activation values (which may be multiple per tooth object), that are assigned to the candidate labels of the candidate state. Alternatively and/or in addition, in an embodiment, a priority value may be determined on the basis of the number of uniquely assigned candidate labels and/or the number of duplicate label assignments.

The pool of candidate dentition states 612 and priority values may be stored in a memory of the computer system (wherein each candidate state may include candidate tooth labels and associated priority values).

Candidate dentition states 614 may be selected in order of the assigned priority values and evaluated in an iterative process wherein the computer may check whether predetermined conditions are met (as shown in step 616). The conditions may be based on knowledge of a dentition. For example, in an embodiment, a condition may be that a candidate label of a tooth may only occur once (uniquely) in a single candidate dentition state. Further, in some embodiments, information associated with the position of the COG for each 3D tooth data set may be used to define one or more conditions. For example, when using the FDI numbering system of adult teeth, the tooth labels with index 1x and 2x (x=1, . . . , 8) may be part of the upper jaw and tooth labels 3x and 4x (x=1, . . . , 8) may be part of the lower jaw. Here, the indices 1x, 2x, 3x, 4x (x=1, . . . , 8) define four quadrants and the teeth numbers x therein. These tooth labels may be checked on the basis of the COGs that are associated with each 3D representation of a tooth. In further embodiments, the plurality of teeth labels may be considered as an ordered arrangement of teeth of different tooth types within their jaw, yielding additional conditions considering the appropriate assignment of labels within a dentition with regard to each COG.

As another example, in an embodiment, label activations as gathered from (one of the) deep neural network(s) may be limited to a tooth type class in the form of "incisor", "canine", "molar". With a state being able to facilitate such classifications and being able to check for feasible conditions (e.g. two incisors per quadrant), the described method may be able to efficiently evaluate any condition to be satisfied.

The (order of) evaluation of the candidate states may be based on the priority values as assigned by the neural network. In particular, the resolved candidate states are optimized on the basis of the priority values. For example, when deriving the priority values from the assigned activation values of one or more deep neural networks, the final solution presented by the system 620 (i.e. the output) will be the (first) candidate dentition state that satisfies the conditions whilst having maximized assigned activation values (i.e. the sum of the activation values is maximal).

When during evaluation of a candidate dentition state, one or more conditions are not met, new candidate state(s) may be generated 618. Considering the enormous space of possible states, it would not be feasible to generate and consider all possible candidate states. Therefore, new candidate state (s) may be generated on the basis of candidate tooth labels which did not match the conditions 616. For example, in an embodiment, if a subset of 3D tooth representations of a candidate dentition state includes two or more of the same tooth labels (and thus conflicts with the condition that a dentition state should contain a set of uniquely assigned tooth labels), new candidate state(s) may be generated that attempt to resolve this particular exception. Similarly, in an embodiment, if 3D tooth representations of a candidate dentition state contain conflicting COGs, new candidate state(s) may be generated that attempt to resolve this particular exception. These new candidate state(s) may be generated stepwise, based on the original conflicting state, whilst maximizing their expected priority value. For example, in order to determine a next candidate state, for each label having an exception, the assigned (original) tooth representation(s) for the particular label in the state having (an) exception(s) may be exchanged for the representation yielding the next highest expected priority.

As described above, in some embodiments, the 3D image data may represent a dento-maxillofacial structure, including voxels related to individual sections of jaw bone, the individual teeth and the individual nerves. In those embodiments, segmentation of the dento-maxillofacial structure into separate parts is required in order to determine a 3D voxel representation of individual teeth that may be fed to the 3D deep learning network that is trained to classify individual teeth. For the purpose of tooth taxonomy, voxel representations may be generated for each of the 32 unique teeth as may be present in the healthy dentition of an adult. Hence the invention includes computer systems and computer-implemented methods that use 3D deep neural networks for classifying, segmenting and optionally 3D modelling the individual teeth of a dentition in a dento-maxillofacial structure, wherein the dento-maxillofacial structure is represented by 3D image data defined by a sequence of images forming a CT image data stack, in particular a cone beam CT (CBCT) image data stack. The 3D image data may comprise voxels forming a 3D image space of a dento-maxillofacial structure. Such computer system may comprise at least one deep neural network which is trained to classify a 3D image data stack of a dento-maxillofacial structure into voxels of different classes, wherein each class may be associated with a distinct part (e.g. individual teeth, individual jaw section jaw, individual nerves) of the structure. The computer system may be configured to execute a training process which iteratively trains (optimizes) one or more deep neural networks on the basis of one or more training sets which may include accurate 3D models of dento-maxillofacial structures. These 3D models may include optically scanned dento-maxillofacial structures.

Once trained, the deep neural network may receive a 3D image data stack of a dento-maxillofacial structure and classify the voxels of the 3D image data stack. Before the data is presented to the trained deep neural network, the data may be pre-processed so that the neural network can efficiently and accurately classify voxels. The output of the neural network may include different collections of voxel data, wherein each collection may represent a distinct part e.g. teeth or jaw bone of the 3D image data. The classified voxels may be post-processed in order to reconstruct an accurate 3D model of the dento-maxillofacial structure.

The computer system comprising a trained neural network for automatically classifying voxels of dento-maxillofacial structures, the training of the network, the pre-processing of the 3D image data before it is fed to the neural network as well as the post-processing of voxels that are classified by the neural network are described hereunder in more detail.

Figure 7:
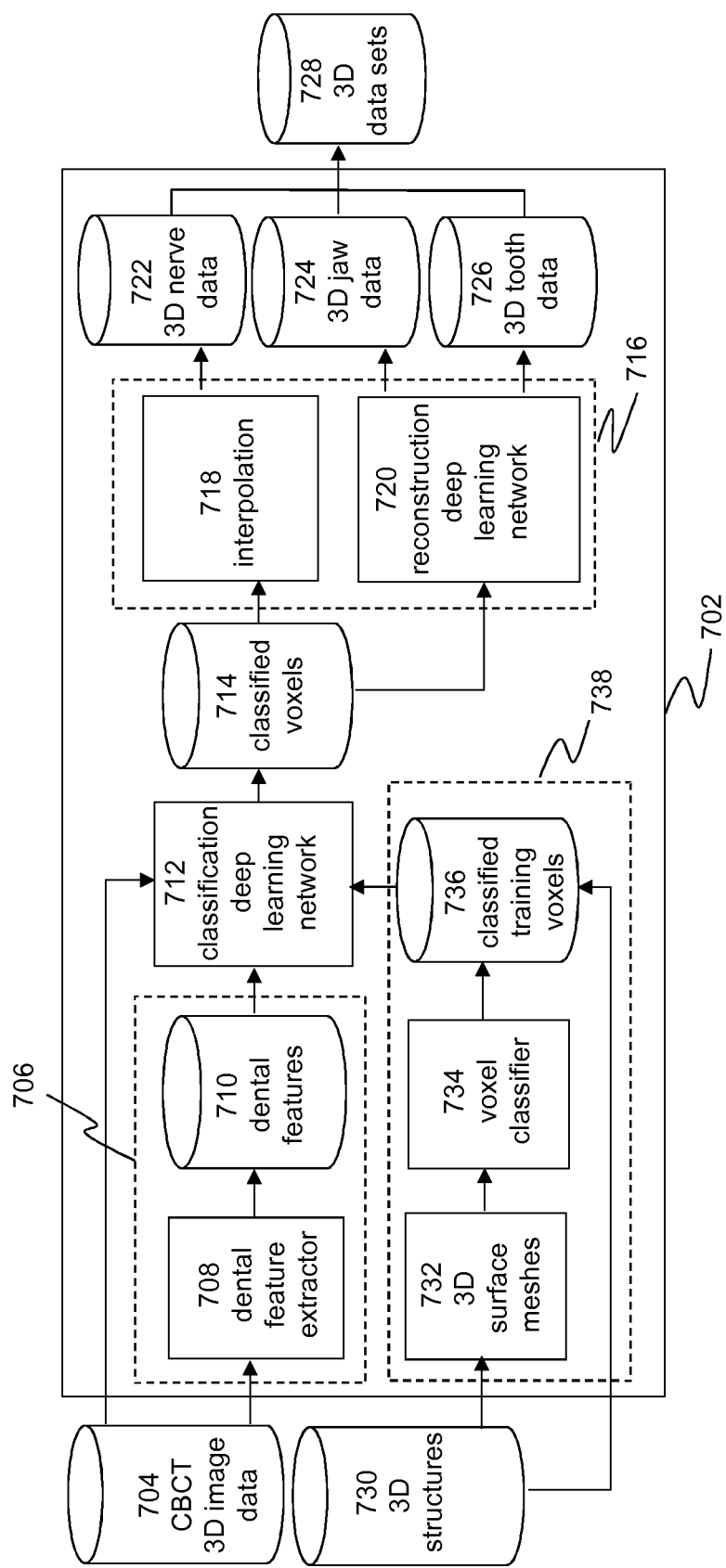
FIG. 7 schematically depicts a computer system for classification and segmentation of 3D dento-maxillofacial structures according to an embodiment of the invention.

FIG. 7 schematically depicts a computer system for classification and segmentation of 3D dento-maxillofacial structures according to an embodiment of the invention. In particular, the computer system 702 may be configured to receive a 3D image data stack 704 of a dento-maxillofacial structure. The structure may include individual jaw-, individual tooth- and individual nerve structures. The 3D image data may comprise voxels, i.e. 3D space elements associated with a voxel value, e.g. a grayscale value or a colour value, representing a radiation intensity or density value. Preferably the 3D image data stack may include a CBCT image data according a predetermined format, e.g. the DICOM format or a derivative thereof.

The computer system may comprise a pre-processor 706 for pre-processing the 3D image data before it is fed to the input of a first 3D deep learning neural network 712, which is trained to produce a 3D set of classified voxels as an output 714. As will be described hereunder in more detail, the 3D deep learning neural network may be trained according to a predetermined training scheme so that the trained neural network is capable of accurately classifying voxels in the 3D image data stack into voxels of different classes (e.g. voxels associated with individual tooth-, jaw bone and/or nerve tissue). Preferably the classes associated with individual teeth consist of all teeth as may be present in the healthy dentition of an adult, being 32 individual teeth classes. The 3D deep learning neural network may comprise a plurality of connected 3D convolutional neural network (3D CNN) layers.

The computer system may further comprise a processor 716 for accurately reconstructing 3D models of different parts of the dento-maxillofacial structure (e.g. individual tooth, jaw and nerve) using the voxels classified by the 3D deep learning neural network. As will be described hereunder in greater detail, part of the classified voxels, e.g. voxels that are classified as belonging to a tooth structure or a jaw structure are input to a further 3D deep learning neural network 720, which is trained to reconstruct 3D volumes for the dento-maxillofacial structures, e.g. the shape of the jaw 724 and the shape of a tooth 726, on the basis of the voxels that were classified to belong to such structures. Other parts of the classified voxels, e.g. voxels that were classified by the 3D deep neural network as belonging to nerves may be post-processed by using an interpolation function 718 and stored as 3D nerve data 722. The task of determining the volume representing a nerve from the classified voxels is of a nature that may currently be beyond the capacity of (the processing power available to) a deep neural network. Furthermore, the presented classified voxels might not contain the information that would be suitable for a neural network to resolve this problem. Therefore, to accurately and efficiently post-process the classified nerve voxels an interpolation of the classified voxels is used. After post-processing the 3D data of the various parts of the dento-maxillofacial structure, the nerve, jaw and tooth data 722-726 may be combined and formatted in separate 3D data sets or models 728 that accurately represent the dento-maxillofacial structures in the 3D image data that were fed to the input of the computer system.

In CBCT scans the radio density (measured in Hounsfield Units (HU)) is inaccurate because different areas in the scan appear with different greyscale values depending on their relative positions in the organ being scanned. HU measured from the same anatomical area with both CBCT and medical-grade CT scanners are not identical and are thus unreliable for determination of site-specific, radiographically-identified bone density.

Moreover, dental CBCT systems do not employ a standardized system for scaling the grey levels that represent the reconstructed density values. These values are as such arbitrary and do not allow for assessment of bone quality. In the absence of such a standardization, it is difficult to interpret the grey levels or impossible to compare the values resulting from different machines.

The teeth and jaw bone structure have similar density so that it is difficult for a computer to distinguish between voxels belonging to teeth and voxel belonging to a jaw. Additionally, CBCT systems are very sensitive for so-called beam hardening which produce dark streaks between two high attenuation objects (such as metal or bone), with surrounding bright streaks.

In order to make the 3D deep learning neural network robust against the above-mentioned problems, the 3D neural network may be trained using a module 738 to make use of 3D models of parts of the dento-maxillofacial structure as represented by the 3D image data. The 3D training data 730 may be correctly aligned to a CBCT image presented at 704 for which the associated target output is known (e.g. 3D CT image data of a dento-maxillofacial structure and an associated 3D segmented representation of the dento-maxillofacial structure). Conventional 3D training data may be obtained by manually segmenting the input data, which may represent a significant amount of work. Additionally, manual segmentation results in a low reproducibility and consistency of input data to be used.

In order to counter this problem, in an embodiment, optically produced training data 730, i.e. accurate 3D models of (parts of) dento-maxillofacial structure may be used instead or at least in addition to manually segmented training data. Dento-maxillofacial structures that are used for producing the trainings data may be scanned using a 3D optical scanner. Such optical 3D scanners are known in the art and can be used to produce high-quality 3D jaw and tooth surface data. The 3D surface data may include 3D surface meshes 732 which may be filled (determining which specific voxels are part of the volume encompassed by the mesh) and used by a voxel classifier 734. This way, the voxel classifier is able to generate high-quality classified voxels for training 736. Additionally, as mentioned above, manually classified training voxels may be used by the training module to train the network as well. The training module may use the classified training voxels as a target and associated CT training data as an input.

Additionally, during the training process, the CT training data may be pre-processed by a feature extractor 708, which may be configured to determine 3D positional features. A dento-maxillofacial feature may encode at least spatial information associated with one or more parts of the imaged dento-maxillofacial structure. For example, in an embodiment, a manually engineered 3D positional feature may include a 3D curve representing (part of) the jaw bone, in particular the dental arch, in the 3D volume that contains the voxels. One or more weight parameters may be assigned to points along the 3D curve. The value of a weight value may be used to encode a translation in the 3D space from voxel to voxel. Rather than incorporating e.g. an encoded version of the original space the image stack is received in, the space encoded is specific to the dento-maxillofacial structures as detected in the input. The feature extractor may determine one or more curves approximating one of more curves of the jaw and/or teeth (e.g. the dental arch) by examining the voxel values which represent radiation intensity or density values and fitting one or more curves (e.g. a polynomial) through certain voxels. Derivatives of (parts of) dental arch curves of a 3D CT image data stack may be stored as a positional feature mapping 710.

In another embodiment, such 3D positional features may for example be determined by means of a (trained) machine learning method such as a 3D deep neural network that is trained to derive relevant information from the entire received 3D data set.

Figure 8:
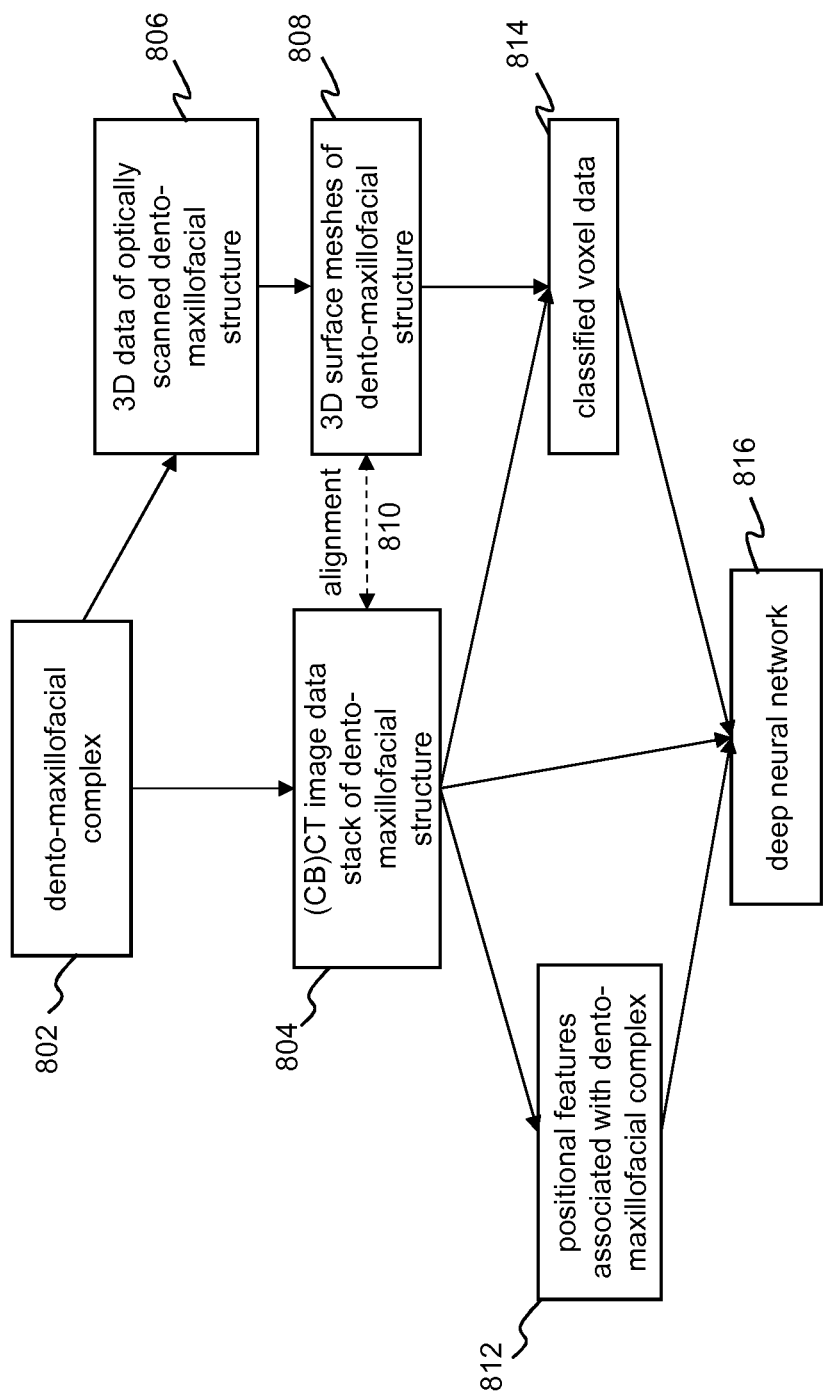
FIG. 8 depicts a flow diagram of training a deep neural network for classifying dento-maxillofacial 3D image data according to an embodiment of the invention.
Figure 9B:
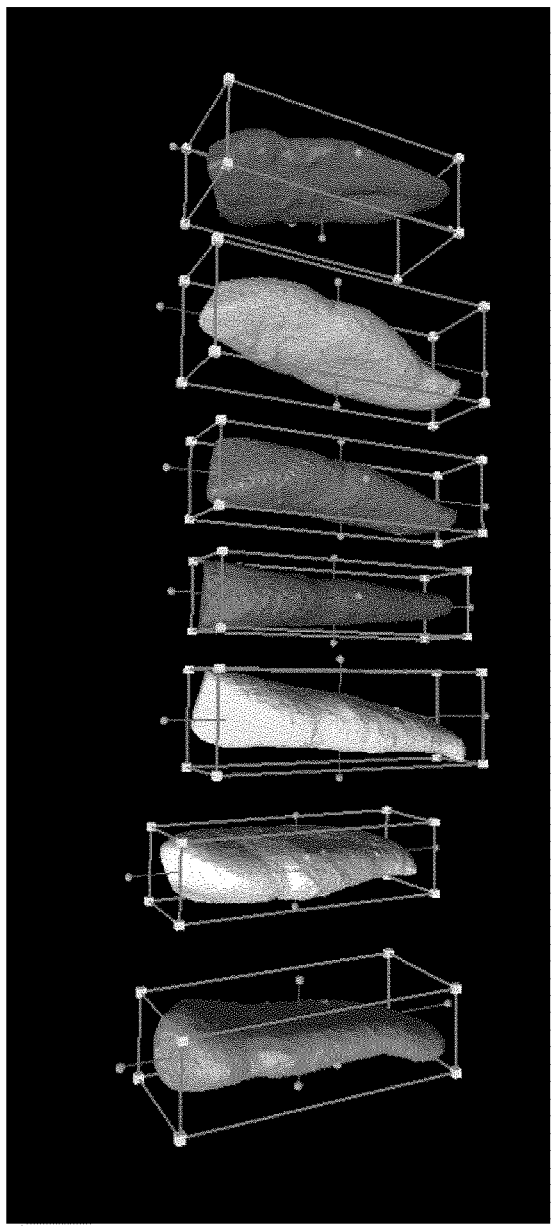
FIGS. 9A and 9B depict examples of 3D CT image data and 3D optical scanning data respectively.
Figure 9A:
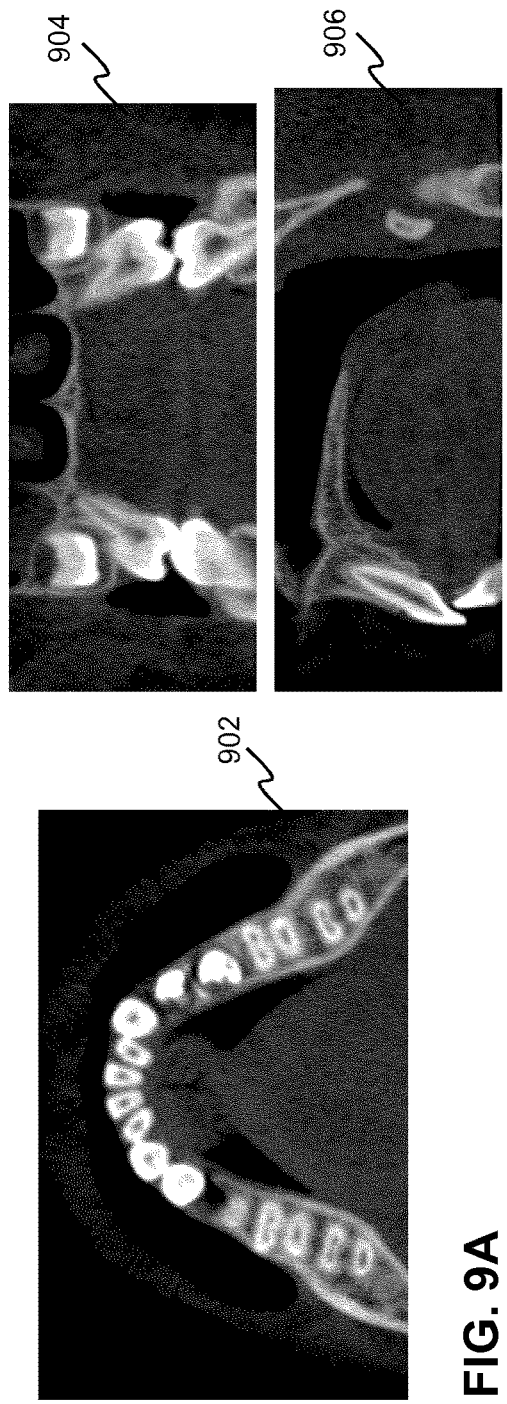

FIG. 8 depicts a flow diagram of training a deep neural network for classifying dento-maxillofacial 3D image data according to an embodiment of the invention. Training data is used in order to train a 3D deep learning neural network so that it is able to automatically classify voxels of a 3D CT scan of a dento-maxillofacial structure. As shown in this figure, a representation of a dento-maxillofacial complex 802 may be provided to the computer system. The training data may include a CT image data stack 804 of a dento-maxillofacial structure and an associated 3D model, e.g. 3D data 806 from optical scanning of the same dento-maxillofacial structure. Examples of such 3D CT image data and 3D optical scanning data are shown in FIGS. 9A and 3B. FIG. 9A depicts DICOM slices associated with different planes of a 3D CT scan of a dento-maxillofacial structure, e.g. an axial plane 902, a frontal or coronal plane 904 and the sagittal plane 906. FIG. 9B depicts 3D optical scanning data of a dento-maxillofacial structure. The computer may form 3D surface meshes 808 of the dento-maxillofacial structure on the basis of the optical scanning data. Further, an alignment function 810 may be employed which is configured to align the 3D surface meshes to the 3D CT image data. After alignment, the representations of 3D structures that are provided to the input of the computer use the same spatial coordinate system. Based on the aligned CT image data and 3D surface meshes 3D positional features 812 and classified voxel data of the optically scanned 3D model 814 may be determined. The positional features and classified voxel data may than be provided to the input of the deep neural network 816, together with the image stack 804.

Hence, during the training phase, the 3D deep learning neural network receives 3D CT training data and positional features extracted from the 3D CT training data as input data and the classified training voxels associated with the 3D CT trainings data are used as target data. An optimization method may be used to learn the optimal values of the network parameters of the deep neural network by minimizing a loss function which represents the deviation the output of the deep neural network to the target data (i.e. classified voxel data), representing the desired output for a predetermined input. When the minimization of the loss function converges to a certain value, the training process could be considered to be suitable for application.

The training process depicted in FIG. 8 using 3D positional features in combination with the training voxels, which may be (at least partly) derived from 3D optically scanning data, provides a high-quality training set for the 3D deep learning neural network. After the training process, the trained network is capable of accurately classifying voxels from a 3D CT image data stack.

Figure 10A:
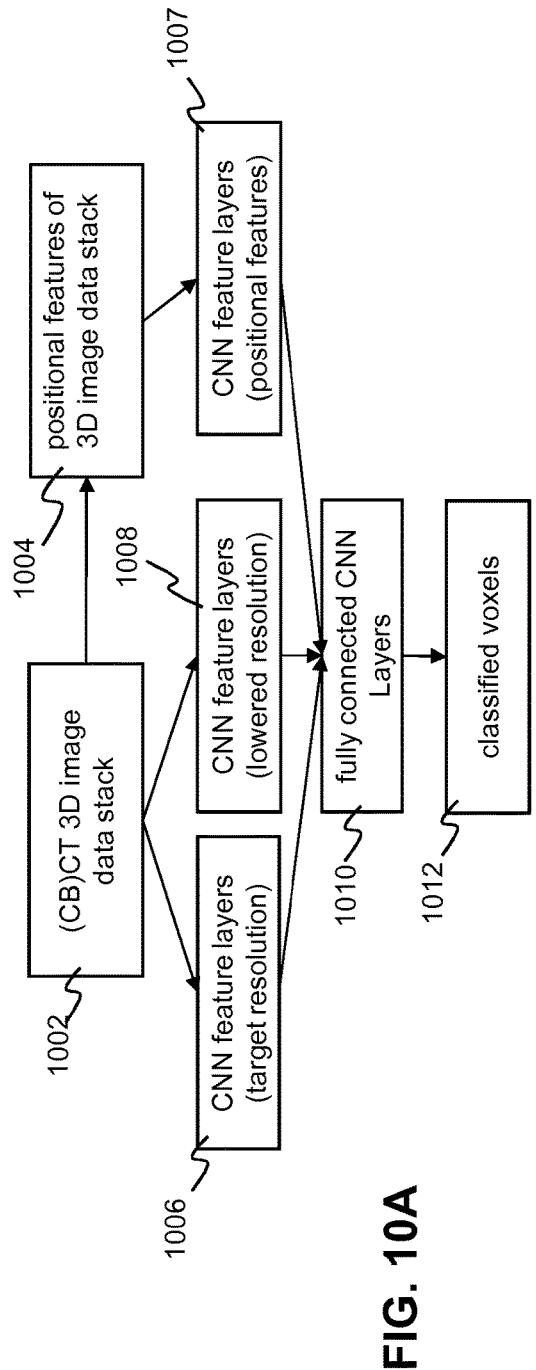
FIGS. 10A and 10B depict examples of deep neural network architectures for classifying dento-maxillofacial 3D image data.
Figure 10B:
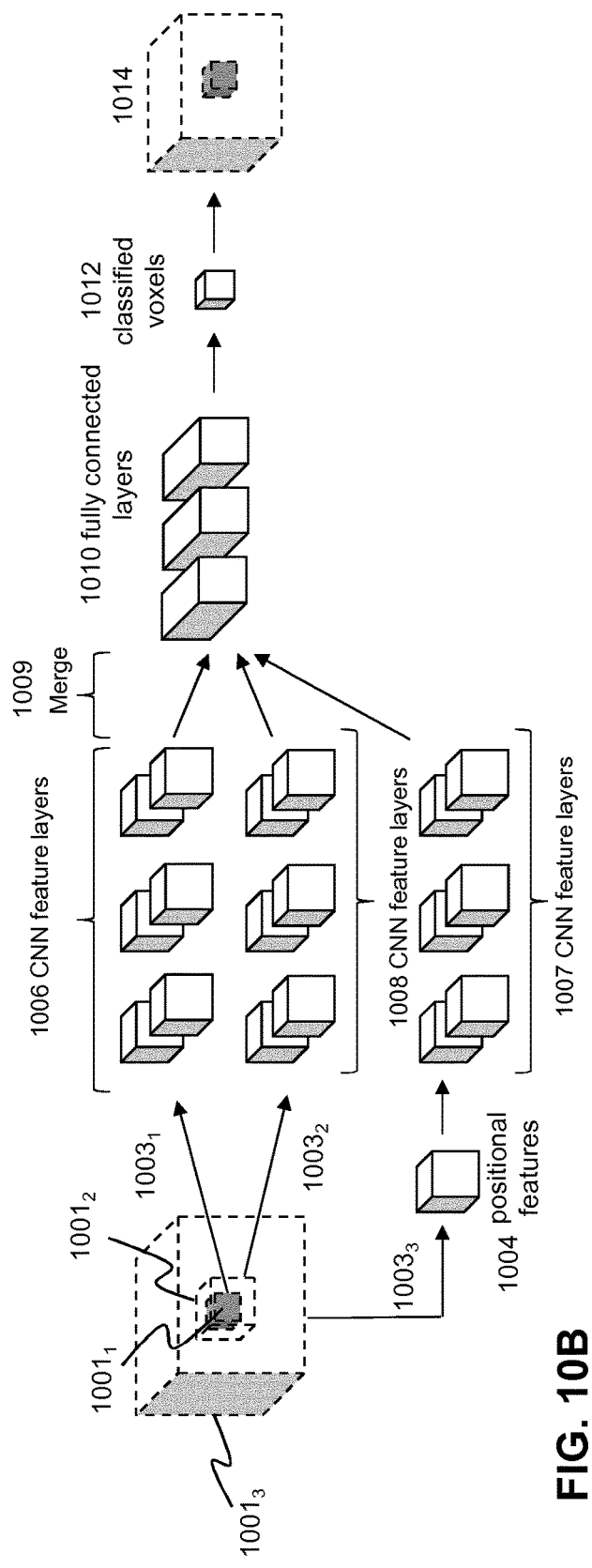

FIGS. 10A and 10B depict high-level schematics of deep neural network architectures for use in the methods and systems that are configured to classify and segment 3D voxel data of a dento-maxillofacial structure. As shown in FIG. 10A, the network may be implemented using 3D convolutional neural networks (3D CNNs). The convolutional layers may employ an activation function associated with the neurons in the layers such as a sigmoid function, tanh function, relu function, softmax function, etc. A plurality of 3D convolutional layers may be used wherein minor variations in the number of layers and their defining parameters, e.g. differing activation functions, kernel amounts and sizes, and additional functional layers such as dropout layers may be used in the implementation without losing the essence of the design of the deep neural network.

As shown in FIG. 10A, the network may include a plurality of convolutional paths, e.g. a first convolutional path associated with a first set of 3D convolutional layers 1006 and a second convolutional path associated with a second set of 3D convolutional layers 1008. The 3D image data 1002 may be fed to the inputs of both the first and second convolutional paths. As described with respect to FIG. 4, in an embodiment, the 3D image data may comprise a plurality of channels, e.g. a further fourth dimension comprising additional information such as 3D positional feature data.

Further, in some embodiments, the network may include at least a further (third) convolutional path associated with a third set of 3D convolutional layers 1007. The third convolutional path may be trained to encode 3D features derived from received 3D positional feature data associated with voxels that are offered as separate input, to the third path. This third convolution path may e.g. be used in case that such 3D positional feature information is not offered as an additional image channel of the received 3D image data.

The function of the different paths is illustrated in more detail in FIG. 10B. As shown in this figure, voxels representing the 3D image data are fed to the input of the neural network. These voxels are associated with a predetermined volume, which may be referred to as the image volume $1001_1$. Each of the subsequent 3D convolution layers of the first path $1003_1$ may perform a 3D convolution operation on first blocks of voxels $1001_1$ of the 3D image data. During the processing, the output of one 3D convolution layer is the input of a subsequent 3D convolution layer. This way, each 3D convolutional layer may generate a 3D feature map representing parts of the 3D image data that are fed to the input. A 3D convolutional layer that is configured to generate such feature maps may therefore be referred to as a 3D CNN feature layer.

As shown in FIG. 10B, the convolutional layers of the second path $1003_2$ may be configured to process second blocks of voxels $1001_2$ of the 3D image data. Each second block of voxels is associated with a first block of voxels, wherein the first and second block of voxels have the same centered origin in the image volume. The volume of the second block is larger than the volume of the first block. Moreover, the second block of voxels represents a down-sampled version of an associated first block of voxels. The down-sampling may be based using a well-known interpolation algorithm. The down-sampling factor may be any appropriate value. In an embodiment, the down-sampling factor may be selected between 20 and 2, preferably between 10 and 3.

Hence, the 3D deep neural network may comprise at least two convolutional paths. A first convolutional path $1003_1$ may define a first set of 3D CNN feature layers (e.g. 5-20 layers), which are configured to process input data (e.g. first blocks of voxels at predetermined positions in the image volume) of a first voxel resolution, e.g. the voxel resolution of the target (i.e. the resolution of the voxels of the 3D image data to be classified). Similarly, a second convolutional path may define a second set of 3D CNN feature layers (e.g. 5-20 layers), which are configured to process input data at a second voxel resolution (e.g. second blocks of voxels wherein each block of the second blocks of voxels $1001_2$ has the same center point as its associated block from the first block of voxels $1001_1$). Here, the second resolution is lower than the first resolution. Hence, the second blocks of voxels represent a larger volume in real-world dimensions than the first blocks. This way, the first 3D CNN feature layers process first blocks of voxels for in order to generate 3D feature maps and the second 3D CNN feature layers process second blocks of voxels in order to generate 3D feature maps that include information about the (direct) neighborhood of associated first blocks of voxels that are processed by the first 3D CNN feature layers.

The second path thus enables the neural network to determine contextual information, i.e. information about the context (e.g. its surroundings) of voxels of the 3D image data that are presented to the input of the neural network. By using multiple (parallel) convolutional paths, both the 3D image data (the input data) and the contextual information about voxels of the 3D image data can be processed in parallel. The contextual information is important for classifying dento-maxillofacial structures, which typically include closely packed dental structures that are difficult to distinguish. Especially in the context of classifying individual teeth, it is important that, at least, both the information at the native resolution of the input is available (containing at least detailed information considering individual tooth shape), as well as contextual information (containing at least information considering location in a dentition, neighboring structures such as other teeth, tissue, air, bone, etc.).

In an embodiment, a third convolutional path may be used for processing 3D positional features. In an alternative embodiment, instead of using a third convolutional path for processing 3D positional features, the 3D positional information, including 3D positional features, may be associated with the 3D image data that is offered to the input of the deep neural network. In particular, a 3D data stack may be formed in which each voxel is associated with an intensity value and positional information. Thus, the positional information may be paired per applicable received voxel, e.g. by means of adding the 3D positional feature information as additional channels to the received 3D image information. Hence, in this embodiment, a voxel of a voxel representation of a 3D dento-maxillofacial structure at the input of the deep neural network may not only be associated with a voxel value representing e.g. a radio intensity value, but also with 3D positional information. Thus, in this embodiment, during the training of the convolutional layers of the first and second convolutional path both, information derived from both 3D image features and 3D positional features may be encoded in these convolutional layers. The output of the sets of 3D CNN feature layers are then merged and fed to the input of a set of fully connected 3D CNN layers 1010, which are trained to derive the intended classification of voxels 1012 that are offered at the input of the neural network and processed by the 3D CNN feature layers.

The fully connected layers may be configured in such a way that they are fully connected considering the connections per to be derived output voxel in a block of output voxels. This means that they may be applied in a fully convolutional manner as is known in the art, i.e. the set of parameters associated with the fully connected layers is the same for each output voxel. This may lead to each output voxel in a block of voxels being both trained on and being inferred in parallel. Such configuration of the fully connected layers reduces the amount of parameters required for the network (compared to fully densely connected layers for an entire block), while at the same time reducing both training and inference time (a set or block of voxels is processed in one pass, instead of just a single output voxel).

The sets of 3D CNN feature layers may be trained (through their learnable parameters) to derive and pass on the optimally useful information that can be determined from their specific input, the fully connected layers encode parameters that will determine the way the information from the three previous paths should be combined to provide optimal classified voxels 1012. Thereafter, classified voxels may be presented in the image space 1014. Hence, the output of the neural network are classified voxels in an image space that corresponds to the image space of the voxels at the input.

Here, the output (the last layer) of the fully connected layers may provide a plurality of activations for each voxel. Such a voxel activation may represent a probability measure (a prediction) defining the probability that a voxel belongs to one of a plurality of classes, e.g. dental structure classes, e.g. an individual tooth, jaw section and/or nerve structure. For each voxel, voxel activations associated with different dental structures may be thresholded in order to obtain a classified voxel.

Figure 11:
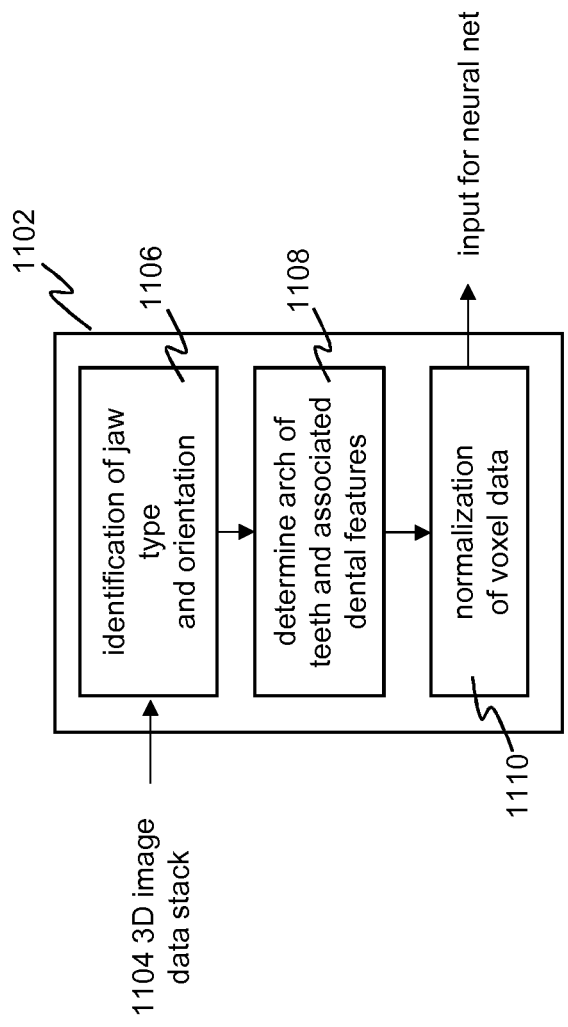
FIG. 11 illustrates a flow diagram of a method of determining dento-maxillofacial features in a 3D image data stack according to an embodiment of the invention.
Figure 12:
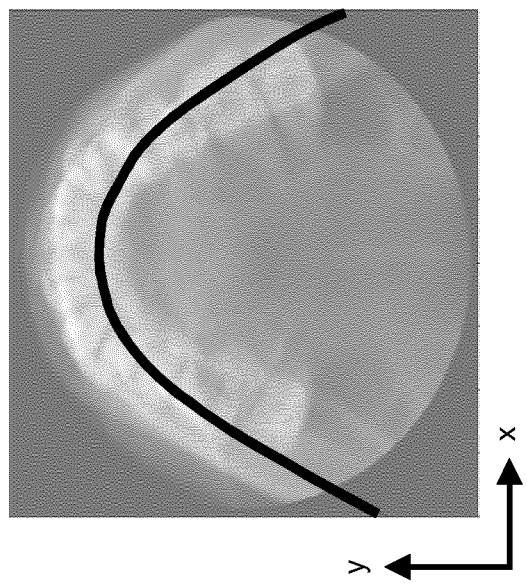
FIG. 12 provides a visualization containing the summed voxel values from a 3D image stack and a curve fitted to voxels representing a dento-maxillofacial arch.

FIG. 11-13 illustrate methods of determining 3D positional features in a 3D image data stack representing a 3D dento-maxillofacial structure and examples of such positional features. Specifically, in the case of manually engineered features, and as described with reference to FIG. 7, both the 3D image data stack and the associated 3D positional features are offered as input to the deep neural network so that the network can accurately classify the voxels without the risk of overfitting. In an embodiment, this information may be added to the 3D image data on an additional image channel. In an alternative embodiment, this information may be presented to a separate input of such 3D deep neural network. A conversion based on real-world dimensions ensures comparable input irrespective of input image resolution. A manually engineered positional feature may provide the 3D deep neural network information about positions of voxels in the image volume relative to a reference plane or a reference object in the image volume. For example, in an embodiment, a reference plane may be an axial plane in the image volume separating voxels associated with the upper jaw and voxels with the lower jaw. In another embodiment, a reference object may include a curve, e.g. a 3D curve, approximating at least part of a dental arch of teeth in the 3D image data of the dento-maxillofacial structure. This way, the positional features provide the first deep neural network the means to encode abstractions indicating a likelihood per voxel associated jaw, teeth and/or nerve tissues in different positions in the image volume. These positional features may help the deep neural network to efficiently and accurately classify voxels of a 3D image data stack and are designed to reduce the risk of overfitting.

In order to determine reference planes and/or reference objects in the image volume that are useful in the classification process, the feature analysis function may determine voxels of a predetermined intensity value or above or below a predetermined intensity value. For example, voxels associated with bright intensity values may relate to teeth and/or jaw tissue. This way, information about the position of the teeth and/or jaw and the orientation (e.g. a rotational angle) in the image volume may be determined by the computer. If the feature analysis function determines that the rotation angle is larger than a predetermined amount (e.g. larger than 15 degrees), the function may correct the rotation angle to zero as this is more beneficial for accurate results.

FIG. 11 illustrates an example of a flow diagram 1102 of a method of determining manually engineered 3D positional features in a 3D image data 1104, e.g. a 3D CT image data stack. This process may include determining one or more 3D positional features of the dento-maxillofacial structure, wherein one or more 3D positional features being configured for input to specific path of the deep neural network (as discussed with reference to FIG. 10B above). A manually engineered 3D positional feature defines position information of voxels in the image volume with respect to reference planes or reference objects in the image volume, for example, a distance, e.g. a perpendicular distance, between voxels in the image volume and a reference plane in the image volume which separates the upper jaw from the low jaw. It may also define distance between voxels in the image volume and a dental reference object, e.g. a dental arch in the image volume. It may further define positions of accumulated intensity values in a second reference plane of the image volume, an accumulated intensity value at a point in the second reference plane including accumulated intensity values of voxels on or in the proximity of the normal running through the point in the reference plane. Examples of 3D positional features are described hereunder.

In order to determine a reference object that provides positional information of the dental arch in the 3D image data of the dento-maxillofacial structure. A fitting algorithm may be used to determine a curve, e.g. a curve that follows a polynomial formula, that fits predetermined points in a cloud of points of different (accumulated) intensity values.

In an embodiment, a cloud of points of intensity values in an axial plane (an xy plane) of the image volume may be determined. An accumulated intensity value of a point in such axial plane may be determined by summing voxel values of voxels positioned on the normal that runs through a point in the axial plane. The thus obtained intensity values in the axial plane may be used to find a curve that approximates a dental arch of the teeth.

An example a reference object for use in determination of manually engineered 3D positional features, in this case a curve that approximates such a dental arch is provided in FIG. 12. In this example, a cloud of points in the axial (xy) plane indicates areas of high intensity values (bright white areas) may indicate areas of teeth or jaw structures. In order to determine a dental arch curve, the computer may determine areas in an axial plane of the image volume associated with bright voxels (e.g. voxels having an intensity value above a predetermine threshold value) which may be identified as teeth or jaw voxels. These areas of high intensity may be used to determine a crescent arrangement of bright areas that approximates the dento-maxillofacial arch. This way, a dental arch curve may be determined, which approximates an average of the dento-maxillofacial arches of the upper jaw and the lower jaw respectively. In another embodiment, separate dental arch curves associated with the upper and low jaw may be determined.

Different features may be defined on basis of a curve (or FIG. 13A-13D depict examples of positional features of 3D image data according to various embodiments of the invention.

FIG. 13A depicts (left) an image of a slice of the sagittal plane of a 3D image data stack and (right) an associated visualization of a so-called height-feature of the same slice. Such height feature may encode a z-position (a height 1304) of each voxel in the image volume of the 3D CT image data stack relative to a reference plane 1302. The reference plane (e.g. the axial or xy plane which is determined to be (the best approximation of) the xy plane with approximately equal distance to both the upper jaw and the lower jaw and their constituent teeth.

Other 3D positional features may be defined to encode spatial information in an xy space of a 3D image data stack. In an embodiment, such positional feature may be based on a curve which approximates (part of) the dental arch. Such a positional feature is illustrated in FIG. 13B, which depicts (left) a slice from an 3D image data stack and (right) a visualization of the so-called travel-feature for the same slice. This travel-feature is based on the curve that approximates the dental arch 1306 and defines the relative distance 1308 measured along the curve. Here, zero distance may be defined as the point 1310 on the curve where the derivative of the second-degree polynomial is (approximately) zero. The travelled distance increases when moving in either direction on the x-axis, from this point (e.g. the point where the derivative is zero).

A further 3D positional feature based on the dental arch curve may define the shortest (perpendicular) distance of each voxel in the image volume to the dental arch curve 1306. This positional feature may therefore be referred to as the 'distance-feature'. An example of such feature is provided in FIG. 13C, which depicts (left) a slice from the 3D image data stack and (right) a visualization of the distance-feature for the same slice. For this feature, zero distance means that the voxel is positioned on the dental arch curve 1308.

Yet a further 3D positional feature may define positional information of individual teeth. An example of such feature (which may also be referred to as a dental feature) is provided in FIG. 13D, which depicts (left) a slice from the 3D image data stack and (right) a visualization of the dental feature for the same slice. The dental feature may provide information to be used for determining the likelihood to find voxels of certain teeth at a certain position in the voxel space. This feature may, following a determined reference plane such as 1302, encode a separate sum of voxels over the normal to any plane (e.g. the xy plane or any other plane). This information thus provides the neural network with a 'view' of all information from the original space as summed over the plane normal. This view is larger than would be processed when excluding this feature and may provide a means of differentiating whether a hard structure is present based on all information in the chosen direction of the space (as illustrated in $1312_{1,2}$ for the xy plane).

Hence, FIG. 11-13 show that a 3D positional feature defines information about voxels of a voxel representation that are provided to the input of a deep neural network that is trained to classify voxels. The information may be aggregated from all (or a substantial part of) the information available from the voxel representation wherein during the aggregation the position of a voxel relative to a dental reference object may be taken into account. Further, the information being aggregated such that it can be processed per position of a voxel in the first voxel representation.

Figure 14B:
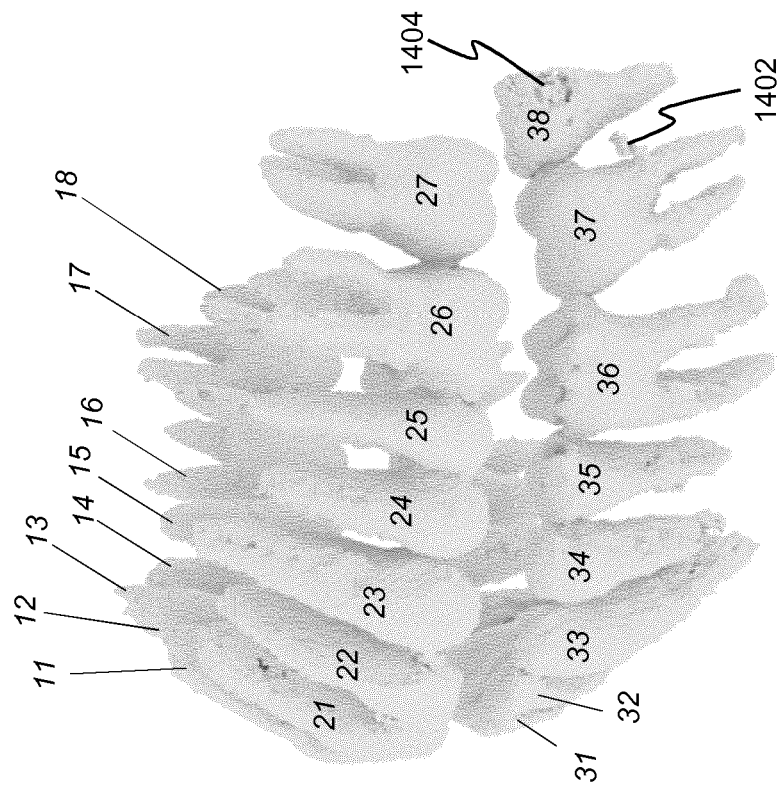
FIG. 14A-14D depict examples of the output of a trained deep learning neural network according to an embodiment of the invention.
Figure 14A:
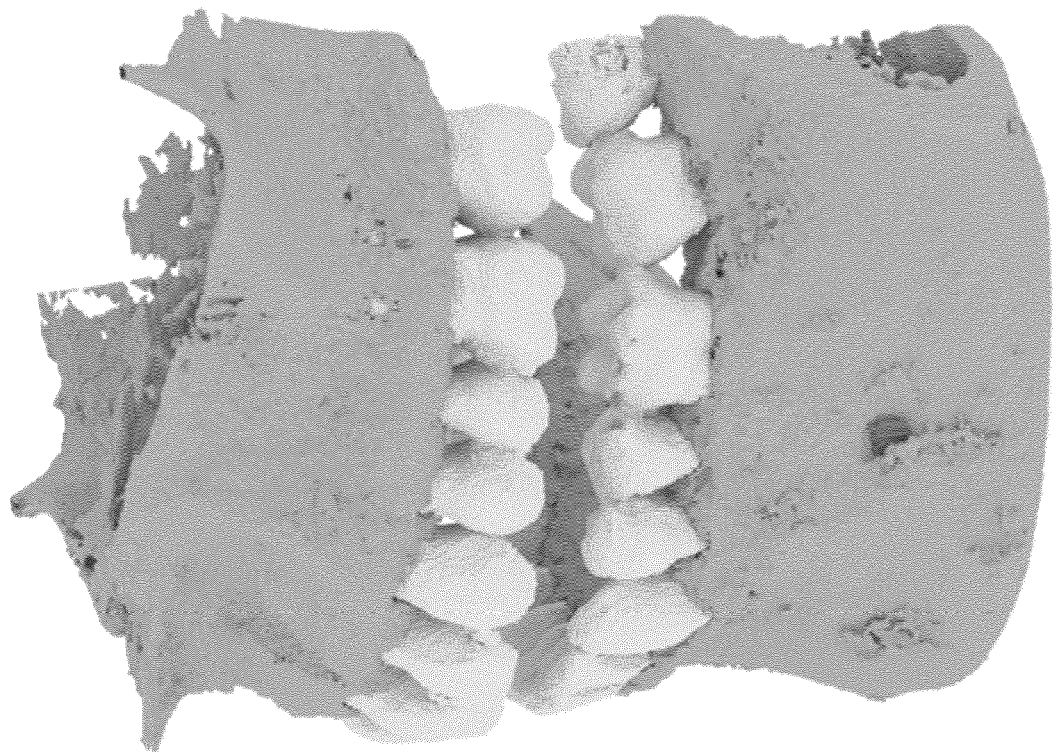
Figures 14C, 14D:
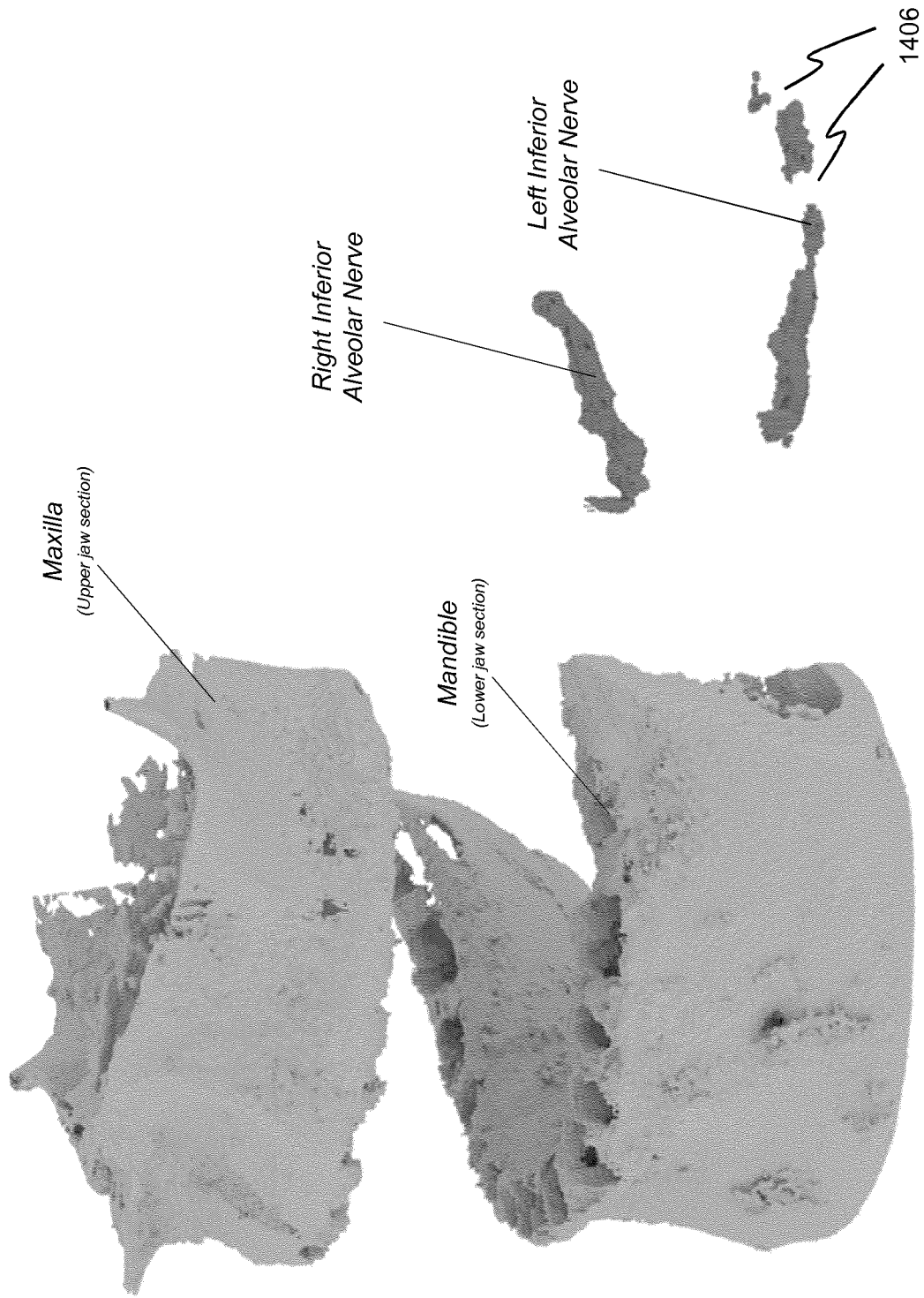

FIG. 14A-14D depict examples of the output of a trained deep learning neural network according to an embodiment of the invention. In particular, FIG. 14A-14D depict 3D images of voxels that are classified using a deep learning neural network that is trained using a training method as described with reference to FIG. 8. FIG. 14A depicts a 3D computer render (rendering) of the voxels that the deep learning neural network has classified as individual teeth, individual jaw and nerve tissue. Voxels may be classified by the neural network in voxels belonging to individual teeth structures FIG. 14B, individual jaw structures FIG. 14C or nerve structures FIG. 14D. Individual voxel representations of structures, as resulting from the deep neural network, have been marked as such within the figures. For example, FIG. 14B shows the individual tooth structures that were output, here labelled with their FDI tooth label index. (Index labels 4x, of quadrant four, have been omitted for clarity of the figure) As shown by FIG. 14B-14D, the classification process is accurate but there are still quite a number of voxels that are missed or that are wrongly classified. For example, the voxels that have been classified as FDI tooth index label 37 contain a structural extension 1402 that doesn't accurately represent the real-world tooth structure. Similarly, the voxels classified as FDI tooth index label 38 yield a surface imperfection 1404. Note though that the network has classified the vast majority of voxels for this tooth, despite being only partially present in the received 3D image data set. As shown in FIG. 14D, this such problems may be even more pronounced with classified nerve voxels, which are lacking parts 1406 present in the real-world nerve.

Figure 15:
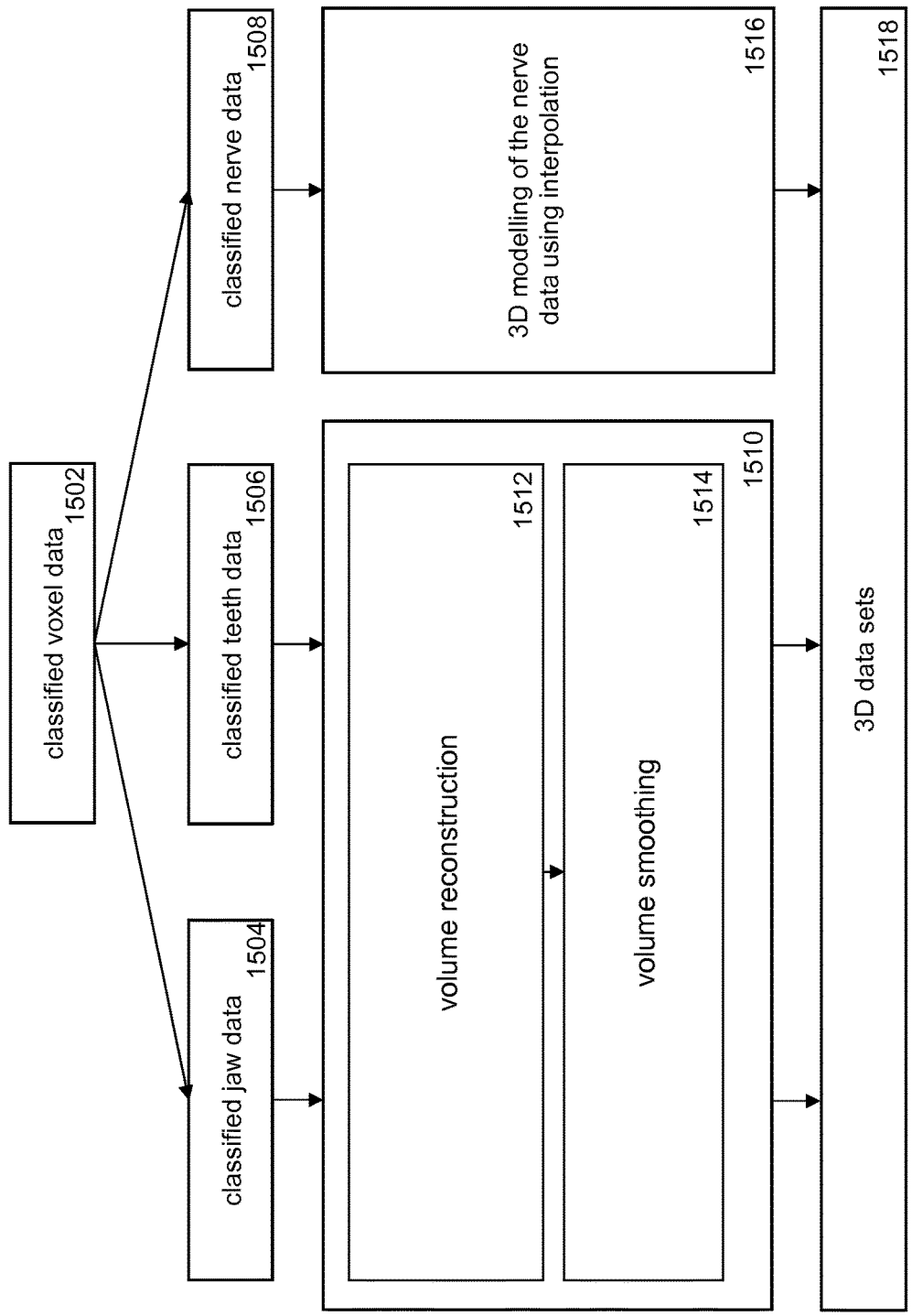
FIG. 15 depicts a flow-diagram of post-processing classified voxels of 3D dento-maxillofacial structures according to an embodiment of the invention.

In order to address the problem of outliers in the classified voxels (which form the output of the first deep learning neural network), the voxels may be post-processed. FIG. 15 depicts a flow-diagram of post-processing classified voxels of 3D dento-maxillofacial structures according to an embodiment of the invention. In particular, FIG. 15 depicts a flow diagram of post-processing voxel data of dento-maxillofacial structures that are classified using a deep learning neural network as described with reference to FIG. 7-14 of this application.

As shown in FIG. 15 the process may include a step of dividing the classified voxel data 1502 of the 3D dento-maxillofacial structure into voxels that are classified as individual jaw voxels 1504, individual teeth voxels 1506 and voxels that are classified as nerve data 1508. As will be described hereunder in more detail, the jaw and teeth voxels may be post-processed using a further, second deep learning neural network 1510. In contrast to the initial first deep learning neural network (which uses at least a 3D CT image data stack of a dento-maxillofacial structure as input), which generates the best possible voxel classification based on the image data, the second 'post processing' deep learning neural network translates parts of the output of the first deep learning neural network to voxels so that the output more closely matches the desired 3D structures.

The post-processing deep learning neural network encodes representations of both classified teeth and jaw (sections). During the training of the post-processing deep learning neural network, the parameters of the neural network are tuned such that the output of the first deep learning neural network is translated to the most feasible 3D representation of these dento-maxillofacial structures. This way, imperfections in the classified voxels can be reconstructed 1512. Additionally, the surface of the 3D structures may be smoothed 1514 so that the best feasible 3D representation may be generated. In an embodiment, omitting the 3D CT image data stack from being an information source for the post processing neural network makes this post processing step robust against undesired variances within the image stack.

Due to the nature of the (CB)CT images, the output of the first deep learning neural network will suffer from (before mentioned) potential artefacts such as averaging due to patient motion, beam hardening, etc. Another source of noise is variance in image data captured by different CT scanners. This variance results in various factors being introduced such as varying amounts of noise within the image stack, varying voxel intensity values representing the same (real world) density, and potentially others. The effects that the above-mentioned artefacts and noise sources have on the output of the first deep learning neural network may be removed or at least substantially reduced by the post-processing deep learning neural network, leading to segmented jaw voxels and segmented teeth voxels.

The classified nerve data 1508 may be post-processed separately from the jaw and teeth data. The nature of the nerve data, which represent long thin filament structures in the CT image data stack, makes this data less suitable for post-processing by a deep learning neural network. Instead, the classified nerve data is post-processed using an interpolation algorithm in order to procedure segmented nerve data 1516. To that end, voxels that are classified as nerve voxels and that are associated with a high probability (e.g. a probability of 95% or more) are used by the fitting algorithm in order to construct a 3D model of the nerve structures. Thereafter, the 3D jaw, teeth and nerve data sets 1518 may be processed into respective 3D models of the dento-maxillofacial structure.

Figure 16:
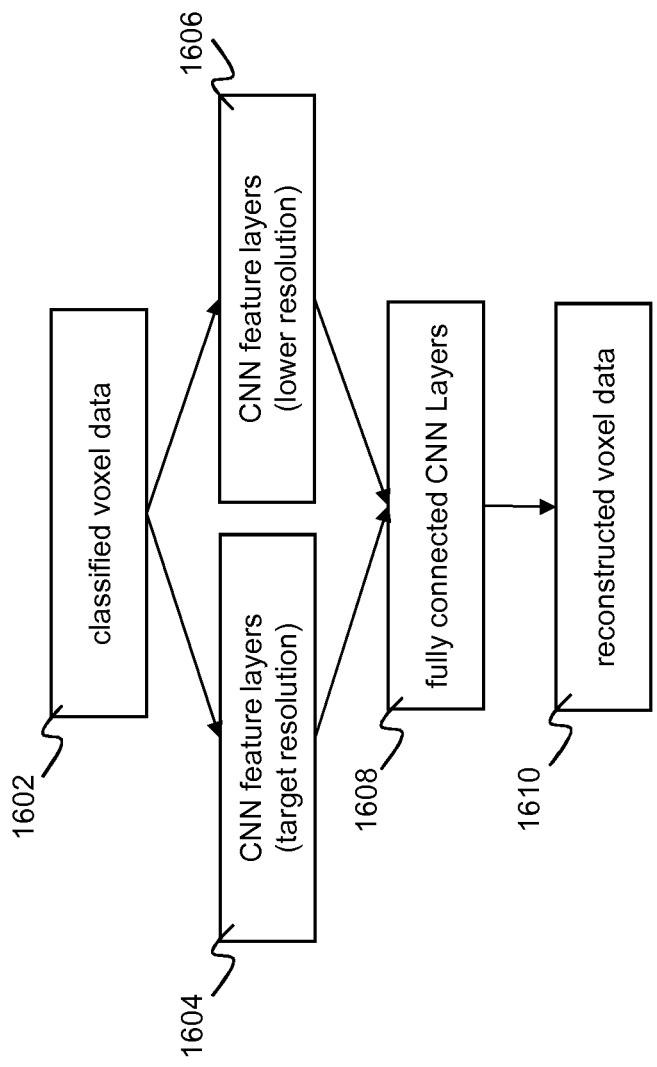
FIG. 16 depicts a deep neural network architecture for post-processing classified voxels of 3D dento-maxillofacial structures according to an embodiment of the invention.
Figure 17:
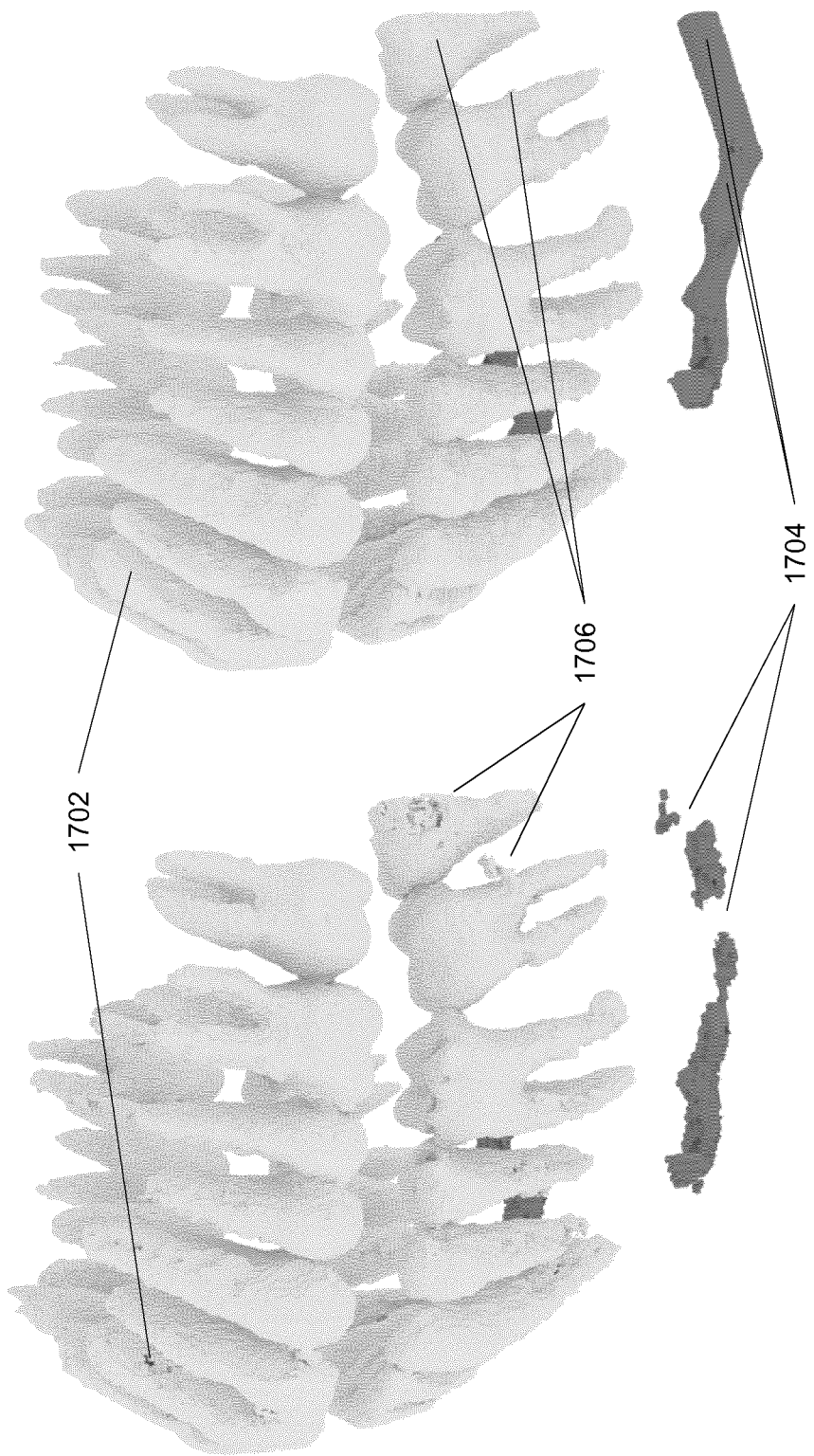
FIG. 17A-17B depict a reconstruction process of classified voxels according to an embodiment of the invention.

FIG. 16 depicts an example of an architecture of a deep learning neural network that is configured for post-processing classified voxels of a 3D dento-maxillofacial structure according to an embodiment of the invention. The post-processing deep learning neural network may have an architecture that is similar to the first deep learning neural network, including a first path formed by a first set of 3D CNN feature layers 1604, which is configured to process the input data (in this case a part of classified voxel data) at the resolution of the target. The deep learning neural network further includes a second set of 3D CNN feature layers 1606, which is configured to process the context of the input data that are processed by the first 3D CNN feature layers but then at a lower resolution than the target. The output of the first and second 3D CNN feature layers are then fed to the input of a set of fully connected 3D CNN layers 1608 in order to reconstruct the classified voxel data such that they closely represent a 3D model of the 3D dento-maxillofacial structure. The output of the fully connected 3D CNN layer provides the reconstructed voxel data.

The post-processing neural network may be trained using the same targets as first deep learning neural network, which represent the same desired output. During training, the network is made as broadly applicable as possible by providing noise to the inputs to represent exceptional cases to be regularized. Inherent to the nature of the post-processing deep learning neural network, the processing it performs also results in the removal of non-feasible aspects from the received voxel data. Factors here include the smoothing and filling of desired dento-maxillofacial structures, and the outright removal of non-feasible voxel data.

FIGS. 17A and 17B depict processing resulting in volume reconstruction and interpolation of classified voxels according to an embodiment of the invention. In particular, FIG. 17A depicts a picture of classified voxels of tooth and nerve structures, wherein the voxels are the output of the first deep learning neural network. As shown in the figure noise and other artefacts in the input data result in irregularities and artefacts in the voxel classification and hence 3D surface structures that include gaps in sets of voxels that represent a tooth structure. These irregularities and artefacts are especially visible at the inferior alveolar nerve structure and the dental root structures of the teeth, as also indicated with respect to FIG. 14B and FIG. 14D.

FIG. 17B depicts the result of the post-processing according the process as described with reference to FIG. 15 and FIG. 16. As shown in this figure the post-processing deep learning neural network successfully removes artefacts that were present in the input data (the classified voxels). The post-processing step successfully reconstructs parts that were substantially affected by the irregularities and artefacts, such as the root structures 1702 of the teeth which now exhibit smooth surfaces that provide an accurate 3D model of the individual tooth structures. High probability nerve voxels (e.g. a probability of 95% or more) may be used by a fitting algorithm in order to construct a 3D model of the nerve structures 1704. Also note that the imperfections with regards to FDI tooth index labels 37 and 38, as indicated with respect to FIG. 14B, have been corrected as well 1706.

Figure 18:
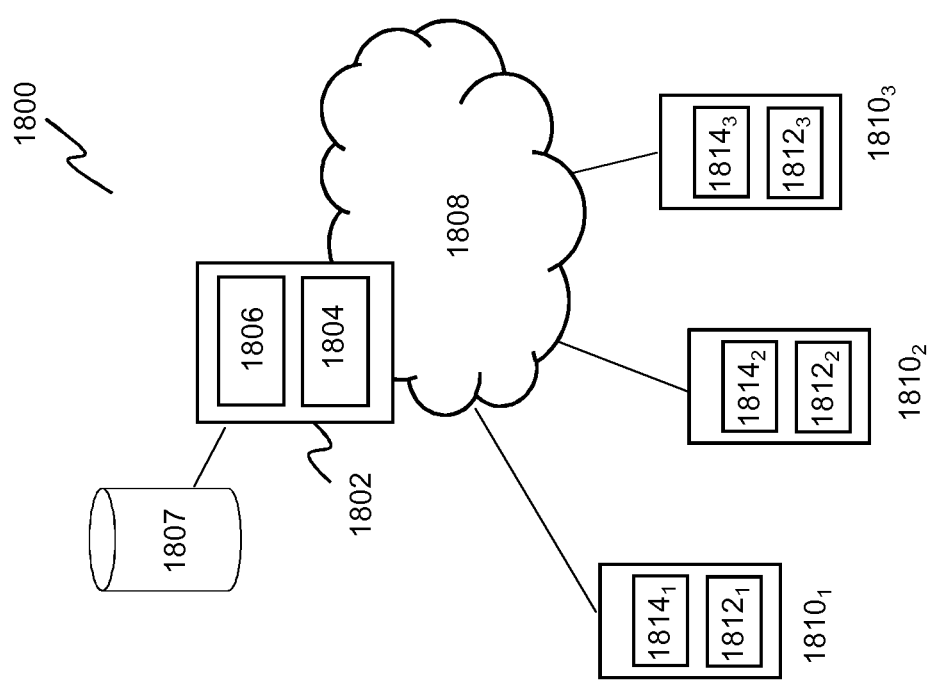
FIG. 18 depicts a schematic of a distributed computer system for processing 3D data according to various embodiments of the invention.

FIG. 18 depicts a schematic of a distributed computer system according to an embodiment of the invention. The distributed computer system may be configured to process the 3D data on the basis of the trained 3D deep learning processors as described in this application and for rendering the processed 3D data. As shown in FIG. 18, the trained 3D deep learning processors for segmenting 3D data dento-maxillofacial structures into individual 3D tooth models and for classifying of the tooth models in tooth types may be part of a distributed system comprising one or more servers 1802 in the network and multiple terminals $1810_{1-3}$, preferably mobile terminals, e.g. a desktop computer, a laptop, an electronic tablet, etc. The (trained) 3D deep learning processors may be implemented as server applications 1804, 1806. Further, a client application (a client device) $1812_{1-3}$ executed on the terminals may include a user interface enabling a user to interact with the system and a network interface enabling the client devices to communicate via one or more networks 1808, e.g. the Internet, with the server applications. A client device may be configured to receive input data, e.g. 3D (CB)CT data representing a dento-maxillofacial structure comprising a dentition or individual 3D tooth models forming a dentition. The client device may transmit the data to the server application, which may process (pre-process, segment, classify and/or process) the data on the basis of the methods and systems as described in this application. The processed data, e.g. taxonomized (labelled) 3D image data of tooth, may be sent back to the client device and a rendering engine $1814_{1-3}$ associated with the client device may use the processed 3D image data sets of the individual labelled 3D tooth models to render the 3D tooth models and labelling information, e.g. in the form of a dental chart or the like. In other embodiment, part or the data processing may be executed at the client side. For example, the pre-processing and/or post-processing described in this disclosure may be executed by the client device. In further embodiments, instead of a distributed computer system, a central computer system may be used to executed the pre-processing, post-processing and the classification processes described in this application.

Hence, as shown by FIG. 18, the invention provides a fully automated pipeline for taxonomy of 3D tooth models. A user may provide 3D image data, e.g. (CB)CT 3D data, including voxels representing of a dentition or a dento-maxillofacial structure comprising a dentition, to the input of the system and in response the system will generate individually labelled 3D tooth objects, which can be presented to the user in different graphical formats, e.g. as a 3D rendering or as markup in displayed image slices. The input data are automatically optimized for input to the 3D deep neural network so that the 3D deep neural network processors are capable of accurately processing (CB)CT 3D image data without any human intervention. Moreover, the invention allows 3D rendering of output generated by the 3D deep neural network processors, i.e. individually labelled 3D teeth of a dentition. Such visual information is indispensable for state of the art dental applications in dental care and dental reporting, orthodontics, orthognathic surgery, forensics, biometrics, etc.

Figure 19:
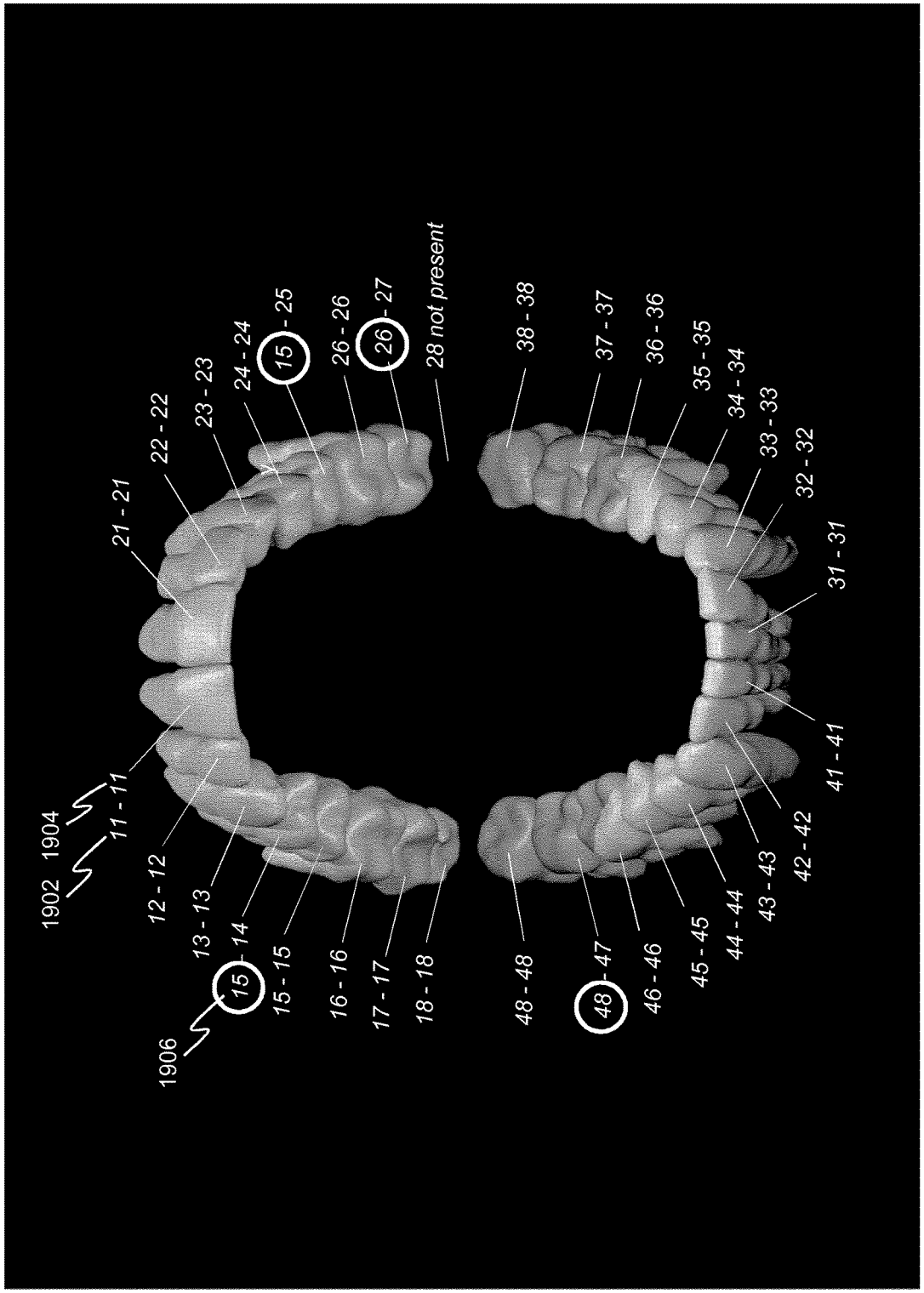
FIG. 19 depicts an example of labels applied to 3D data sets of teeth by a deep neural network classifying individual teeth and labels applied to a dentition resulting from post-processing.

FIG. 19 depicts an example of a processed set of teeth resulting from a system as described with reference to FIG. 7, including labels applied to 3D data sets of teeth by a deep neural network classifying individual teeth, and labels applied to a dentition resulting from post-processing. In particular, FIG. 19 depicts per tooth, before the dash symbol (for example 1902), the label with the highest activation value for the 3D data set for the individual tooth as resulting from classification using a deep learning neural network that is trained using a training method as described with reference to FIG. 5. Additionally FIG. 19 depicts per tooth, after the dash symbol (for example 1904), the label as assigned to the individual tooth in the resolved candidate state following post-processing as described with reference to FIG. 6. Classification labels that are depicted in red (for example 1906) would be incorrectly classified when only considering the labels with the highest activation resulting from the individual tooth deep learning network. These may be classified incorrectly due to for example an insufficiently trained deep learning network or exceptions in the input data. In this example the labels such as 1904 show the results of the taxonomy of the dentition having utilized the post-processing, having optimized the highest assigned activations whilst having satisfied the condition of every 3D data set representing an individual tooth being assigned a unique label.

Figure 20A:
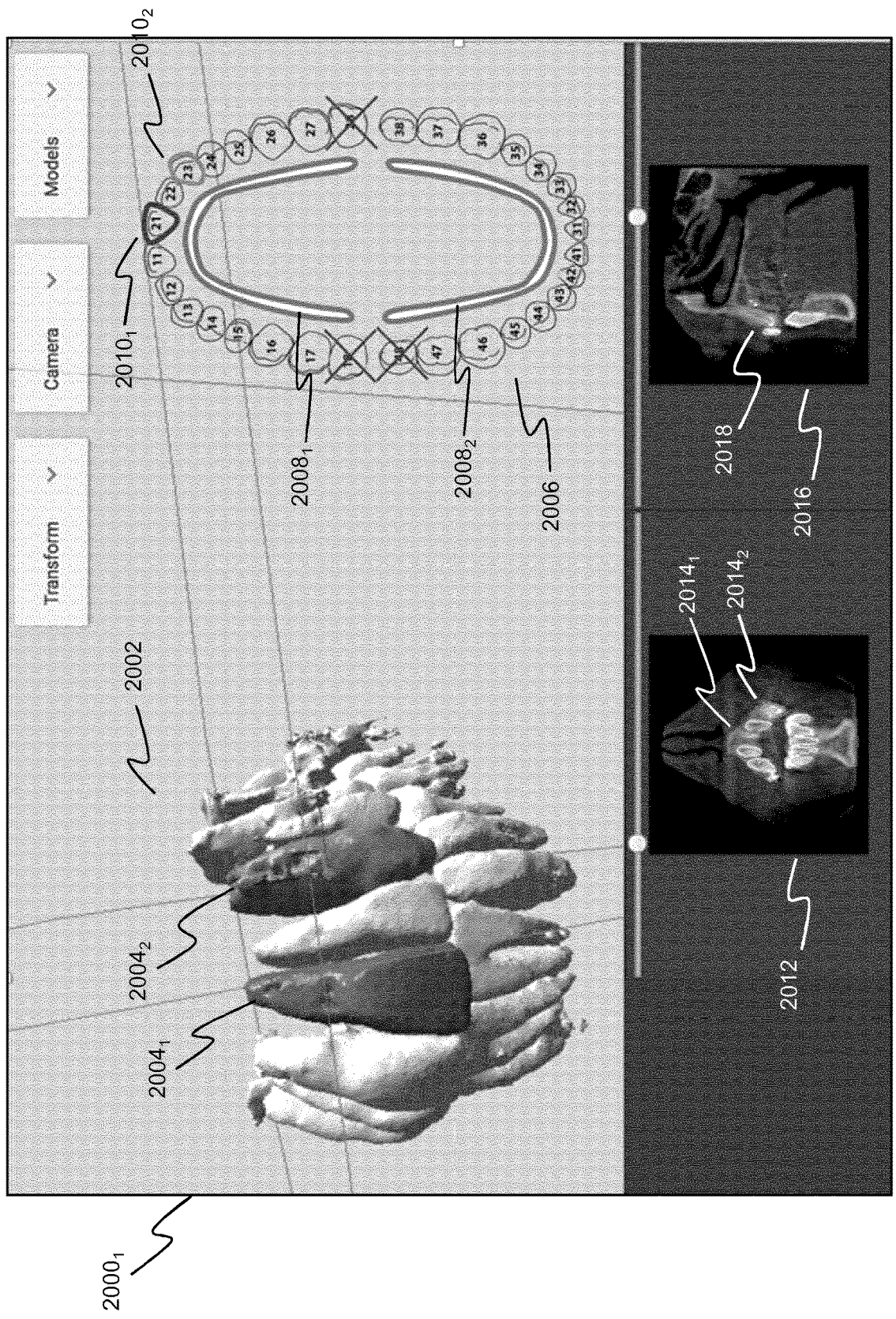
FIGS. 20A and 20B depict rendered dentitions comprising labelled 3D teeth models generated by a computer system according to an embodiment of the invention.
Figure 20B:
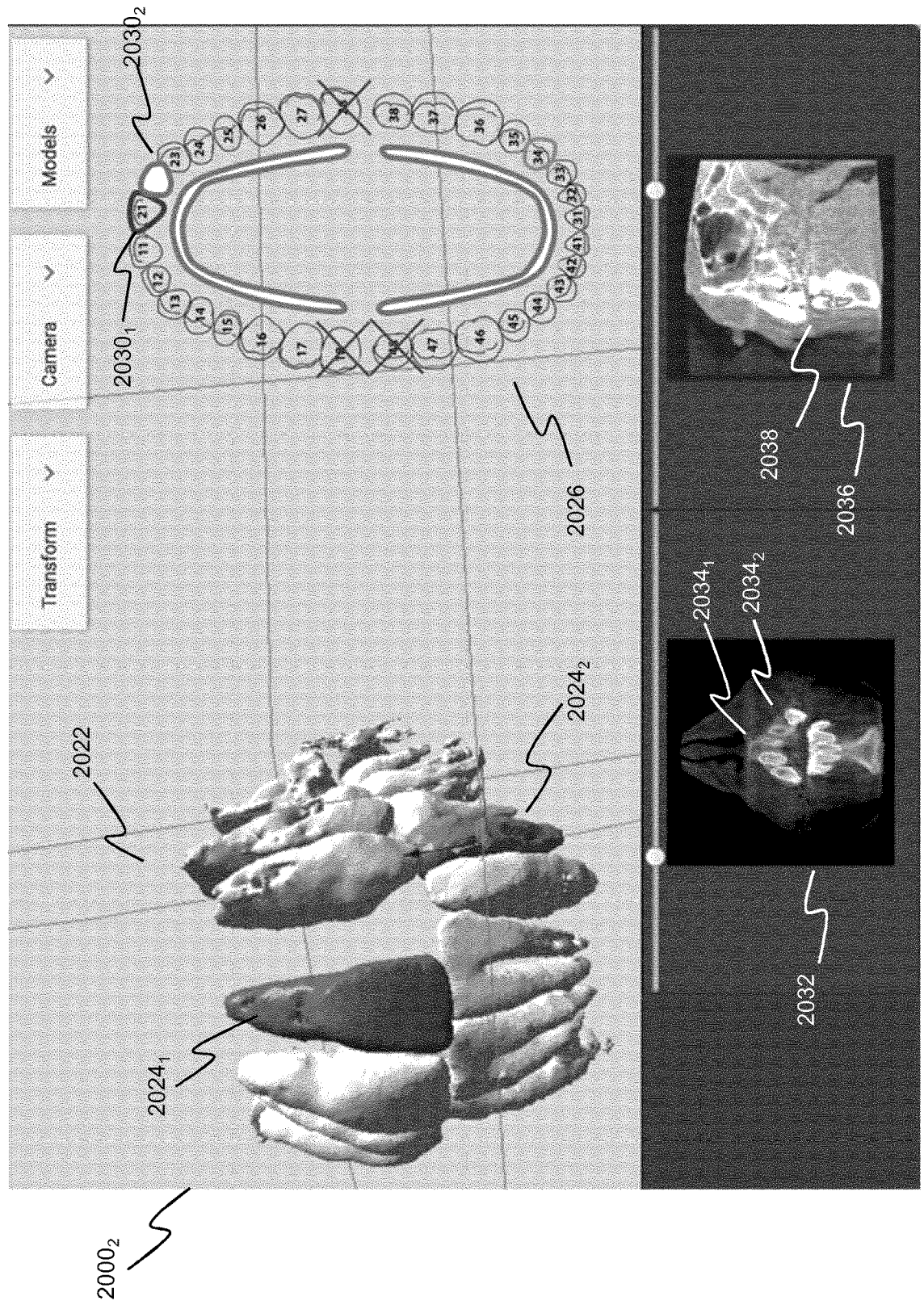

FIGS. 20A and 20B depict rendered dentitions comprising labelled 3D teeth models generated by a computer system according to an embodiment of the invention. These rendered dentitions may for example be generated by a distributed computer system as described with reference to FIGS. 18A and 18B. FIG. 20A depicts a first rendered dentition $2000_1$ including individually labelled 3D tooth models 2002, wherein individual 3D tooth models may be generated on the basis of a CBCT 3D data stack that was fed to the input of the computer system (as described with reference to FIG. 7-17). As described with reference to FIG. 18, the computer system may include a 3D deep learning processor configured to generate individually identified 3D teeth models, e.g. in the form of 3D surface meshes, which may be fed to the input of a processors that are configured to execute a taxonomy process for classifying (labelling) the 3D tooth models (as for example described with reference to FIG. 3).

The trained 3D deep neural network processor of this computer system may classify 3D tooth data of the dentition into the applicable tooth types that can be used in e.g. an electronic dental chart 2006 that includes the 32 possible teeth of an adult. As shown in the figure, such a dental chart may include an upper set of teeth which are spatially arranged according to an upper dental arch 2008, and a lower set of teeth which are spatially arranged according to lower dental arch 20082. After the taxonomy process, each of the 3D tooth models derived from voxel representations may be labelled with a tooth type and associated with a position in the dental map. For example, the automated taxonomy process may identify a first 3D tooth object $2004_1$ as an upper left central incisor (identified in the dental chart as a type 21 tooth $2010_1$) and a second 3D tooth object $2004_2$ as a cuspid (identified in the dental chart as a type 23 tooth $2010_2$).

When taxonomizing all individual 3D tooth models of a 3D data set, the computer may also determine that some teeth are missing (e.g. the third upper left and upper right molar and the third lower left molar). Additionally, slices of the 3D input data representing the dento-maxillofacial structure may be rendered, e.g. a slice of the axial plane 2012 and a slice of the sagittal plane 2016. Because the process includes classifying voxels of the 3D input data into different parts of the dento-maxillofacial structure (e.g. individual jaw sections, individual teeth or individual nerve), the computer system knows which voxels in the 3D data stack belong to an individual tooth. This way, the computer can directly relate one or more 3D tooth objects $2004_{1,2}$ to pixels in the slices so that these pixels can be easily selected and highlighted, e.g. highlighted pixels $2014_{1,2}$ and 2018, and/or hidden. FIG. 20B depicts rendered dentition $2000_2$ including labelled 3D tooth objects 2022 that is similar to FIG. 20A. Individual 3D tooth models $2024_{1,2}$ may be labelled using a dental chart 2026 and/or slices 2032, 2036 which provide both visual information about the position and the tooth type, and the ability to show/hide the labelled models of the classified 3D tooth models and about the tooth types $2030_{1,2}$. For example, as shown in FIG. 20B, the system may allow selection of tooth type 22 $2030_2$ and hide the associated 3D tooth model in the 3D render of the dentition.

Figure 21:
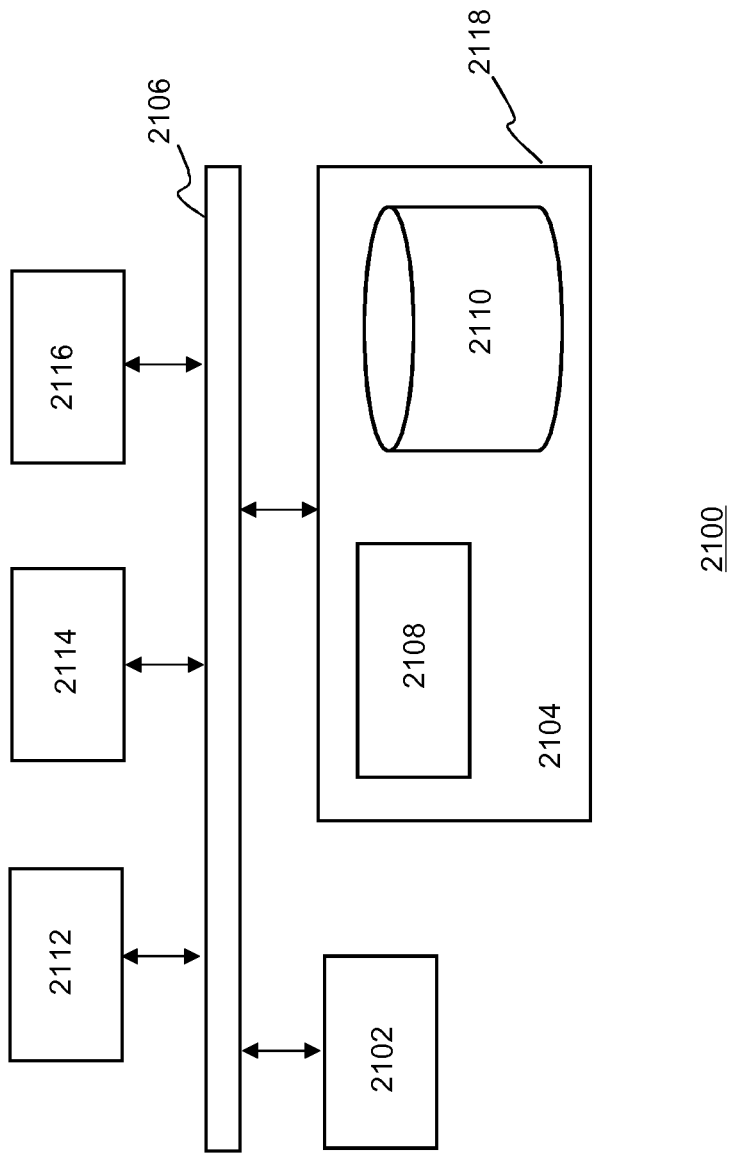
FIG. 21 is a block diagram illustrating an exemplary data computing system that may be used for executing methods and software products described in this disclosure.

FIG. 21 is a block diagram illustrating exemplary data processing systems described in this disclosure. Data processing system 2100 may include at least one processor 2102 coupled to memory elements 2104 through a system bus 2106. As such, the data processing system may store program code within memory elements 2104. Further, processor 2102 may execute the program code accessed from memory elements 2104 via system bus 2106. In one aspect, data processing system may be implemented as a computer that is suitable for storing and/or executing program code. It should be appreciated, however, that data processing system 2100 may be implemented in the form of any system including a processor and memory that is capable of performing the functions described within this specification.

Memory elements 2104 may include one or more physical memory devices such as, for example, local memory 2108 and one or more bulk storage devices 2110. Local memory may refer to random access memory or other non-persistent memory device(s) generally used during actual execution of the program code. A bulk storage device may be implemented as a hard drive or other persistent data storage device. The processing system 2100 may also include one or more cache memories (not shown) that provide temporary storage of at least some program code in order to reduce the number of times program code must be retrieved from bulk storage device 2110 during execution.

Input/output (I/O) devices depicted as input device 2112 and output device 2114 optionally can be coupled to the data processing system. Examples of input device may include, but are not limited to, for example, a keyboard, a pointing device such as a mouse, or the like. Examples of output device may include, but are not limited to, for example, a monitor or display, speakers, or the like. Input device and/or output device may be coupled to data processing system either directly or through intervening I/O controllers. A network adapter 2116 may also be coupled to data processing system to enable it to become coupled to other systems, computer systems, remote network devices, and/or remote storage devices through intervening private or public networks. The network adapter may comprise a data receiver for receiving data that is transmitted by said systems, devices and/or networks to said data and a data transmitter for transmitting data to said systems, devices and/or networks. Modems, cable modems, and Ethernet cards are examples of different types of network adapter that may be used with data processing system 2100.

As pictured in FIG. 21, memory elements 2104 may store an application 2118. It should be appreciated that data processing system 2100 may further execute an operating system (not shown) that can facilitate execution of the application. Application, being implemented in the form of executable program code, can be executed by data processing system 2100, e.g., by processor 2102. Responsive to executing application, data processing system may be configured to perform one or more operations to be described herein in further detail.

In one aspect, for example, data processing system 2100 may represent a client data processing system. In that case, application 2118 may represent a client application that, when executed, configures data processing system 2100 to perform the various functions described herein with reference to a "client". Examples of a client can include, but are not limited to, a personal computer, a portable computer, a mobile phone, or the like.

In another aspect, data processing system may represent a server. For example, data processing system may represent an (HTTP) server in which case application 2118, when executed, may configure data processing system to perform (HTTP) server operations. In another aspect, data processing system may represent a module, unit or function as referred to in this specification.

The terminology used herein is for the purpose of describing particular embodiments only and is not intended to be limiting of the invention. As used herein, the singular forms "a," "an," and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

The corresponding structures, materials, acts, and equivalents of all means or step plus function elements in the claims below are intended to include any structure, material, or act for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiment was chosen and described in order to best explain the principles of the invention and the practical application, and to enable others of ordinary skill in the art to understand the invention for various embodiments with various modifications as are suited to the particular use contemplated.

The invention claimed is:

1. A computer-implemented method for processing 3D data representing a dento-maxillofacial structure comprising:
   receiving 3D data data including a voxel representation of the dento-maxillofacial structure, the dento-maxillofacial structure comprising a dentition, a voxel at least being associated with a radiation intensity value, the voxels of the voxel representation defining an image volume;
   providing the voxel representation to the input of a first 3D deep neural network, the 3D deep neural network being trained to classify voxels of the voxel representation into one or more tooth classes; the first deep neural network comprising a plurality of first 3D convolutional layers defining a first convolution path and a plurality of second 3D convolutional layers defining a second convolutional path parallel to the first convolutional path, the first convolutional path configured to receive at its input a first block of voxels of the voxel representation and the second convolutional path being configured to receive at its input a second block of voxels of the voxel representation, the first and second block of voxels having the same or substantially the same center point in the image volume and the second block of voxels representing a volume in real-world dimensions that is larger than the volume in real-world dimensions of the first block of voxels, the second convolutional path determining contextual information for voxels of the first block of voxels; the output of the first and second convolutional path being connected to at least one fully connected layer for classifying voxels of the first block of voxels into one or more tooth classes; and,
   the computer receiving classified voxels of the voxel representation of the dento-maxillofacial structure from the output of the first 3D deep neural network.

2. The method according to claim 1, wherein the volume of the second block of voxels is larger than the volume of the first block of voxels, the second block of voxels representing a down-sampled version of the first block of voxels.

3. The method according to claim 2, wherein the second block of voxels representing the down-sampled version of the first block of voxels comprises a down-sampling factor selected between 20 and 2, more preferably between 10 and 3.

4. The method according to claim 3, wherein down-sampling factor is selected between 10 and 3.

5. The method according to claim 1 further comprising:
   the computer determining one or more voxel representations of single tooth of the dento-maxillofacial structure on the basis of the classified voxels;
   the computer providing each of the one or more voxel representations of single tooth to the input of a second 3D deep neural network, the second 3D deep neural network being trained to classify a voxel representation of a single tooth into one of a plurality of tooth classes of a dentition, each tooth class being associated with a candidate tooth class label, the second trained 3D neural network generating for each of the candidate tooth class labels an activation value, an activation value associated with a candidate tooth class label defining a likelihood that a voxel representation of a single tooth represents a tooth class as indicated by the candidate tooth class label.

6. The method of claim 5 wherein the one or more tooth classes comprises at least 32 tooth classes of a dentition.

7. The method according to claim 1 further comprising:
   determining a taxonomy of the dentition including: defining candidate dentition states, each candidate state being formed by assigning a candidate tooth class label to each of a plurality of voxel representations of single tooth based on the activation values; and, evaluating the candidate dentition states on a basis of one or more conditions, at least one of the one or more conditions requiring that different candidate tooth class labels assigned different voxel representations of single tooth.

8. The method according to claim 1 further comprising:
   using a pre-processing algorithm to determine 3D positional feature information of the dento-maxillofacial structure, the 3D positional feature information defining for each voxel in the voxel representation about the position of the voxel relative to the position of a dental reference object in the image volume, and;
   adding the 3D positional feature information to the 3D data before providing the 3D data to the input of the first deep neural network, the added 3D positional feature information providing an additional data channel to the 3D data.

9. The method according to claim 1 comprising:
   post-processing the voxels classified by the first 3D deep neural network on the basis of a third trained neural network, the third trained neural network being trained to receive voxels that are classified by the first trained neural network at its input and to correct voxels that are incorrectly classified by the first deep neural network.

10. The method according to claim 9 wherein the third neural network being trained based on voxels that are classified during the training of the first deep neural network as input and based on the one or more 3D data sets of parts of the dento-maxillofacial structures of the 3D image data of the training set as a target.

11. The computer implemented method of claim 1 wherein the one or more tooth classes comprises at least 32 tooth classes of a dentition.

12. A non-transitory computer readable medium having software code portions stored thereon, wherein the software code portions are configured for, when run in a memory of a computer, executing the method according to claim 1.

* * * * *